(12) United States Patent
Ip et al.

(10) Patent No.: US 9,629,830 B2
(45) Date of Patent: Apr. 25, 2017

(54) EPHA4 INHIBITORS AS NEUROPROTECTIVE AGENTS

(71) Applicant: The Hong Kong University of Science and Technology, Hong Kong (CN)

(72) Inventors: Nancy Yuk Yu Ip, Hong Kong (CN); Kit Yu Fu, Hong Kong (CN); Fanny Chui Fun Ip, Hong Kong (CN); Wing Yu Fu, Hong Kong (CN); Shuo Gu, Zhejiang (CN); Xuhui Huang, Hong Kong (CN); Kwok Wang Hung, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 0 days.

(21) Appl. No.: 14/905,723

(22) PCT Filed: Jul. 17, 2014

(86) PCT No.: PCT/CN2014/082386
§ 371 (c)(1),
(2) Date: Jan. 15, 2016

(87) PCT Pub. No.: WO2015/007222
PCT Pub. Date: Jan. 22, 2015

(65) Prior Publication Data
US 2016/0152618 A1    Jun. 2, 2016

Related U.S. Application Data

(60) Provisional application No. 61/847,432, filed on Jul. 17, 2013.

(51) Int. Cl.
A61K 31/438     (2006.01)
C07D 471/20     (2006.01)
(Continued)

(52) U.S. Cl.
CPC .......... *A61K 31/438* (2013.01); *A61K 31/352* (2013.01); *A61K 31/402* (2013.01);
(Continued)

(58) Field of Classification Search
CPC ........................ A61K 31/438; C07D 471/20
(Continued)

(56) References Cited

FOREIGN PATENT DOCUMENTS

WO    WO-2004/028551    4/2004

OTHER PUBLICATIONS

Compton and Coles, "Multiple Sclerosis," Lancet (2002), vol. 359, pp. 1221-1231.*
(Continued)

*Primary Examiner* — Kamal Saeed
*Assistant Examiner* — Janet L Coppins
(74) *Attorney, Agent, or Firm* — Foley & Lardner LLP

(57) ABSTRACT

Provided is the discovery of the role of EphA4 signaling in neurodegenerative disorders involving β-amyloid induced neurotoxicity such as Alzheimer's Disease. New therapeutic methods, therapeutic agents, and kits for treating diseases caused or exacerbated by overactivated EphA4 signaling are provided. Also provided are methods for identifying additional compounds as therapeutic agents useful for treating conditions involving overly active EphA4 signaling.

22 Claims, 32 Drawing Sheets

(51) Int. Cl.
  A61K 31/437  (2006.01)
  A61K 31/352  (2006.01)
  A61K 31/402  (2006.01)
  A61K 31/403  (2006.01)
(52) U.S. Cl.
  CPC .......... *A61K 31/403* (2013.01); *A61K 31/437* (2013.01); *C07D 471/20* (2013.01)
(58) Field of Classification Search
  USPC ............................................ 514/299; 546/15
  See application file for complete search history.

(56) References Cited

OTHER PUBLICATIONS

Freshney, Ian, Culture of Animal Cells, Sixth Edition (2010), pp. 1-5.*
Maltsev et al, "The role of b-amyloid peptide in neurodegenerative diseases," Ageing Research Reviews (2011), vol. 10, pp. 440-452.*
Tarsy, Daniel MD, "Patient Information: Parkinson disease treatment options-medications," www.uptodate.com, 2016.*
Shuanglu, Xie et al, "Systematic identification and quantification of tetracyclic monoterpenoid oxindole alkaloids in Uncaria rynchopphylla and their fragmentations in Q-TOF-MS spectra," J. Pharm. & Biomedical Analysis (2013), vol. 81-82, pp. 56-64.*
Bourgin et al., "The EphA4 receptor regulates dendritic spine remodeling by affecting beta1-integrin signaling pathways," J. Cell. Biol. 178: 1295-1307 (2007).
Bouvier et al., "EphA4 is localized in clathrin-coated and synaptic vesicles in adult mouse brain," J. Neurochem. 113: 153-165 (2010).
Bowden et al., "Structural Plasticity of Eph Receptor A4 Facilitates Cross-Class Ephrin Signaling," Structure 17: 1386-1397 (2009).
Cameron et al., "Inflammation, microglia, and Alzheimer's disease," Neurobiol. Dis. 37: 503-509 (2010).
Carmona et al., "Glial ephrin-A3 regulates hippocampal dendritic spine morphology and glutamate transport," Proc. Natl. Acad. Sci. USA 106: 12524-12529 (2009).
Chen et al., "Bidirectional signaling of ErbB and Eph receptors at synapses," Neuron Glia. Biol. 4: 211-221 (2008).
Chen et al., "Eph receptors at synapses: Implications in neurodegenerative diseases," Celullar Signalling 24: 606-611 (2012).
Cisse et al., "Reversing EphB2 depletion rescues cognitive functions in Alzheimer model," Nature 469: 47-52 (2011).
Dalva et al., "EphB receptors interact with NMDA receptors and regulate excitatory synapse formation," Cell 103: 945-956 (2000).
David et al., "Neurogenesis-Dependent and -Independent Effects of Fluoxetine in an Animal Model of Anxiety/Depression," Neuron 62: 479-493 (2009).
Fang et al., "Overproduction of Upper-Layer Neurons in the Neocortex Leads to Autism-like Features in Mice," Neuron 79: 665-679 (2013).
Faruqi, "EPHA4 inhibition rescues neurodegeneration in ALS," Nat. Rev. Drug Discov. 11(10): 747 (2012).
Filosa et al., "Neuron-glia communication via EphA4/ephrin-A3 modulates LTP through glial glutamate transport," Nat. Neurosci. 12: 1285-1292 (2009).
Fu et al., "APC (Cdh1) mediates EphA4-dependent downregulation of AMPA receptors in homeostatic plasticity," Nat. Neurosci. 14: 181-189 (2011).
Fu et al., "Cdk5 regulates Eph4A-mediated dendritic spine retraction through an ephexin1-dependent mechanism," Nat. Neurosci. 10: 67-76 (2007).
Fukai et al.,"EphA4 promotes cell proliferation and migration through a novel EphA4-FGFR1 signaling pathway in the human glioma U251 cell line," Mol. Cancer Ther. 7(9): 2768-2778 (2008).
Goldschmit et al., "EphA4 Blockers Promote Axonal Regeneration and Functional Recovery Following Spinal Cord Injury in Mice," J. Neurosci. 24(45): 10064-10073 (2004).
Goldschmit et al., "EphA4 blockers promote axonal regeneration and functional recovery following spinal cord injury in mice," PLoS One 6, e24636 (2011).
Hauser et al., "The Neurobiology of Multiple Sclerosis: Genes, Inflammation, and Neurodegeneration," Neuron 52(1): 61-76 (2006).
Hernández-Pedro et al., "Initial Immunopathogenesis of Multiple Sclerosis: Innate Immune Response," Clin. Dev. Immunol. 413-465 (2013).
Hsieh et al., "AMPAR Removal Underlies A[Beta]-induced Synaptic Depression and Dendritic Spine Loss," Neuron 52: 831-843 (2006).
Huang et al., "Alzheimer mechanisms and therapeutic strategies," Cell 148(6): 1204-1222 (2012).
Huey et al., "A semiempirical free energy force field with a charge-based desolvation," J. Comput. Chem. 28: 1145-1152 (2007).
International Search Report issued on PCT/CN2014/082386, mailed Oct. 22, 2014.
Jacobsen et al., "Early-onset behavioral and synaptic deficits in a mouse model of Alzheimer's disease," Proc. Natl. Acad. Sci. USA 103: 5161-5166 (2006).
Jo et al., "A[beta]1-42 inhibition of LTP is mediated by a signaling pathway involving caspase-3, Akt1 and GSK-3[beta]," Nat. Neurosci. 14: 545-547 (2011).
Kang et al., "Protective effect of rhynchophylline and isorhynchophylline on in vitro ischemia-induced neuronal damage in the hippocampus: putative neurotransmitter receptors involved in their action," Life Sci. 76: 331-343 (2004).
Kang et al., "Rhynchopylline and isorhynchophylline inhibit NMDA receptors expressed in Xenopus oocytes," Eur. J. Pharmacol. 455: 27-34 (2004).
Kawakami et al., "Isoliquiritigenin is a novel NMDA receptor antagonist is kampo medicine yokukansan," Cell Mol. Neurobiol. 31: 1203-1212 (2011).
Klein, "A[Beta] toxicity in Alzheimer's disease: globular oligomers (ADDLs) as new vaccine and drug targets," Neurochem. Intl. 41: 345-352 (2002).
Klein, "Bidirectional modulation of synaptic functions by Eph/ephrin signaling," Nat. Neurosci. 12: 15-20(2009).
Koffie et al., "Oligomeric amyloid [beta] associates with postsynaptic densities and correlates with excitatory synapse loss near senile plaques," Proc. Natl. Acad. Sci. USA 106: 4012-4017 (2009).
Lacor et al., "Abeta oligomer-induced aberrations in synapse composition, shape, and density provide a molecular basis for loss of connectivity in Alzheimer's disease," J. Neurosci. 27: 796-807 (2007).
Lacor et al., "Synaptic Targeting by Alzheimer's-Related Amyloid [Beta] Oligomers," J. Neurosci. 24: 10191-10200 (2004).
Lambert et al., "Diffusible, nonfibrillar ligands derived from A[Beta]1-42 are potent central nervous system neurotoxins," Proc. Natl. Acad. Sci. USA 95: 6448-6453 (1998).
Lambert et al., "Vaccination with soluble A[Beta] oligomers generates toxicity-neutralizing antibodies," J. Neurochem. 79(3): 595-605 (2001).
Lamberto et al., "Distinctive binding of three antagonistic peptides to the ephrin-binding pocket of the EphA4 receptor," Biochem. J. 445: 47-56 (2012).
Langer, "New Methods of Drug Delivery." Science (1990) 249: 1527-1533.
Lassman, "Multiple sclerosis: Lessons from molecular neuropathology," Exp. Neurol. 262A: 2-7 (2014).
Lee et al., "Major Depression: A Role for Hippocampal Neurogenesis?," Curr. Top. Behav. Neurosci. 14: 153-179 (2013).
Lemmens et al., "Modifying expression of EphA4 and its downstream targets improves functional recovery after stroke," Hum. Mol. Genet. 22(11): 2214-2220 (2013).
Li et al., "Inhibition of EphA4 signaling after ischemia—reperfusion reduces apoptosis of CA1 pyramidal neurons," Neurosci. Lett. 518(2): 92-95 (2012).
Li et al., "Soluble Oligomers of Amyloid [Beta] protein Facilitate Hippocampal Long-Term Depression by Disrupting Neuronal Glutamate Uptake," Neuron 62: 788-801 (2009).

(56) References Cited

OTHER PUBLICATIONS

Liu et al., "Involvement of ephrin receptor A4 in pancreatic cancer cell motility and invasion," Oncol. Lett. 7(6): 2165-2169 (2014).
Logue et al., "A comprehensive genetic association study of Alzheimer disease in African Americans," Arch. Neurol. 1569-1579 (2011).
Masi et al., "The Hippocampus, Neutrophic Factors and Depression," CNS Drugs 25: 913-931 (2011).
Masliah et al., "Abnormal Glutamate Transport Function in Mutant Amyloid Precursor Protein Transgenic Mice," Exper. Neurol. 163: 381-387 (2000).
Massa et al., "Small molecule BDNF mimetics activate TrkB signaling and prevent neuronal degeneration in rodents," J. Clin. Invest. 120: 1774-1785 (2010).
Miyazaki et al., "EphA4 is a prognostic factor in gastric cancer," BMC Clin. Pathol. 13: 19 (2013).
Morris et al., "AutoDock4 and AutoDockTools4: Automated docking with selective receptor flexibility," J. Comput. Chem. 30: 2785-2791 (2009).
Morris et al., Automated docking using a Lamarckian genetic algorithm and an empirical binding free energy function, J. Comput. Chem. 19: 1639-1662 (1998).
Muñoz et al., J. Immunol. 169(1): 177-845 (2002).
Munro et al., "Differential gene expression in the EphA4 knockout spinal cord and analysis of the inflammatory response following spinal cord injury," PLoS One 7, e37635 (2012).
Murai et al., "Control of hippocampal dendritic spine morphology through ephrin-A3/EphA4 signaling," Nat. Neurosci. 6: 153-160 (2003).
Murai et al., "Eph receptors and ephrins in neuro-astrocyte communications at synapses," Glia 59: 1567-1578 (2011).
Murai et al., "Targeting the EphA4 receptor in the nervous system with biologically active peptides," Mol. Cell. Neurosci. 24(4): 1000-1011 (2003).
Noberini et al., "Inhibition of Eph receptor-ephrin ligand interaction by tea polyphenols," Pharmacol. Res. 66: 363-373 (2012).
Noberini et al., "Small molecules can selectively inhibit ephrin binding to the EphA4 and EphA2 receptors," J. Biol. Chem. 283(43): 29461-29472 (2008).
Noberini et al., "Targeting Eph receptors with peptides and small molecules: progress and challenges," Semin. Cell. Dev. Biol. 23: 51-57 (2012).
Oki et al., "Overexpression of the receptor tyrosine kinase EphA4 in human gastric cancers," World J. Gastroenterol. 12: 5650-5656 (2008).
Oshima et al., "Overexpression of EphA4 gene and reduced expression of EphB2 gene correlates with liver metastasis in colorectal cancer," Int. J. Oncol. 33: 573-577 (2008).
Palop et al., "Amyloid-beta-induced neuronal dysfunction in Alzheimer's disease: from synapses towards neural networks," Nat. Neurosci. 13: 812-818 (2010).
Parmentier-Batteur et al., "Attenuation of scratch-induced reactive astrogliosis by novel EphA4 kinase inhibitors," J. Neurochem. 118(6): 1016-1031 (2011).
Pasquale, "Eph receptor signaling casts a wide net on cell behavior," Nat. Rev. Mol. Cell. Biol. 6(6): 462-475 (2005).
Pasquale, "Eph-ephrin bidirectional signaling in physiology and disease," Cell 133: 38-52 (2008).
Qin et al., "Crystal structure and the NMR binding reveal that two small molecule antagonists target the high affinity ephrin-binding channel of the EphA4 receptor," J. Biol. Chem. 283: 29473-29484 (2008).
Qin et al., "Structural characterization of the EphA4-Ephrin-B2 complex reveals new features enabling Eph-ephrin binding promiscuity," J. Biol. Chem., 285: 644-654 (2010).
Renner et al., "Deleterious effects of Amyloid [beta] Oligomers Acting as an Extracellular Scaffold for mGluR5," Neuron 66: 739-754 (2010).

Richter et al., "The EphA4 receptor regulates neuronal morphology through SPAR-mediated inactivation of Rap GTPases," J. Neurosci. 27: 14205-14215 (2007).
Sala et al., "Inhibition of dendritic spine morphogenesis and synaptic transmission by activity-inducible protein Homer1a," J. Neurosci. 23: 6327-6337 (2003).
Selkoe, "Alzheimer's Disease is a Synaptic Failure," Science 298: 789-791 (2002).
Shankar et al., "Amyloid-[beta] protein dimers isolated directly from Alzheimer's brains impair synaptic plasticity and memory," Nat. Med. 14: 837-842 (2008).
Shankar et al., "Natural oligomers of the Alzheimer amyloid-beta protein induce reversible synapse loss by modulating an NMDA-type glutamate receptor-dependent signaling pathway," J. Neurosci. 27: 2866-2875 (2007).
Sheffler-Collins et al., "EphBs: an integral link between synaptic function and synaptopathies," Trends in Neurosci. 35: 293-304 (2012).
Shen et al., "Melanocortin-4 Receptor Regulates Hippocampal Synaptic Plasticity through a Protein Kinase A-Dependent Mechanism," J. Neurosci. 33: 464-472 (2013).
Shen et al., "Whole genome association study of brain-wide imaging phenotypes for identifying quantitative trait loci in MCI and AD: A study of the ADNI cohort," NeuroImage 53(3): 1051-1063 (2010).
Sheng et al., "Synapses and Alzheimer's disease," Cold Spring Harb. Perspect. Biol. 4 (2012).
Shi et al., "Alpha2-chimaerin interacts with EphA4 anf regulates EphA4-dependent growth cone collapse," Proc. Natl. Acad. Sci. USA 104: 16347-16352 (2007).
Simon et al., "Early changes in hippocampal Eph receptors precede the onset of memory decline in mouse models of Alzheimer's disease," J. Alzheimers Dis. 17: 773-786 (2009).
Singla et al., "Crystal structure of the ligand-binding domain of the promiscuous EphA4 receptor reveals two distinct conformations," Biochem. and Biophys. Res. Comm. 399: 555-559 (2010).
Snyder et al., "Regulation of the NMDA receptor trafficking by amyloid-beta," Nat. Neurosci. 8: 1051-1058 (2005).
Sobel, "Ephrin A Receptors and Ligands in Lesions and Normal-Appearing White Matter in Multiple Sclerosis," Brain Pathol. 15(1): 35-45 (2005).
Spanevello et al., "Acute Delivery of EphA4-Fc Improves Functional Recovery after Contusive Spinal Cord Injury in Rats," J. Neutrotrauma 30(12): 1023-1034 (2013).
Thomas-Crusells et al., "A novel method for monitoring surface membrane trafficking on hippocampal acute slice preparation," J. Neurosci. Methods 125: 159-166 (2003).
Ting et al., "Amyloid precursor protein overexpression depresses excitatory transmission through both presynaptic and postsynaptic mechanisms." Proc. Natl. Acad. Sci. USA 104: 353-358 (2007).
Van Hoecke et al., "EPHA4 is a disease modifier of amyotrophic lateral sclerosis in animal models and in humans," Nat. Med. 18(9): 1418-1422 (2012).
Van Linden et al., "Fragment based lead discovery of small molecule inhibitors for the EPHA4 receptor tyrosine kinase," Eur. J. Med. Chem. 47(1): 493-500 (2012).
Venkitaramani et al., "[Beta]-Amyloid Modulation of Synaptic Transmission and Plasticity," J. Neurosci. 27: 11832-11837 (2007).
Walsh et al., "Naturally secreted oligomers of amyloid [beta] protein potently inhibit hippocampal long-term potentiation in vivo," Nature 416: 535-539 (2002).
Wan et al., "Tyk2/STAT3 signaling mediates beta-amyloid-induced neuronal cell death: implications in Alzheimer's disease," J. Neurosci. 30: 6873-6881 (2010).
Xiong et al., "Chinese herbal formulas for treating hypertension in traditional Chinese medicine: perspective of modern science," Hypertension Research 36(7): 570-579 (2013).
Zhao et al., "Insulin Receptor Dysfunction Impairs Cellular Clearance of Neurotoxic Oligomeric A[Beta]," J. Biol Chem. 284: 18742-18753 (2009).
Zhou et al., "Antihypertensive and neuroprotective activities of rhynchophylline: The role of rhynchophylline in neutrotransmission and ion channel activity," J. Ethnopharmacology 132: 15-27 (2010).

(56) References Cited

OTHER PUBLICATIONS

Zhou et al., "EphA4 signaling regulates phospholipase Cgamma1 activation, cofilin membrane association, and dendritic spine morphology," J. Neurosci. 27: 5127-5138 (2007).

Zhou et al., "Individual and combined effects of rhynchophylline and ketamine on proliferation, NMDAR1 and GluA2/3 protein expression in PC12 cells," Fitoterapia 85: 129-129 (2013).

Database CA (Online) Chen et al., Preparation of the oral solutions of Dendrobium nobile, Database accession No. 1997:173986, 1996.

Database CA (online) He, Guohua: "Anticancer oral liquid continuing Dendrobium nobile Lindl", data base accession No. 2013:1085585, Jul. 10, 2013.

Database CA (Online) Hua et al., "New formulations of dendrobine for preventing and treating arthritis and protecting digestive tract mucosa from injury," Database accession No. 2008:86511, Jan. 16, 2008.

Fu et al., "Blockade of EphA4 signaling ameliorates hippocampal synaptic dysfunctions in mouse models of Alzheimer's disease," Proceedings of the National Academy of Sciences, vol. 111, No. 27, Jun. 23, 2014, pp. 9959-9964.

Fujiwara et al., "Uncaria rhynchophylla, a Chinese medicinal herb, has potent antiaggregation effects on Alzheimer's beta-amyloid proteins," Journal of Neuroscience Research, vol. 84, No. 2, Aug. 1, 2006, pp. 427-433.

Latha et al., "Immunomodulatory and antitumour properties of Psoralea corylifolia seeds," Fitoterapia, vol. 71, No. 3, Jun. 1, 2000, pp. 223-231.

Lee et al., "Phenolic compounds isolated from Psoralea corylifolia inhibit IL-6-induced STAT3 activation," Planta Medica, Jun. 1, 2012, 1 page.

Mizoguchi et al., "Ameliorative effect of traditional Japanese medicine on age-related impairments of working memory and reversal learning in rats," Neuroscience, vol. 177, Dec. 23, 2010, pp. 127-137.

Na et al., "Neuroprotective Effects of Constituents of Eragrostis ferruginea against AB-induced Toxicity in PC12 Cells," Arch Pharm Res. vol. 33, No. 7, pp. 999-1003, Jul. 1, 2010.

Search Report issued on European Application 14826591.1, mailed Jan. 27, 2017.

Tabuchi et al., "Ameliorative effects of yokukansan, a traditional Japanese medicine, on learning and non-cognitive disturbances in the TG2576 mouse model of Alzheimer's disease," Journal of Ethnopharmacology, vol. 122, 2009, pp. 157-162.

Zhao et al., "Fingerprint analysis of Psoralea corlifolia L. by HPLC and LC-MS," Journal of Chromatography, vol. 821, No. 1, Jul. 15, 2005, pp. 67-74.

* cited by examiner

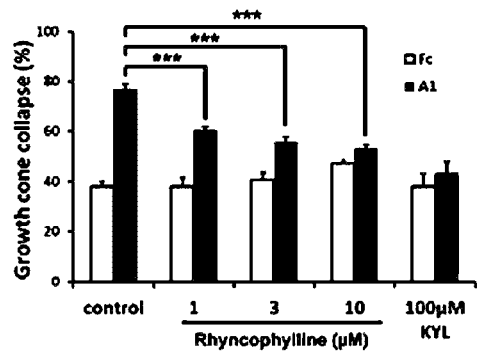
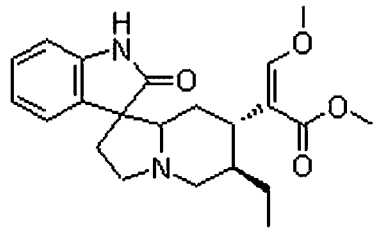
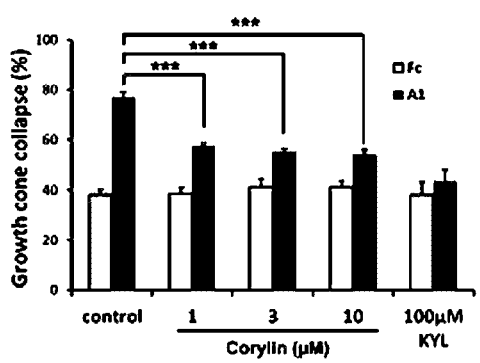
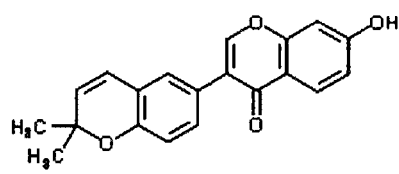
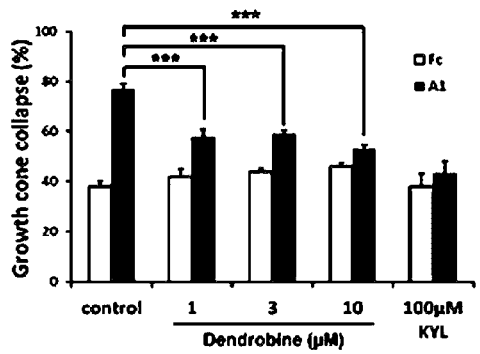
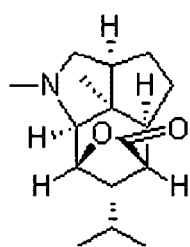
Figure 13

1) Compound #6

Specs ID-Number: AK-918/12943171

N-[3-(2,5-dimethyl-1H-pyrrol-1-yl)phenyl]benzamide

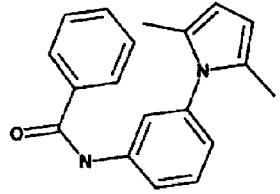

| Molecular formula: | $C_{19} H_{18} N_2 O$ | Molecular weight: | 290.36 |

4) Compound #14

Specs ID-Number: AG-690/12891091

4-(2,5-dimethyl-1H-pyrrol-1-yl)phenyl 4-methylbenzenesulfonate

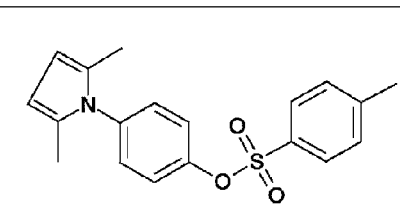

| Molecular formula: | $C_{19} H_{19} N O_3 S$ | Molecular weight: | 341.43 |

6) Compound #21

Specs ID-Number: AG-690/11741363

4-(2,5-dimethyl-1H-pyrrol-1-yl)phenyl 2,4-dichlorobenzoate

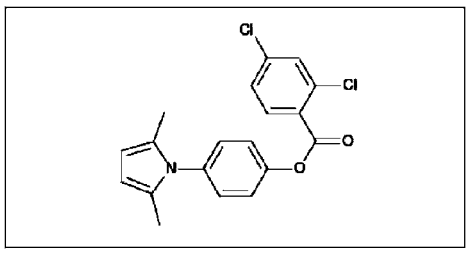

| Molecular formula: | $C_{19} H_{15} Cl_2 N O_2$ | Molecular weight: | 360.24 |

Figure 14

A.
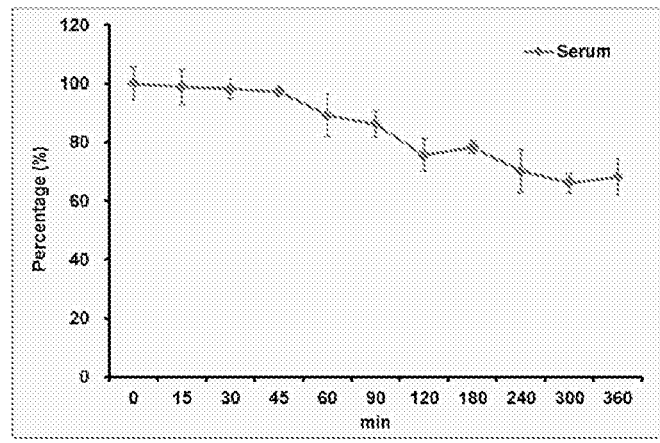
B.
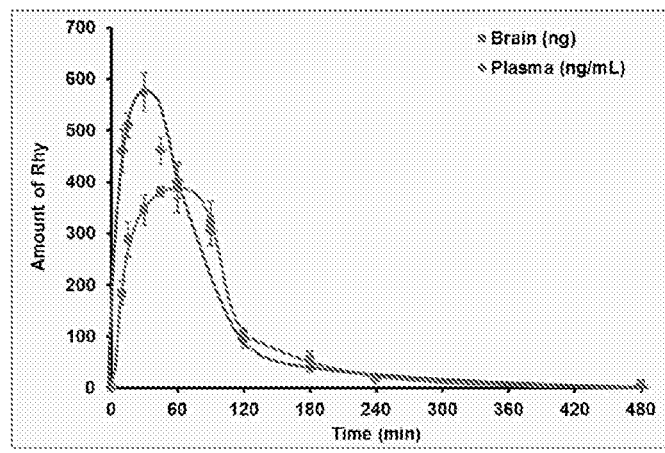
C.
|  | Brain | Plasma |
|---|---|---|
| $T_{max}$ (min) | 55.02 ± 9.18 | 30.84 ± 2.52 |
| $C_{max}$ (ng) | 442.73 ± 27.38 | 583.20 ± 32.86 |
| $t_{1/2}$ (min) | 107.22 ± 27.30 | 81.12 ± 12.06 |
Figure 30

EPHA4 INHIBITORS AS NEUROPROTECTIVE AGENTS

RELATED APPLICATIONS

This application is a U.S. National Phase Application under 35 U.S.C. §371 of International Application No. PCT/CN2014/082386, filed on Jul. 17, 2014, which claims priority to U.S. Provisional Patent Application No. 61/847,432, filed Jul. 17, 2013, the contents of which are incorporated by reference in the entirety for all purposes.

BRIEF SUMMARY OF THE INVENTION

Alzheimer's disease (AD), characterized by cognitive decline, has emerged as a disease of synaptic failure. The present inventors discovered that a receptor tyrosine kinase, EphA4, is important for mediating hippocampal synaptic dysfunctions in AD and that specific inhibition of EphA4 signaling reverses synaptic impairment in AD mouse models. Enhanced EphA4 signaling was observed in the hippocampus of AD transgenic mice, and soluble amyloid-β peptide oligomers (Aβ), which are believed to contribute to synaptic loss in AD, induced EphA4 activation in rat hippocampal slices. Blockade of EphA4-ligand interaction inhibited the Aβ-induced deficits in excitatory synaptic transmission. Furthermore, depletion of EphA4 levels in the CA1 region of hippocampus or interference of EphA4 function was observed to reverse the suppression of hippocampal long-term potentiation (LTP) in AD transgenic mice. Importantly, the present inventors identified a small molecule, rhynchophylline (Rhy), as a candidate EphA4 inhibitor that effectively abolished EphA4-dependent signaling in neurons. In vivo administration of Rhy restored normal LTP and reduced pathology in AD mouse models. In addition, various chemical derivatives of Rhy have been synthesized and shown to possess comparable or enhanced activity as EphA4 inhibitors in comparison to Rhy. Taken together, the findings by the present inventors reveal a previously unknown role of EphA4 in mediating synaptic dysfunctions associated with AD as well as in other neurodegenerative disorders caused or exacerbated by EphA4 signaling. These findings indicate a new therapeutic approach for the treatment of diseases of this nature.

In the first aspect, the present invention provides a novel method for treating a disease or condition that is caused or exacerbated by EphA4 signaling, especially in the case of excessively activated EphA4 signaling. Various diseases and conditions including neurodegenerative disorders are known to involve over-activated EphA4 signaling, for example, amyloid β-induced neurological disorders such as Alzheimer's Disease, spinal cord injury, Parkinson's Disease, head injury (e.g., traumatic brain injury), peripheral nerve regeneration, amyotrophic lateral sclerosis (ALS, often referred to as Lou Gehrig's Disease), stroke, hearing disorders, multiple sclerosis, mood disorders, various types of cancers. Any compound that inhibits EphA4 signaling can be used for the purpose of treating these diseases to alleviate their symptoms. For example, compounds that interfere with and inhibit the specific binding between EphA4 and its ligand can serve as EphA4 signaling inhibitors and therefore can be useful for this particular therapeutic purpose. Often, this type of inhibitors act through competitive binding to either EphA4 or an EphA4 ligand to disrupt and diminish the binding between EphA4 and its ligand. As another example, compounds that can suppress the expression of EphA4 or its ligand, either at RNA level or at protein level, are also useful for the purpose of treating such neurodegenerative diseases by way of reducing EphA4 signaling. In some cases, known EphA4 inhibitors such as rhynchophylline (or Rhy), the KYL peptide (KYLPYWPVLSSL, Murai et al., *Mol. Cell Neurosci.* 2003 December; 24(4): 1000-1011), the APY peptide (APYCVYRRGSWSC) and the VTM peptide (VTMEAINLAFPG), both described in WO2004/028551, Cpd1 and Cpd2 (two isomeric 2,5-dimethylpyrrolyl benzoic acid derivatives described in Noberini et al., *J Biol Chem.* 2008 Oct. 24; 283(43): 29461-29472) can be used for this therapeutic purpose.

Rhynchophylline (Rhy) is described in various literature, see, e.g., Xiong et al., *Hypertension Research* 2013 July; 36(7): 570-579; and Zhou et al., *Fitoterapia* 85 (2013): 125-129. Its chemical name is methyl (7β,16E,20α)-16-(methoxymethylene)-2-oxocorynoxan-17-oate. Its molecular formula is $C_{22}H_{28}N_2O_4$ and its chemical formula is:

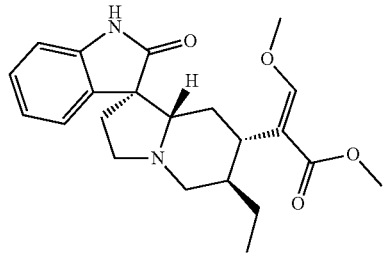 [SMILES: CC[C@H]1CN2CC[C@]3(C(=O)Nc4ccccc43)[C@@H]2C[C@@H]1/C(=C\OC)C(=O)OC]

Rhy is useful as an inhibitor of EphA4 signaling to treat diseases and conditions involving overactive EphA4 signaling. Although isorhynchophylline (IsoRhy) has also been reported as a compound exhibiting certain neuroprotective activity, the present inventors found IsoRhy to be inactive in inhibiting EphA4 signaling. IsoRhy is therefore not intended for use in the present invention.

Besides Rhy, several other inhibitors of EphA4 signaling are known, for instance, the KYL peptide, the APY peptide, and the VTM peptide (Murai et al., supra), Compound 1 and Compound 2 (Noberini et al., supra), as well as unclustered ephrin-A5-Fc and EphA4-Fc (Goldshmit et al., *Plos One* 6, e24636, 2011). Additional small molecule inhibitors of EphA4 signaling are described in Van Linden et al., *Eur. J. Med. Chem.* 2012, 47(1):493-500 and Parmentier-Batteur et al., *J. Neurochem.* 2011, 118(6):1016-1031). While each of these known inhibitors is effective for the use according to the claimed method of this invention due to their shared functional role as EphA4 inhibitors, in some embodiments of this invention, the EphA4 signaling inhibitor used in the claimed method of this invention is not Rhy but another inhibitor. In some cases, the EphA4 signaling inhibitor is not the KYL, APL, or VTM peptide but another inhibitor. In some cases, the EphA4 signaling inhibitor is not Cpd1 or Cpd2 but another inhibitor. In some cases, the EphA4 signaling inhibitor used in the claimed method of this invention is a compound newly identified as EphA4 inhibitor, different from any of the previously known EphA4 inhibitors including those named above. Such new compounds include but are not limited to those described herein, for example, corylin and dendrobine (described in Example 2 of this disclosure), as well as compounds modified from Cpd1 (e.g., compounds 6, 14, and 21 described in Example 3 of this disclosure).

These EphA4 inhibitors, regardless of whether they are previously known or newly identified, are useful for the purpose of treating a disease or condition involving overactive EphA4 signaling, include Alzheimer's disease and others diseases caused by amyloid β-induced neurotoxicity. For the purpose of practicing the present invention, however, any one or any combination of the previously known EphA4 inhibitors may be excluded from the practice scope in some embodiments.

In the second aspect, the present invention provides novel compounds that are chemical derivatives of Rhy possessing at least comparable and often more potent inhibitory activity against EphA4 signaling when compared to Rhy. The novel compounds are generally described as having the structure of Formula I

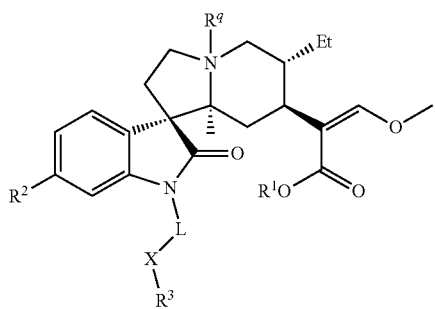

or a pharmaceutically acceptable salt thereof; wherein each $R^1$ is a member independently selected from the group consisting of hydrogen and alkyl; each $R^2$ is a member independently selected from the group consisting of hydrogen and acyl; each $R^q$ is a member independently selected from the group consisting of an electron pair, lower alkyl, allyl, and arylmethyl; L is a linker selected from the group consisting of a bond, an alkylene, and an arylalkylene; X is selected from the group consisting of a bond, —O—, —S—, and —N($R^4$)—; wherein when L is a bond, X is also a bond; $R^3$ is selected from the group consisting of hydrogen, halo, alkyl, alkenyl, alkynyl, aryl, arylalkyl, heteroarylalkyl, acyl, acylalkyl, ($R^4$)$_2$N-alkylene, and

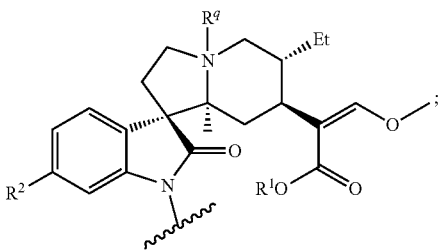

wherein when L is a bond, $R^3$ is selected from the group consisting of hydrogen, aryl, arylalkyl, heteroarylalkyl, acyl, and acylalkyl; wherein when X is —O—, —S—, or —N($R^4$)—, $R^3$ is selected from the group consisting of hydrogen, alkyl, alkenyl, alkynyl, aryl, arylalkyl, heteroarylalkyl, aroylmethyl, acyl, acylalkyl, and ($R^4$)$_2$N-alkylene; and each $R^4$ is independently selected from the group consisting of hydrogen, alkyl, alkenyl, aryl, arylalkyl, heteroarylalkyl, acyl, and acylmethyl. In general, such Rhy derivatives are not Rhy itself or a salt thereof. Exemplary compounds of these Rhy derivatives are provided in Tables 1-3. Chemical derivatives of Rhy useful for the purpose of treating diseases and conditions involving over-active EphA4 signaling are typically synthesized first and then tested in one or more functional assays known in the pertinent field of research or described herein (e.g., ephrin-A1-induced EphA4 cluster assay, EphA4-dependent growth cone collapse assay, or further in APP/PS1 and APP mutant mouse models) in order to verify their inhibitory activity against EphA4 signaling and therapeutic efficacy in treating conditions such as Alzheimer's disease.

In addition, this invention also provides pharmaceutical compositions useful for the purpose of treating diseases or conditions involving overactive EphA4 signaling, especially those involving plaque or aggregate formation (e.g., amyloid β-related neurodegenerative disorders such as Alzheimer's disease), including but not limited to the diseases and conditions named above. In additional to Alzheimer's disease, the pharmaceutical compositions comprising the EphA4 signaling inhibitors (including the Rhy derivatives disclosed herein) may be used to treat diseases and disorders such as amyotrophic lateral sclerosis (ALS), stroke, cancer, and spinal cord injury, all of which have a component of over-active or excessive cellular signaling mediated by EphA4. An amyloid β-related neurodegenerative disorder is a degenerative neurological disorder in which the presence of amyloid plaques contributes to the onset and/or progression of the disorder. One example of such disorders is Alzheimer's Disease. In some embodiments of this invention, motor neuron disorders as conventionally defined are excluded from the class of "amyloid β-related neurodegenerative disorders."

The composition typically comprises an inhibitor for EphA4 signaling as the active ingredient and a pharmaceutically or physiologically acceptable excipient. Often, the EphA4 inhibitors are formulated for preferred mode of delivery, e.g., for oral administration or injection, to a patient in need of such treatment. Furthermore, since EphA4 inhibitors such as corylin and dendrobine are found in certain medicinal plants, extracts of such plants containing the active ingredients including the EphA4 inhibitor(s) may be directly used for therapeutic purposes as described herein.

In some embodiments, the compositions comprise an EphA4 inhibitor that is a novel chemical derivative of Rhy, for example, one set forth in the claims of this application or one provided in Tables 1-3. The EphA4 inhibitors described herein therefore may be used for the manufacture of medicament intended for treating diseases and conditions involving over-active EphA4 signaling, including but not limited to Alzheimer's disease, ALS, Parkinson's Disease, traumatic brain injury, stroke, cancer, and spinal cord injury.

In the third aspect, the present invention provides a method for identifying compounds that can be used as therapeutic agents for treating neurodegenerative diseases (especially an amyloid β-related neurodegenerative disorder such as Alzheimer's Disease) by way of identifying new, previously unknown inhibitors of EphA4 signaling. In some cases, a candidate compound is tested for its ability to interfere with and therefore reduce the binding between EphA4 and its ligand (e.g., an ephrin). Potentially, an inhibitor may be a molecule of any chemical nature, including small molecules, macromolecules (such as polypeptide and polynucleotides), and the like. Typically, the candidate compound being tested for its ability to interrupt EphA4-ligand binding is first placed in an environment where both EphA4 and its ligand are present and under the conditions that are permissible for the specific binding between EphA4 and its ligand. The level of binding between EphA4 and the ligand with the candidate compound present is then determined and compared with the level of binding between EphA4 and its ligand under the same conditions except that the candidate compound is absent (in other words, a "control binding level" of EphA4 and the ligand). If the EphA4-ligand binding level is lower than the control binding level, for example, by at least 10%, 20%, 30%, 40%, 50%, 60%,70%, 75%, 80%, 85%, 90%, 95% or even higher, the binding between EphA4 and its ligand is deemed "inhibited" and the candidate compound is deemed an EphA4 signaling inhibitor, at least preliminarily. Optionally, an additional step of further testing is carried out to verify the compound's function to provide neuroprotection by suppressing EphA4 signaling. For example, an animal model such as the AD mouse model APP/PS1 described in this application may be used to verify whether a compound capable of interrupt EphA4-ligand binding has an effect on improving hippocampal synaptic plasticity inhibited by amyloid plaques, as well as on improving certain features of the AD pathology, e.g., reduced amyloid plaques in the cortex and hippocampus.

As described in this disclosure, for the purpose of screening for small molecule EphA4 inhibitors, one often first performs a molecular docking analysis using a small molecule library. The small molecules that are predicted to bind with EphA4 are selected. In the alternative, small molecules may be first screened and selected for their ability to specifically bind EphA4 in a cell-based or cell-free binding assay format, often in competition against a native ligand for EphA4 such as an ephrin. These selected small molecules are then tested for their ability in inhibiting EphA4 in cellular and animal models. The candidate small molecules (typically at 1 µM to 10 µM) are tested for their ability in inhibiting the EphA4-dependent growth cone collapse using cultured hippocampal neurons. When the small molecules show inhibition on the EphA4-dependent growth cone collapse assay at a dosage-dependent manner, the ability of these small molecules on blocking the ephrin-A dependent autophosphorylation of EphA4 (which reflects the activation status of the receptor) in cultured cortical neurons are examined using Western blot analysis. After it is demonstrate that these small molecules are EphA4 inhibitors in cellular assays, further testing is then performed to determine whether these small molecules are able to reverse the amyloid β-induced reduction of long-term potentiation (LTP; a form of synaptic plasticity) in acute hippocampal organotypic slices. When the results are positive, oral administration of AD mouse models (e.g., APP/PS1 and APP mutant mouse models) with these small molecules are performed. Whether the small molecules can reverse the inhibition of LTP and reduce the pathological hallmarks (amyloid β deposition, astrogliosis and microgliosis) in these AD mouse models is assessed. In addition, biochemical analysis is performed to show that the small molecules bind directly to the extracellular domain of EphA4, but not the other members of the Eph family. The same or similar screening process can be followed for the purpose of identifying EhpA4 inhibitors of any chemical nature.

Another type of EphA4 signaling inhibitors acts by suppressing the expression of EphA4 or its ligand, and such suppression may be at RNA level and/or protein level. Many molecules can fall into this category, for example anti-sense oligonucleotides, microRNAs, or antibodies that specifically target EphA4 transcript (or the transcript of an EphA4 ligand) for hastened degradation can be effective inhibitors of EphA4 signaling. A proposed inhibitor of this nature may be tested by exposing to a cell that expresses EphA4 (or its ligand) for any reduction in EphA4 (or its ligand). Again, such reduction is a reduction of at least 10%, 20%, 30%, 40%, 50%, 60%,70%, 75%, 80%, 85%, 90%, 95% or even higher, when compared to the expression level of EphA4 (or its ligand) under the same conditions but in the absence of the proposed inhibitor. Once a reduction in EphA4 (or its ligand) expression is detected, the proposed inhibitor may be further tested in the same fashion described above to verify its neuroprotective activity.

In the fourth aspect, the present invention provides a kit for use in the treatment of a disease or disorder caused or exacerbated by EphA4 signaling, e.g., an amyloid β-induced neurotoxicity such as Alzheimer's Disease. The kit contains one or more inhibitors of EphA4 signaling, such as by way of disrupting EphA4-ligand binding or by way of suppressing EphA4 or ligand expression (e.g., at the RNA level or at the protein level). The kit often includes multiple containers, each of which contains the EphA4 signaling inhibitor in a daily administration dosage, such that the kit can provide the inhibitor for daily use by a patient during a certain time period. In some cases, the inhibitor is formulated in a pharmaceutical composition suitable for oral administration, or for injection such as intravenous injection, subcutaneous injection, or intramuscular injection. Optionally, an instruction manual directing the user on the administration of the inhibitor is also provided in the kit.

DESCRIPTION OF DRAWINGS

FIG. 13. Corylin and dendrobine exhibit EphA4 inhibition activity. The small molecules inhibitory effect was indicated by their ability to inhibit ephrin-A1 stimulated growth cone collapse.

FIG. 14. Cpd1 (2-hydroxy-4-(2,5-dimethyl-1-pyrrolyl) benzoic acid) chemical derivatives: compounds 6, 14, and 21.

FIG. 30A: Rhy remained relatively stable in mouse serum after 6-h incubation of the serum. Rhy was detected by UPLC-MS/MS analysis. Data is represented as percentage of Rhy detected at various time points compared to value at $t_0$ (mean±SEM; n=4 mice). FIG. 30B: Pharmacokinetics of Rhy in mouse plasma and brain after oral administration. Data is represented as amount of Rhy in plasma (ng/mL) or per brain after administration (mean±SEM). Blood and perfused whole brains were collected at different time points after single administration, n=6 animals per time point (11 time points). FIG. 30C: Pharmacokinetic parameters of Rhy in mouse brain and plasma.

DETAILED DESCRIPTION OF INVENTION

Figure 1:
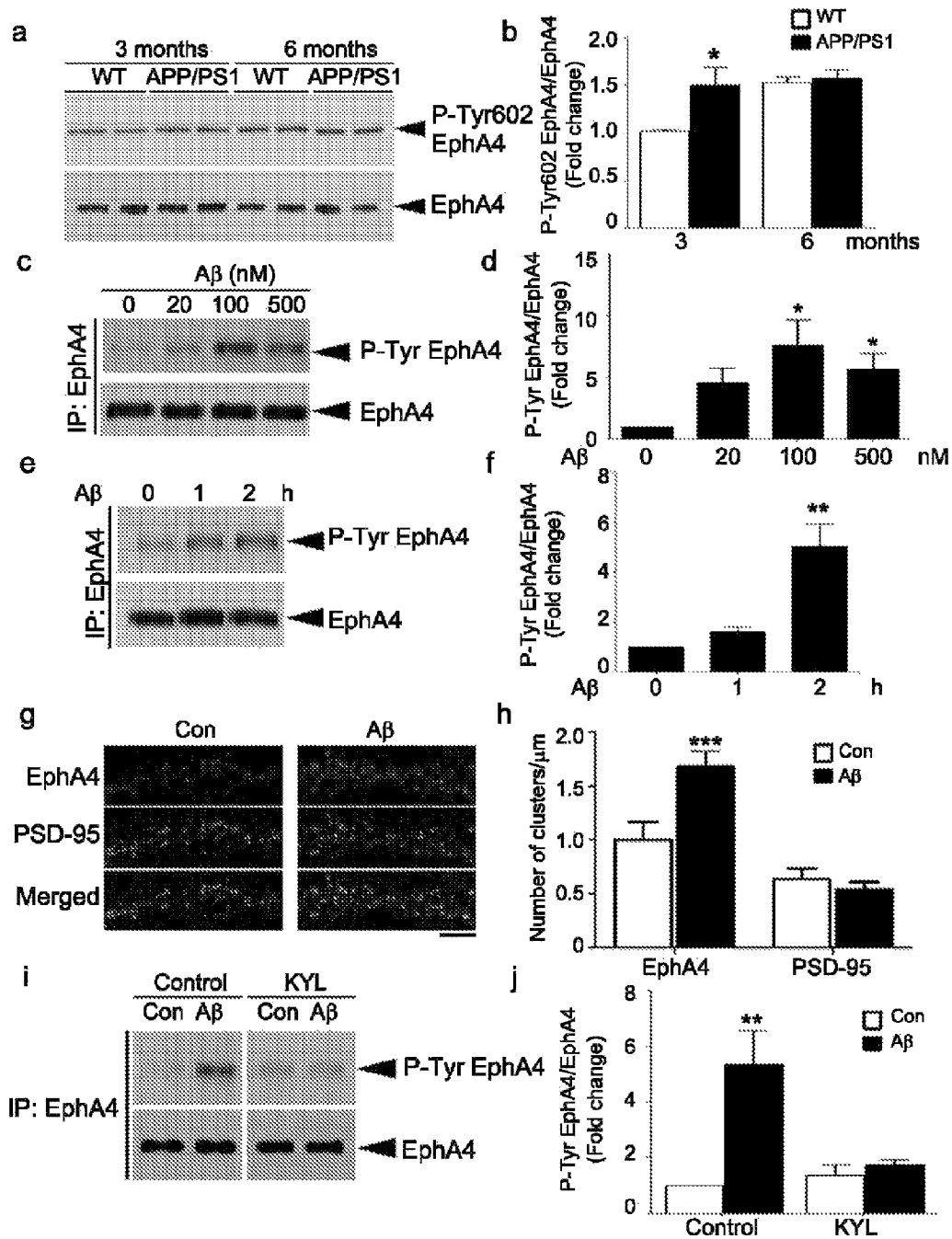
FIG. 1. Aβ-stimulates the activation of EphA4 signaling. (a & b) Western blot of Tyr602 EphA4 phosphorylation (P-Tyr602 EphA4) and total EphA4 level in hippocampal synaptosomal fractions of WT and APP/PS1 mice at 3 and 6 months. Quantification of P-Tyr602 EphA4 in WT and APP/PS1 mice normalized to EphA4 protein (*$p<0.01$, one-way ANOVA, Student's Newman test; n=4 for all conditions except n=3 for WT at 3 months of age). (c-f) Aβ increased EphA4 tyrosine phosphorylation. (c, d) Acute rat hippocampal slices were treated with 20, 100 or 500 nM Aβ for 2 h or 500 nM for various periods as indicated (e, f). EphA4 was immunoprecipitated from total lysate and then subjected to western blotting for P-Tyr EphA4. (d, f) Quantification of P-Tyr EphA4 upon Aβ treatment normalized to EphA4 (d) *$p<0.05$ vs. 0 nM, one-way ANOVA, Student's Newman test; n=6 for 0 nM, n=5 for 20 and 100 nM, 7 for 500 nM. (f) $p<0.05$ vs. 0 h, one-way ANOVA, Student's Newman test; n=3. (g, h) Aβ increased the number of EphA4 clusters. Cultured hippocampal neurons (25-28 DIV) were treated with Aβ for 4 h. Aβ increased EphA4 clustering (postsynaptic regions were stained with PSD-95 antibody). Representative images (g). Scale bar=10 µm. Quantification analysis of EphA4 or PSD-95 clusters (h) (*$p<0.001$, Student's t-test). (i, j) Blockade of the EphA4-ligand interaction abolished the Aβ-stimulated activation of EphA4. Acute rat hippocampal slices were pretreated with KYL peptide for 0.5 h followed by Aβ for 2 h. (i) EphA4 was immunoprecipitated and subjected to western blot analysis for P-Tyr EphA4. (j) The fold change of EphA4 activation is shown (P-Tyr EphA4/EphA4; right panel). *$p<0.01$; one-way ANOVA followed by the Student-Newman-Keuls test (n=3).

The examples of this application are provided by way of illustration only and not by way of limitation. Those of skill in the art will readily recognize a variety of non-critical parameters that could be changed or modified to yield essentially the same or similar results.

A. INTRODUCTION

Alzheimer's disease (AD) is the most common form of dementia and involves accumulation of amyloid plaques and neurofibrillary tangles in brains. Cognitive impairment, regarded as an early manifestation of AD, is believed to be attributable to disruptions of synaptic functions. The degree of synaptic loss and alterations correlate with the severity of memory deficit in AD[1]. Soluble amyloid-β peptide oligomers (Aβ), which are generated by the proteolytic cleavage of amyloid precursor protein (APP), are believed to be major causative agents of synaptic impairment during AD progression[2,3]. Thus, reversal of Aβ-induced synaptic deficit is considered a promising therapeutic approach for treating cognitive impairment in AD[4].

Aβ binds to synaptic sites[5], resulting in synaptic loss and reduction of glutamatergic synaptic transmission[6-8]. Aβ also rapidly impairs synaptic plasticity in the hippocampus, including the inhibition of long-term potentiation (LTP)[2] or facilitation of long-term depression (LTD)[9], which are major cellular mechanisms associated with learning and memory. Synaptic defects triggered by Aβ are mediated by the internalization and downregulation of both N-methyl-D-aspartate (NMDA)- and 2-amino-3-(3-hydroxy-5-methyl-isoxazol-4-yl) propanoic acid (AMPA)-type glutamate receptors[10-12], together with a reduction of dendritic spines[8], where excitatory synapses are located. Identifying molecular targets and understanding the cellular mechanisms that mediate the action of Aβ in synaptic depression in AD are therefore crucial for the development of therapeutic interventions for AD. Interestingly, various cell surface receptors such as α7-nicotinic acetylcholine receptors[12], metabotropic glutamate receptors[13], insulin receptors[14], and the receptor tyrosine kinase, EphB2[15], have been reported to mediate the action of Aβ at synapses.

The erythropoietin-producing hepatocellular (Eph) family of receptor tyrosine kinases is important for the regulation of synapse development and synaptic plasticity[16-18]. Whereas EphB enhances synapse development through its interaction with NMDA receptors[19,20], EphA4, which is mainly expressed in the adult hippocampus, acts as a negative regulator of neurotransmission and hippocampal synaptic plasticity[21]. Activation of EphA4 by its ligands, ephrins, triggers forward signaling through the induction of receptor clustering and autophosphorylation[22]. This leads to the retraction of dendritic spines through cyclin-dependent kinase 5 (Cdk5)-dependent RhoA activation and reduction of cell adhesion[23-25]. EphA4 also causes the removal of synaptic and surface AMPA receptors during homeostatic plasticity—a form of plasticity that ensures neuronal output is within the optimal range, thus providing stability for the neuronal network[26,27]. Interestingly, AD patients with only mild cognitive deficits exhibit deregulated EphB and EphA4 expression[28]. Given that EphA4 activation results in dendritic spine loss and reduction of AMPA receptor abundance[21,27,29], representing two potential mechanisms that underlie synaptic dysfunctions in AD[8,10], the present inventors have investigated the possible link between EphA4 signaling and Aβ-induced synaptic failure.

The inventors demonstrate that EphA4 mediates the impairment of synaptic plasticity induced by Aβ. Depletion of postsynaptic EphA4 or disrupting the interaction between EphA4 and its ligands reversed the synaptic deficits after Aβ treatment and in AD mouse models. Importantly, molecular docking analysis identified a small molecule, rhynchophylline (Rhy), from a traditional Chinese medicine library as a candidate EphA4 inhibitor. Rhy rescued the impaired neurotransmission induced by Aβ and LTP defects in the AD mouse models. Thus, the inventors' findings have not only revealed an important role of EphA4 in the pathogenesis of AD but also identified a small molecule EphA4 inhibitor that can be used as a therapeutic agent for the treatment of AD or other diseases/conditions involving EphA4 signaling, for example caused by or exacerbated by excessive EphA4 activation and signaling.

B. EphA4 INHIBITORS

Besides previously known compounds being identified in this application for the first time as EphA4 inhibitors, the present inventors have also provided novel inhibitors of EphA4, for example, novel chemical derivatives of Rhy. An exemplary list of such derivatives is presented in Tables 1-3.

These novel derivatives are first chemically synthesized using Rhy as a starting material. For example, a derivative is generally a compound of Formula I:

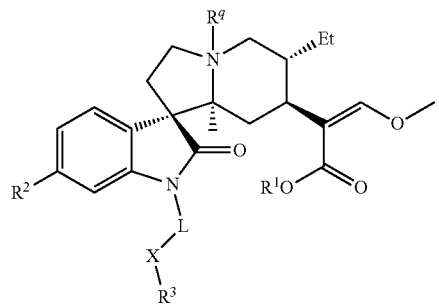

or a pharmaceutically acceptable salt thereof; wherein
each $R^1$ is a member independently selected from the group consisting of hydrogen and alkyl;
each $R^2$ is a member independently selected from the group consisting of hydrogen and acyl;
each $R^q$ is a member independently selected from the group consisting of an electron pair, lower alkyl, allyl, and arylmethyl.
L is a linker selected from the group consisting of a bond, an alkylene, and an arylalkylene;
X is selected from the group consisting of a bond, —O—, —S—, and —N($R^4$)—; wherein when L is a bond, X is also a bond;
$R^3$ is selected from the group consisting of hydrogen, halo, alkyl, alkenyl, alkynyl, aryl, arylalkyl, heteroarylalkyl, acyl, acylalkyl, ($R^4$)$_2$N-alkylene, and

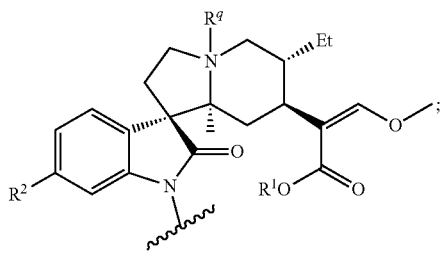

wherein when L is a bond, $R^3$ is selected from the group consisting of hydrogen, aryl, arylalkyl, heteroarylalkyl, acyl, and acylalkyl;
wherein when X is —O—, —S—, or —N($R^4$)—, $R^3$ is selected from the group consisting of hydrogen, alkyl, alkenyl, alkynyl, aryl, arylalkyl, heteroarylalkyl, aroylmethyl, acyl, acylalkyl, and ($R^4$)$_2$N-alkylene; and
each $R^4$ is independently selected from the group consisting of hydrogen, alkyl, alkenyl, aryl, arylalkyl, heteroarylalkyl, acyl, and acylmethyl. In accordance with the definition of "derivative," the derivative is typically not rhynchophylline or a salt thereof.

Chemical synthesis of these derivatives is generally carried out by joining a chosen substitute group with the main structure of Rhy at the $N^1$ site via a suitable linker. Exemplary synthetic schemes are provided in the Examples of this disclosure. As it is understood that an appropriate linker length is relevant to functionality of the resultant Rhy derivative as an EphA4 inhibitor, besides the particular linkers used in the exemplary Rhy derivatives identified in Tables 1-3, alternative linkers can be used in the process of synthesizing Rhy derivatives that possess inhibitory activity against EphA4 signaling at a level comparable or superior to Rhy. For example, a linker of a saturated chain of 3-12, 5-10, 5-9, or 6-8 (e.g., 6 or 7) carbons is typically effective in generating a functional Rhy derivative when used to join a substitute group shown in Tables 1-3 at the $N^1$ site of Rhy. An alternative linker that provides comparable spacing between the substitute group and the main structure of Rhy, for example, a linker length between 1 to 31 Å, preferably 4 to 24 Å, more preferably 7 to 18 Å, is suitable for use in the present invention for producing functional Rhy derivatives as EphA4 inhibitors. In general, any linker with varying chemical and structural features may be used in the synthesis of Rhy derivatives, so long as the resultant derivatives are active EphA4 inhibitors, which may be verified in functional assays known in the pertinent research field and/or described herein.

Once a chemical derivative of Rhy is obtained, its potential inhibitory activity against EphA4 signaling is then tested in one or more assays known in the research field or described (e.g., ephrin-A1-induced EphA4 cluster assay, EphA4-dependent growth cone collapse assay) for verification. In most cases, when a negative effect on the level of EphA4-mediated signaling by at least 10%, preferably at least 20%, 30%, 40%, 50%, 60%, 70%, 80%, 90%, or an even higher percentage, is detected at the presence of a candidate compound when compared with the level of signaling in the absence of the candidate compound, the compound is deemed an inhibitor. The functional assays are often performed including Rhy as a positive control. If a derivative's inhibitory effect is within +/−10% of the inhibitory effect of Rhy, the derivative is deemed to possess comparable activity to Rhy as an EphA4 inhibitor. On the other hand, when a derivative's inhibitory effect is at least 20% greater than that of Rhy, e.g., at least 30%, 40%, 50%, 60%, 70%, 80%, 90% or more than that of Rhy, the derivative is deemed to possess enhanced activity to Rhy as an EphA4 inhibitor.

The terms "a," "an," or "the" as used herein not only include aspects with one member, but also include aspects with more than one member. For example, an embodiment of a method of treatment that comprises using a compound set forth in claim 1 would include an aspect in which the method comprises using two or more compounds set forth in claim 1.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "about" is applied to describe the beginning of a numerical range, it applies to both ends of the range. Thus, "from about 50 to 250 mg" is equivalent to "from about 50 to about 250 mg." When "about" is applied to describe the first value of a set of values, it applies to all values in that set. Thus, "about 100, 150, or 200 mg," is equivalent to "about 100 mg, about 150 mg, or about 200 mg." However, when the modifier "about" is applied to describe only the end of the range or only a later value in the set of values, it applies only to that value or that end of the range. Thus, the range "about 5 to 9" is the same as "about 5 to about 9," but the range "5 to about 9" is not.

"Acyl" as used herein includes an alkanoyl, alkenoyl, aroyl, heterocycloyl, heteroaroyl, or biotinyl group as defined herein. Representative acyl groups include acetyl, benzoyl, 4-methoxybenzoyl, nicotinoyl, cinnamoyl, biotinyl, and the like.

"Acylalkyl" as used herein includes an alkyl group (preferably, a methyl group) with an acyl group substituent. Representative acylalkyl include benzoylmethyl, 3-phenylacryloyl)methyl, (4-methoxybenzoyl)methyl, and the like.

"Alkanoyl" as used herein includes an alkyl-C(O)— group wherein the alkyl group is as defined herein. Representative alkanoyl groups include acetyl, ethanoyl, and the like.

"Alkenoyl" as used herein includes an alkenyl-C(O)— group wherein the alkenyl group is as defined herein. Representative alkenoyl groups include cinnamoyl, acryloyl, methacryloyl, 3-phenylacryloyl, 3-(4-methoxyphenyl) acryloyl, and the like.

"Alkenyl" as used herein includes a straight or branched aliphatic hydrocarbon group of 2 to about 15 carbon atoms that contains at least one carbon-carbon double bond, which may be the cis- or the trans-stereoisomer. Preferred alkenyl groups have 2 to about 12 carbon atoms and may include an aryl substituent conjugated to the alkene (e.g., trans-2-phenylethenyl; cis-3-phenylprop-2-enyl; cis-2-phenylethenyl; trans-2-(4-methoxyphenyl)ethenyl; cinnamyl). "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, and the like.

"Alkenylene" as used herein includes a straight or branched bivalent carbon chain containing at least one carbon-carbon double or triple bond. Preferred alkenylene groups include from 4 to about 12 carbons in the chain, and more preferred alkenylene groups include from 5 to about 9, or 6, 7, or 8, carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH═CH—, —CH$_2$—CH═CH—, —C(CH$_3$)═CH—, —CH$_2$CH═CHCH$_2$—, ethynylene, propynylene, n-hex-2-ynylene, trans-oct-4-enylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 10 or 1 to 6 carbon atoms in the chain. "Branched-chain" as used herein includes that one or more lower alkyl groups such as methyl, ethyl or propyl are attached to a linear alkyl chain. "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

"Alkylene" as used herein includes a straight or branched bivalent carbon chain of 2 to about 12 carbon atoms in the bivalent chain itself. Preferred alkylene groups are the mid-range alkylene groups having 3 to 10, 3 to 9, 5 to 9, or 6 to 8, carbon atoms in the bivalent hydrogen chain itself (i.e., any of 3, 4, 5, 6, 7, 8, 9, or 10 carbons, such as —CH$_2$— groups). In some embodiments, a carbon atom in the bivalent chain is replaced by a heteroatom, such as in a polyalkylene glycol linker (e.g., —(CH$_2$CH$_2$O)$_n$CH$_2$CH$_2$—, in which n is from 1 to 4). Preferably, an alkylene group is a straight-chain hydrocarbon. Representative alkylene groups include 1,6-hexylene, 1,7-heptalene, 1,8-octalene, and the like.

"Alkynyl" as used herein includes a straight or branched aliphatic hydrocarbon group of 2 to about 15 carbon atoms that contains at least one carbon-carbon triple bond. Preferred alkynyl groups have 2 to about 12 carbon atoms. More preferred alkynyl groups contain 2 to about 6 carbon atoms. "Lower alkynyl" as used herein includes alkynyl of 2 to about 6 carbon atoms. Representative alkynyl groups include propynyl, 2-butynyl, 3-methylbutynyl, n-pentynyl, heptynyl, and the like.

"Amino" as used herein includes a group of formula Y$^1$Y$^2$N— wherein Y$^1$ and Y$^2$ are independently hydrogen, acyl, aryl, or alkyl; or Y$^1$ and Y$^2$, together with the nitrogen through which Y$_1$ and Y$_2$ are linked, join to form a 4- to 7-membered azaheterocyclyl group (e.g., piperidinyl). In some embodiments, when Y$_1$ and Y$_2$ are independently hydrogen or alkyl, an additional substituent can be added to the nitrogen, making a quaternary ammonium ion. Representative amino groups include primary amino (H$_2$N—), methylamino, dimethylamino, diethylamino, tritylamino, pyrrolidinyl, and the like. Preferably, "amino" is an —NRR' group where R and R' are members independently selected from the group consisting of H and alkyl. Preferably, at least one of R and R' is H. Alternatively, "amino" is preferably an azaheterocyclyl group (e.g., pyrrolidinyl).

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like.

"Aroyl" as used herein includes an aryl-CO— group wherein aryl is defined herein. Representative aroyl include benzoyl, 4-methoxybenzoyl, 5-methoxy-2-nitrobenzoyl, 2-iodobenzoyl, 3,4-dimethoxybenzoyl, 4-hydroxybenzoyl, 4-(benzyloxy)benzoxyl, 2-iodo-4-bromobenzoyl, and the like.

"Aryl" as used herein includes an aromatic monocyclic or multicyclic ring system of 6 to about 14 carbon atoms, preferably of 6 to about 10 carbon atoms. In a preferred embodiment, the aryl group is unsubstituted (e.g., phenyl) or substituted with from 1 to 3 substituents selected from the group including halo, alkyl, alkoxy, arylalkyloxy, hydroxyl, benzoyl, nitro, and the like. Representative aryl groups include phenyl, naphthyl, 3,4-dimethoxyphenyl, 4-hydroxyphenyl, 4-benzyloxyphenyl, 5-methoxy-2-nitrophenyl, 2-iodophenyl, and 2-iodo-4-bromophenyl.

"Arylalkyl" as used herein includes an alkyl group with an aryl substituent. Preferably, an arylalkyl group is an arylmethyl group, such as benzyl. Representative arylalkyl groups include benzyl, 2-phenylbenzyl, 3-chlorobenzyl, 3-methoxybenzyl, 4-tert-butylbenzyl, 4-methylbenzyl, 3,4-dimethoxybenzyl, 3-benzoylbenzyl, 4-bromobenzyl, 4-benzoylbenzyl, 2,6-dichlorobenzyl, and the like.

"Arylalkylene" as used herein includes an alkylene chain that includes an aryl group. Representative arylene groups include —CH$_2$(1,4-C$_6$H$_4$)CH$_2$— and the like.

"Biotinyl" as used herein includes a substituent of the structure:

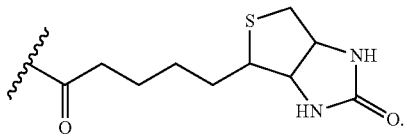 [SMILES: *C(=O)CCCCC1SCC2NC(=O)NC21]

Preferably, a biotinyl substituent has the same stereochemistry as natural biotin.

"Geminal" substituents as used herein includes two or more substituents that are directly attached to the same atom. An example is 3,3-dimethyl substitution on a cyclohexyl or spirocyclohexyl ring.

"Halo" or "halogen" as used herein includes fluoro, chloro, bromo, or iodo.

"Heteroatom" as used herein includes an atom other than carbon or hydrogen. Representative heteroatoms include O, S, and N; preferably, O and N. The nitrogen or sulfur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., —C$_1$-C$_9$ alkylene-O—C$_1$-C$_9$ alkylene-). In some embodiments, a heteroatom is further substituted with an acyl, alkyl, aryl, cycloalkyl, heterocyclyl, or heteroaryl group (e.g., —N(Me)-; —N(Ac)-).

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Heterocyclyl" as used herein includes a non-aromatic saturated monocyclic or multicyclic ring system of about 3 to about 10 ring atoms, preferably about 5 to about 10 ring atoms, in which one or more of the atoms in the ring system is an element or elements other than carbon, e.g., nitrogen, oxygen or sulfur. Preferred heterocyclyl groups contain about 5 to about 6 ring atoms. A heterocyclyl group optionally comprises at least one sp$^2$-hybridized atom (e.g., a ring incorporating an carbonyl, endocyclic olefin, or exocyclic olefin). The prefix "aza," "oxa," or "thia" before heterocyclyl means that at least a nitrogen, oxygen or sulfur atom respectively is present as a ring atom. The nitrogen or sulfur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" as used herein includes an aromatic monocyclic or multicyclic ring system of about 5 to about 14 ring atoms, preferably about 5 to about 14 ring atoms, in which at least one of the atoms in the ring system is an element other than carbon, i.e., nitrogen, oxygen or sulfur. Preferred heteroaryls contain about 5 to about 6 ring atoms. The prefix "aza," "oxa," or "thia" before heteroaryl means that at least a nitrogen, oxygen or sulfur atom respectively is present as a ring atom. A nitrogen atom of a heteroaryl is optionally oxidized to the corresponding N-oxide. Representative heteroaryls include 2-pyridyl, 3-pyridyl, 4-pyridyl, 3-quinoxalin-2(1H)-onyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroarylalkyl" as used herein includes an alkyl group with a heteroaryl group substituent. Preferably, an heteroarylalkyl group is an heteroarylmethyl group, such as 2-pyridylmethyl. Representative heteroarylalkyl groups include 2-pyridylmethyl, 3-pyridylmethyl, 4-pyridylmethyl, and (3-quinoxalin-2(1H)-onyl)methyl.

When any two substituent groups or any two instances of the same substituent group are "independently selected" from a list of alternatives, they may be the same or different. For example, if $R^a$ and $R^b$ are independently selected from the group consisting of methyl, ethyl, benzyl, and propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be benzyl (or any other substituents taken from the group). Alternatively, both $R^a$ and the first $R^b$ could be ethyl, while the second $R^b$ could be benzyl (i.e., some pairs of substituent groups may be the same, while other pairs may be different).

"Oxo" as used herein includes a group of formula >C=O (i.e., a carbonyl group —C(O)—).

"Spirocycloalkyl" as used herein includes a cycloalkyl in which geminal substituents on a carbon atom are replaced to form a 1,1-substituted ring; a spirocycloalkynyl is a cycloalkynyl in which geminal substituents on a carbon atom are replaced to form a 1,1-substituted ring.

In general, the unit prefix "u" as used herein is equivalent to "μ" or "micro." For example, "ul" is equivalent to "μl" or "microliters."

C. USE OF EphA4 INHIBITORS

EphA4 inhibitors described in this application are useful for treating a variety of diseases and conditions including neurodegenerative disorders involving over-activated EphA4 signaling, for example, amyloid β-induced neurological disorders such as Alzheimer's Disease, spinal cord injury, Parkinson's Disease, head injury (e.g., traumatic brain injury), peripheral nerve regeneration, amyotrophic lateral sclerosis (ALS), stroke, hearing disorders, multiple sclerosis, mood disorders, and cancers. In particular, they are useful, when administered in an effective amount to a patient in need thereof, for the treatment of stroke, ALS, spinal cord injury, and cancers. The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the nature of the therapeutic agent, the manner of administration, and the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The EphA4 receptor is indicated as a therapeutic target for a number of ailments. For example, the EphA4 signal pathway is linked to the apoptotic cell death resulting from ischemia. The expression of ephrinA3 and EphA4 is significantly increased in the hippocampus following transient forebrain ischemia. Inhibition of EphA4, however, reduces apoptotic neuronal cell death, thus indicating that EphA4 signalling is involved in apoptosis after ischemia (Li et al., *Neurosci Lett.* 518(2):92-5, 2012). Furthermore, a recent study shows that pharmacological inhibition of the EphA4 signaling cascade affects functional recovery, and more specifically, improves motor function after ischemic stroke (Lemmens et al., *Hum Mol Genet.* 22(11):2214-20, 2013).

EphA4 inhibition also rescues neurodegeneration in amyotrophic lateral sclerosis (ALS), a fatal neurodegenerative disease characterized by the progressive degeneration of motor neurons. It has been shown that motor neurons that are most susceptible to degeneration in ALS express higher levels of EphA4. Furthermore, an inverse correlation between EPHA4 expression and disease onset and survival, has been observed in ALS patients. Moreover, EphA4 knockdown rescues axonopathy induced by expression of mutant TAR DNA-binding protein 43, another protein that causes familial ALS. These findings indicate that EphA4 modulates motor neuron degeneration and disease progression in ALS, and highlights the use of EphA4 inhibition as a therapeutic strategy in ALS (Faruqi, *Nat Rev Drug Discov.* 11(10):747, 2012; Van Hoecke et al., *Nat Med.* 18(9):1418-22, 2012).

EphA4 inhibition also shows promising therapeutic potential in spinal cord injury (SCI). Individuals with SCI are often paralyzed with little chance of regaining loss of function due to limited ability of axons to grow and regenerate. However, EphA4 has recently been implicated in axonal inhibition and astrocytic gliosis. Mice lacking the EphA4 gene exhibit less gliosis and significantly reduced glial scars in their lesioned cords after spinal cord hemisection, and further, neurological outcome in EphA4$^{-/-}$ mice is dramatically improved compared to wild-type controls (Goldshmit et al., *J Neurosci.* 24(45):10064-73, 2004). Furthermore, administration of an EphA4 inhibitor has demonstrated significant recovery in locomotor function after SCI in an animal model of SCI (Spanevello et al., *J Neurotrauma.* 30(12):1023-34, 2013).

EphA4 is also implicated in cancer. The receptor is upregulated in various human cancers such as gastric cancer (Oki et al., *World J Gastroenterol.* 14:5650-5656, 2008; Miyazaki et al., *BMC Clin Pathol.* 13:19, 2013), colorectal cancer (Oshima et al., *Int J Oncol.* 33:573-577, 2008), and pancreatic cancer (Liu et al., *Oncol Lett.* 7(6):2165-2169, 2014). High expression of EphA4 is correlated with tumor progression, including the invasion, pathological stage and distant metastasis (Miyazaki et al., *BMC Clin Pathol.* 13:19, 2013). For example, EphA4 expression in brain tumors has been shown to be 4-fold higher than in normal brain tissue. Furthermore, EphA4 also plays an important role in malignant phenotypes of glioblastoma by promoting the proliferation and migration of glioma cells (Fukai et al., *Mol Cancer Ther.* 7(9):2768-78, 2008). Thus, EphA4 inhibitors are important therapeutic agents in anticancer treatment strategies.

Furthermore, EphA4 plays a role in adult neurogenesis, which is a process of producing functional neurons from proliferating cells called neural progenitor cells in the adult brain. Both in vivo and in vitro studies suggest that this process can be modulated by various environmental factors. For instance, enriched environment, exercise and learning, can stimulate adult neurogenesis while chronic stress or aging affect in the opposite way. Accumulating evidence further suggests that the etiology of depression is highly related to defective adult neurogenesis in hippocampus (Masi and Brovedani, 2011 *CNS Drugs* 25, 913-31; Lee et al., 2013 *Curr Top Behav Neurosci* 14, 153-79). Chronic stress causes suppression of adult neurogenesis, probably due to the elevated level of glucocorticoid release. Additionally, antidepressant treatment (e.g., imipramine and fluoxetine) are shown to upregulate neurogenesis in the adult brain, which further support the notion that adult neurogenesis is a core factor in the pathology of depression (Lee et al., 2013 *Curr Top Behav Neurosci* 14, 153-79; Fang et al. 2013 *Neuron* 79, 665-79; David et al., 2009 *Neuron* 62, 479-93). Agents that can stimulate adult neurogenesis provide a new therapeutic strategy for treating depression. In their study, the present inventors discovered that oral administration of Rhy increases adult neurogenesis in mouse hippocampus and thus can be used for depression or psychiatric disorder treatment. The novel chemical derivatives of Rhy that have EphA4 inhibitor activity described herein are therefore also useful for treating neurological/psychiatric disorders such as anxiety and depression.

Multiple sclerosis (MS) is another disease that may be treated by the EphA4 inhibitors described herein. MS is the most common disabling neurologic disease of young adults (Hauser and Oksenberg 2006 *Neuron* 52(1):61-76). It is an autoimmune disease of the central nervous system with widespread focal lesions of primary demyelination leading to variable axonal, neuronal and astroglia injury (Lassmann 2013 *Exp Neurol.* 50014-4886(13)00361-0). Demyelination, the hallmark of MS, disrupts neuronal communication resulting in a wide range of symptoms (Hernandez-Pedro et al. 2013 *Clin Dev Immunol.* 413-465). The initial inflammatory cascade is thought to originate from the activation of resident cells in the CNS, leading to tissue destruction, demyelination, and progressive neurological dysfunction (Hernandez-Pedro et al. 2013 *Clin Dev Immunol.* 413-465). Ephrins and Ephs not only play important roles such as synaptic plasticity and neural stem cell function, they are also involved in immunologic functions such as in thymic development and T/B-cell signaling (Sobel 2005 *Brain Pathol.* 15(1):35-45; Muñoz et al. 2002 *J Immunol.* 169(1): 177-845). Blockade of EphA4 inhibited wound closure and reduced the accumulation of reactive astrocytes in the scratch wound model (Parmentier-Batteur et al. 2011 *J Neurochem.* 118(6):1016-31). Aberrant ephrin/Eph expression is involved in the immunopathogenesis of lesions and in neuronal injury in multiple sclerosis (MS) (Sobel 2005 *Brain Pathol.* 15(1):35-45). In another study in human MS patients, an increase in EphA4 protein was found in active MS lesions relative to those in chronic MS lesions (Parmentier-Batteur et al. 2011 *J Neurochem.* 118(6):1016-31). Taken together, these studies support a role for the activation of EphA4 in the development of the damage after acute CNS injury, including MS, and that inhibition of EphA4 (e.g., via the action of a EphA4 inhibitor, such as a chemical derivative of Rhy described herein) is a therapeutic strategy that promotes CNS functional recovery in MS and other neurodegenerative diseases.

A pharmaceutical composition made for the use of treating diseases or conditions involving over-active EphA4 signaling typically comprises one EphA4 inhibitor (e.g., any one of the inhibitors identified herein) as the active ingredient and a pharmaceutically/physiologically acceptable excipient or carrier. Such composition may be specifically formulated for the intended route of administration to the patients, for example, via oral administration or injection. The EphA4 inhibitors are also useful for the purpose of manufacturing medicament for the treatment of relevant diseases as described in this application.

D. PHARMACEUTICAL COMPOSITIONS AND ADMINISTRATION

The present invention also provides pharmaceutical compositions or physiological compositions comprising an effective amount of a compound that inhibits EphA4-mediated signaling and therefore provide the intended benefits in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The preferred routes of administering the pharmaceutical compositions are local delivery to an organ or tissue suffering from a condition exacerbated by EphA4-mediated signaling at daily doses of about 0.01-2500 mg, preferably 2.5-500 mg, of an EphA4 inhibitor for a 70 kg adult human per day. The appropriate dose may be administered in a single daily dose or as divided doses presented at appropriate intervals, for example as two, three, four, or more subdoses per day.

For preparing pharmaceutical compositions containing an EphA4 inhibitor such as those shown in Tables 1-3, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an EphA4 inhibitor in Tables 1-3. In tablets, the active ingredient (an inhibitor of EphA4 signaling) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of EphA4-mediated signaling. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an EphA4 inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an EphA4 inhibitor such as one found in Tables 1-3) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an EphA4 signaling inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing an EphA4 inhibitor can be administered for prophylactic and/or therapeutic treatments. In therapeutic applications, compositions are administered to a patient already suffering from a condition that may be exacerbated by the EphA4-mediated cellular signaling in an amount sufficient to prevent, cure, reverse, or at least partially slow or arrest the symptoms of the condition and its complications, such as the onset, progression, and metastasis of certain types of cancer. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing an EphA4 inhibitor are administered to a patient susceptible to or otherwise at risk of developing a disease or condition in which excessive EphA4-mediated signaling is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of an EphA4 inhibitor sufficient to effectively inhibit cellular signaling mediated by EphA4 in the patient, either therapeutically or prophylatically.

E. KITS

The invention also provides kits for inhibiting EphA4 signaling and therefore for treating cancer according to the method of the present invention. The kits typically include a container that contains (1) a pharmaceutical composition having an effective amount of an inhibitor of EphA4-mediated signaling (for instance, a compound identified in Tables 1-3) and (2) informational material containing instructions on how to dispense the pharmaceutical composition, including description of the type of patients who may be treated (e.g., patients suffering from Alzheimer's Disease, ALS, stroke, or various types of cancer with excessive EphA4 signaling), the schedule (e.g., dose and frequency) and route of administration, and the like.

F. EXAMPLES

Example 1

Blocking EphA4-Mediated Signaling Alleviates Aβ-Induced Impairment

Figure 7:
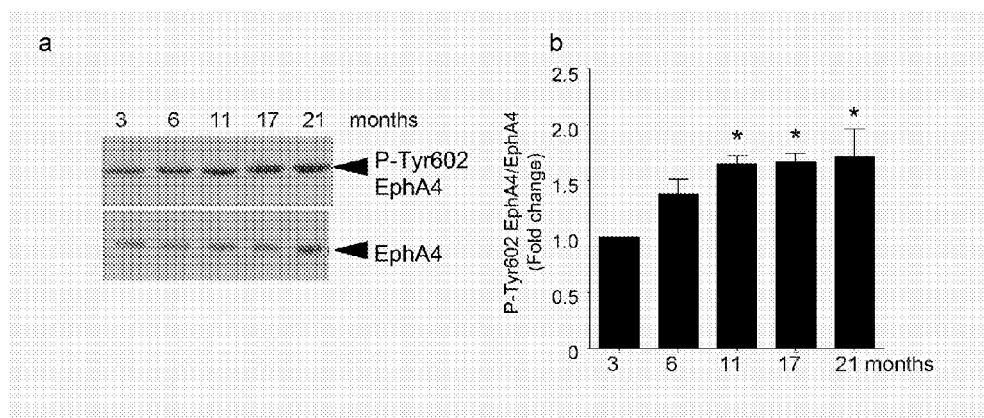
FIG. 7. Developmental expression of EphA4 tyrosine phosphorylation in the mouse brain. (a & b) Western blot of Tyr602 EphA4 phosphorylation (P-Tyr602 EphA4) and total EphA4 level in different stages of mouse brain development. (b) Quantification of P-Tyr602 normalized to EphA4 protein (compared with that of the 3-month-old brain), n=3; *$p<0.05$, one-way ANOVA followed by the Student-Newman-Keuls test.
Figure 8:
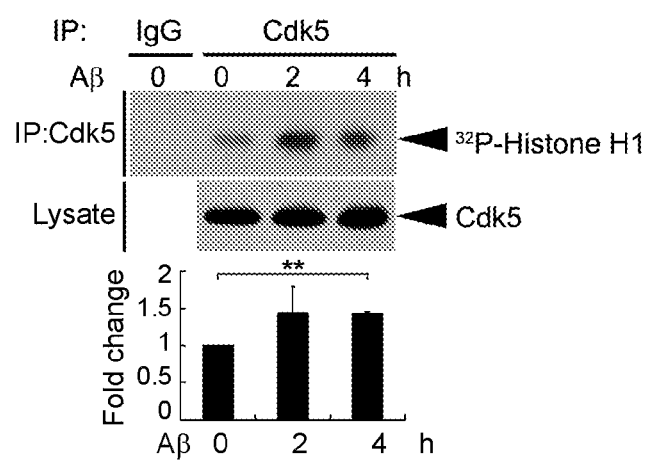
FIG. 8. Effect of Aβ on Cdk5 kinase activity. Cultured cortical neurons (16 DIV) were treated with Aβ for various durations as indicated. Cdk5 protein was immunoprecipitated from the cortical lysates and subjected to kinase assay using histone H1 protein as substrate. Bottom panel: fold change of kinase activity. **$p<0.01$ versus 0 h; Student's t test (n=3).
Figure 9:
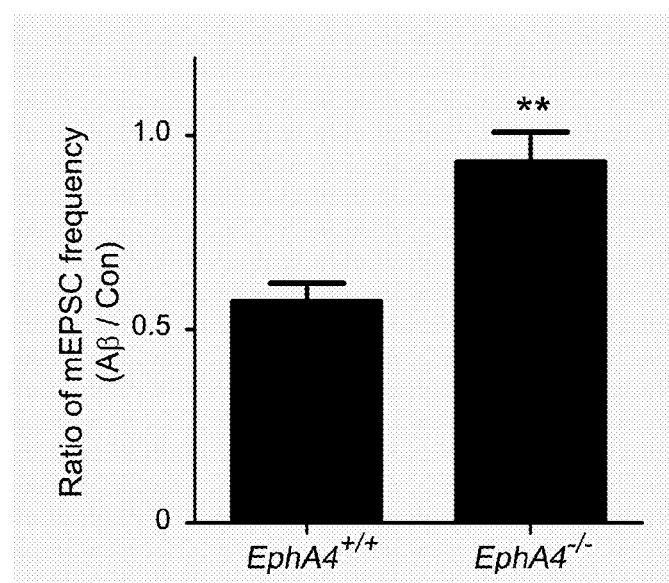
FIG. 9. Effect of Aβ stimulation on reduction of mEPSC frequency in EphA4$^{-/-}$ hippocampal neurons. mEPSCs were recorded in cultured hippocampal neurons from EphA4$^{-/-}$ mice and littermate control (EphA4$^{+/+}$) at 24-27 DIV in the presence of Aβ for 24 h. Data were presented as ratio of mEPSC frequency of Aβ-treatment against untreated (Con). Mean±SEM; WT=0.571±0.117, KO=0.931±0.188, n≥50 neurons from 6 brains. **$p<0.01$ Student's t-test.

Results
Aβ Stimulates EphA4 Activation in Neurons
As a first step to investigate whether EphA4 is involved in synaptic dysfunctions upon AD progression, the inventors examined the regulation of EphA4 protein and its activity in the hippocampus of AD mouse models. EphA4 was prominently detected in mouse hippocampal synaptosomal fractions, and its expression remained relatively unchanged upon development and aging (FIG. 1a, FIG. 7); this is consistent with previous reports that EphA4 is highly expressed in the rodent hippocampus[27,29]. The tyrosine phosphorylation of EphA4 at 602 (P-Tyr602 EphA4), which reflects the autophosphorylation status of the receptor, was upregulated in synaptosomal fractions of mouse hippocampus at 6-11 months (FIG. 7). Interestingly, P-Tyr602 EphA4 levels were elevated in the hippocampal synaptosomal fractions of an AD transgenic mouse model that expresses mutant human presenilin1 and a humanized APP (APPswePS1de9, hereafter designated APP/PS1) at as early as 3 months (~1.5-fold greater than the wild-type [WT]) (FIGS. 1a & b). Defect in synaptic plasticity was first observed in AD mouse models at ~6 months[30,31], which precedes deposition of amyloid plaques. The increase in EphA4 activity in the hippocampus of 3-month-old APP/PS1 mice is therefore consistent with the notion that EphA4 is a potential target that contributes to synaptic dysfunctions in AD. It was then examined whether EphA4 signaling in neurons is activated by Aβ, which is believed to be the major agent that causes synaptic dysfunctions in AD. Both tyrosine phosphorylation and clustering of EphA4 are required for maximal activation of the receptor[16,26]. It was found that Aβ increased the tyrosine phosphorylation of EphA4 in acute rat hippocampal slices in a dose-dependent manner (FIG. 1c-f); the increase was observed as early as 1 h and peaked at 2 h (FIGS. 1e & f). Aβ also enhanced EphA4 clustering in cultured hippocampal neurons (FIGS. 1g & h). On the other hand, the number of puncta for the postsynaptic protein PSD-95 was slightly reduced upon short-term treatment with Aβ (FIGS. 1g & h)[5]. Aβ stimulation also enhanced the activation of cyclin-dependent kinase 5, a downstream target of EphA4 (FIG. 8). Together, these results suggest that Aβ rapidly induces EphA4 activation and the downstream signaling of EphA4 in hippocampal neurons.

EphA4 is a type-I transmembrane protein with an N-terminal ectodomain comprising an ephrin-binding domain, a cysteine rich region, and a fibronectin type III repeats domain[32]. It was recently shown that Aβ directly interacts with another Eph family member, EphB2, via the fibronectin repeats domain, which leads to degradation of the receptor and downregulation of its signaling[15]. Interestingly, blockade of the ligand-binding domain of EphA4 with a peptide inhibitor (KYL peptide)[33] abolished the Aβ-stimulated tyrosine phosphorylation of EphA4 (FIGS. 1i & j). These findings suggest that EphA4-ligand interaction is critical for Aβ-triggered EphA4 activation in hippocampal neurons.

Blockade of EphA4 Activation Prevents Synaptic Dysfunctions Induced by Aβ

Figure 2:
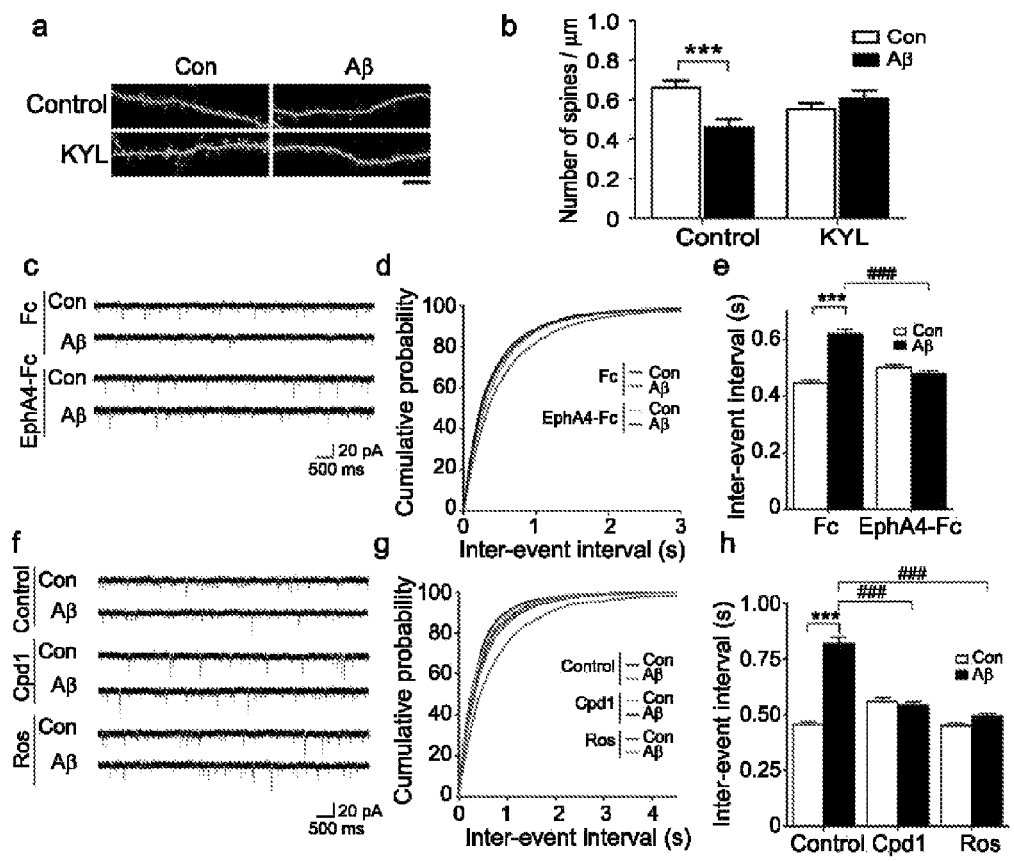
FIG. 2. Blockade of EphA4-ligand interaction prevents Aβ-mediated neurotransmission impairment. (a, b) An EphA4 inhibitor, KYL peptide, attenuated the Aβ-triggered reduction of dendritic spines in hippocampal neurons at 24-26 DIV. Representative images (a). Scale bar=10 µm. Quantification analysis of dendritic spine density (b) *$p<0.001$; two-way ANOVA followed by Bonferroni post-test (n=15-20 neurons). (c-e) Unclustered EphA4-Fc, which blocks the interaction between endogenous EphA4 and its ligand, ephrins, rescued the Aβ-triggered increase in the inter-event interval of mEPSC. (c) Representative mEPSC traces from Aβ-stimulated neurons in the presence of unclustered EphA4-Fc or Fc control. (d) Cumulative probability distributions of mEPSC inter-event interval. (e) Mean±SEM of data from (d) (mEPSC inter-event interval: Fc 445.5±8.8 ms, Fc+Aβ=619.4±14.3 ms, EphA4=500.4±9.8 ms, EphA4+Aβ=478.5±9.8 ms; ≥39 neurons were recorded in each condition from at least 3 experiments). *$p<0.001$, Aβ vs. control; ####$p<0.001$ vs. Aβ alone, one-way ANOVA with Kruskal-Wallis test. (f-h) Small molecule inhibitor for EphA4 (Cpd1) and Cdk5 (Ros) prevented the Aβ-induced increase in inter-event interval. (f) Representative mEPSCs from Aβ-stimulated neurons with or without Cpd1 (500 μM) or Ros (10 μM). (g) Cumulative probability distributions of mEPSC inter-event interval. (h) Mean±SEM of data from (g) (mEPSC inter-event interval: control=454.1±12.5 ms, Aβ=818.1±28.2 ms, Cpd1=559.5±16.6 ms, Cpd1+Aβ=542.6±15.4 ms, Ros=451.0+11.2 ms, Ros+Aβ=494.1±11.7 ms; ≥22 neurons from at least 3 experiments). ***$p<0.001$, Aβ vs. control; ####$p<0.001$ vs. Aβ alone, one-way ANOVA with Kruskal-Wallis test.

Given the negative regulatory roles of EphA4 in synaptic transmission and plasticity[24,27,29], the ability of Aβ to activate EphA4 might contribute to the synaptic dysfunctions observed in AD. To test this hypothesis, the inventors examined the effect of KYL peptide on Aβ-induced dendritic spine loss. While reduced spine density was observed in mature hippocampal neurons after Aβ treatment for 24 h (FIGS. 2a & b; 0.46±0.21/μm in Aβ vs. 0.66±0.1/μm in the control), co-treatment with KYL peptide abolished the Aβ-triggered reduction of dendritic spines (0.61±0.18/μm in the co-treatment of Aβ and KYL peptide vs. 0.55±0.13/μm in KYL peptide alone; FIGS. 2a & b). In addition to reducing the number of dendritic spines[34], Aβ also reduces neurotransmission in cultured hippocampal neurons[8], as evidenced by a decrease in the frequency of AMPAR-mediated miniature excitatory postsynaptic currents (mEPSCs). Treating neurons with Aβ significantly increased the inter-event interval, which is inversely proportional to frequency, and is accompanied by a small reduction in the amplitude of mEPSCs in cultured hippocampal neurons[8] (FIG. 2c-e, data not shown). To verify whether EphA4 activation is required for Aβ-mediated neurotransmission, an alternative approach was used to block EphA4 signaling by adding the unclustered extracellular domain of EphA4 (i.e., EphA4-Fc fusion protein), which interacts with endogenous ephrin ligand and hence prevents the activation of EphA4[24]. Unclustered EphA4-Fc similarly rescued the Aβ-induced synaptic depression and blocked Aβ-induced increase of the inter-event interval of mEPSC (FIG. 2c-e). The importance of EphA4 in Aβ-stimulated synaptic dysfunction is further confirmed in EphA4[-/-] neurons. While Aβ reduced mEPSC frequency by ~40% in neurons prepared from WT mice (EphA[+/+]), the decrease was abolished in cultured hippocampal neurons from EphA4[-/-] mice similar to that of the Fc condition (FIG. 2c-e, FIG. 9). Intriguingly, blockade of EphA4 or Cdk5 signaling by [2,5-dimethylpyrrolyl benzoic acid (Cpd1)][35] or [roscovitine (Ros)][24], respectively, also attenuated the Aβ-stimulated reduction in neurotransmission, as reflected by the reduction of Aβ-induced increase of inter-event interval of mEPSC (FIG. 2f-h). Taken together, these observations indicate that blockade of EphA4/Cdk5 signaling rescues the Aβ-induced suppression of neurotransmission.

Blockade of EphA4 Signaling Reverses the Impairment of Hippocampal Synaptic Plasticity in AD In order to evaluate the effect of blocking EphA4 signaling in Aβ-induced impairment in synaptic plasticity, the inventors measured LTP in the hippocampal Schaffer-collateral (SC) pathway in hippocampal slices upon Aβ treatment in the presence of EphA4 inhibitors (i.e., unclustered EphA4-Fc protein or KYL peptide). High-frequency stimulation (HFS) triggered a significant increase in the magnitude of SC-CA1 LTP, whereas LTP was inhibited in the slices treated with Aβ[3,36] (FIG. 3a-d). Pretreating slices with either unclustered EphA4-Fc (10 μg/mL) (FIGS. 3a & b) or KYL peptide (30 μM) (FIGS. 3c & d) for 30 min prevented the Aβ-induced suppression of LTP. Treatment with EphA4-Fc or KYL peptide alone did not significantly affect the HFS-induced LTP (FIG. 3a-d). Taken together, the present findings demonstrate that blocking EphA4-mediated signaling alleviates the Aβ-induced impairment in excitatory synaptic transmission and synaptic plasticity.

Figure 3:
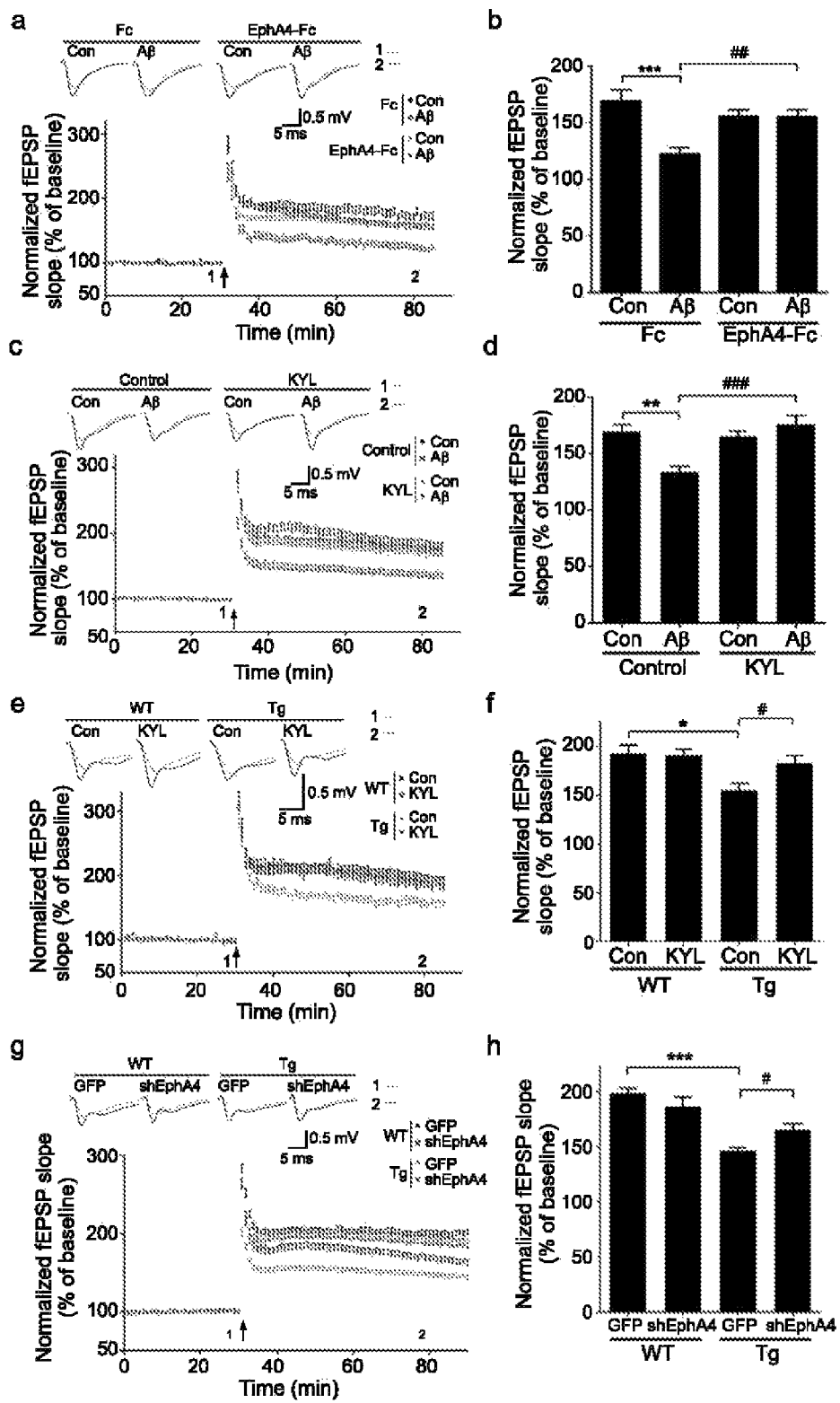
FIG. 3. Blockade of EphA4 signaling rescues the Aβ-induced impairment of hippocampal LTP. (a-d) Blockade of EphA4-ligand interaction rescued the Aβ-induced reduction of LTP. Acute hippocampal slices were treated with Aβ in the presence of EphA4 inhibitors, i.e., unclustered EphA4-Fc [10 μg/mL; (a, b)] or KYL peptide [100 μM; (c, d)] for 2 h. LTP in the CA1 of the Schaffer-collateral pathway was subsequently induced by HFS. (a, c) Points represent averaged slopes of fEPSP normalized with respect to baseline values (mean±SEM). Trace recordings 5 min before (1) and 50 min after (2) LTP induction (arrow) are shown. Inset traces are example fEPSPs recorded before (gray) and after (black) HFS. Horizontal bars: 5 ms; vertical bars: 0.5 mV. (b, d) Quantification of mean fEPSP slopes as averaged in the last 10 min of the recording after LTP induction (mean±SEM). For EphA4-Fc co-treatment: control=169.2±9.6%, n=5 brains, 10 slices; Aβ=122.0±6.1%, n=5 brains, 9 slices; EphA4-Fc=155.7±5.4%, n=6 brains, 10 slices; EphA4-Fc+Aβ=155.0±6.2%, n=5 brains, 10 slices. For KYL co-treatment: control=169±6.72%, n=6 brains, 10 slices; Aβ=132±6.06%, n=6 brains, 11 slices; KYL=164.6±5.7%, n=6 brains, 11 slices; KYL+Aβ=174.9±9.0%, n=6 brains, 11 slices. $p<0.01$, *$p<0.001$, Aβ vs. control, two-way ANOVA followed by Bonferroni post-test; ###$p<0.01$, ####$<0.001$ vs. Aβ alone, one-way ANOVA followed by the Student-Newman-Keuls test. (e-h) Blockade of EphA4 signaling rescued the LTP impairment in APP/PS1 mutant mice. (e, f) WT and APP/PS1 mutant mice were infused with KYL using an osmotic pump, and the LTP in the CA1 of the Shaffer-collateral pathway of hippocampus was subsequently induced by HFS. (g, h) WT and APP/PS1 mutant mouse hippocampi were injected with EphA4-shRNA (shEphA4) or GFP virus (GFP), and the CA3-CA1 LTP was subsequently induced by HFS 3-4 weeks after injection. (e, g) Averaged slopes of baseline-normalized fEPSP (mean±SEM). Trace recordings 5 min before (1) and 50 min after (2) LTP induction (arrow) are shown. Inset traces are example fEPSPs recorded before (gray) and after (black) HFS. Horizontal bars: 5 ms; vertical bars: 0.5 mV. (f, h) Quantification of the mean fEPSP slopes of the last 10 min of the recording after LTP induction (mean±SEM) (f) WT, Con=191.8±9.5%, n=6 brains, 9 slices; WT, KYL=190.1±6.9%, n=6 brains, 16 slices; Tg, Con=154.0±8.2%, n=6 brains, 11 slices; Tg, KYL=181.9±8.6%, n=6 brains, 9 slices. *$p<0.05$, Tg vs. WT in Con condition; #$p<0.05$, KYL vs. Con in Tg mice, one-way ANOVA followed by the Student-Newman-Keuls test. (h) WT, GFP=198.0±17.94%, n=6 brains 12 slices; WT, shEphA4=186±31.85%, n=6 brains 11 slices; Tg, GFP=146.3±17.14%, n=11 brains, 27 slices; Tg, shEphA4=164.7±23.62% n=7 brains, 14 slices; ***$p<0.001$, Tg vs. WT in GFP condition; #$p<0.05$, shEphA4 vs. GFP in Tg mice, two-way ANOVA with Bonferroni post-test.

Next, the inventors examined whether blockade of EphA4 signaling can rescue the impaired synaptic plasticity in AD mouse models. HFS-triggered hippocampal SC-CA1 LTP was impaired in 6-7-month-old APP/PS1 mice compared to littermate controls[31] (FIGS. 3e & f). Blockade of EphA4 signaling in the brain for ~3 weeks by intracerebral infusion of KYL peptide using an osmotic pump restored LTP formation in APP/PS1 mice (FIGS. 3e & f). APP/PS1 mice (Tg) exhibited a reduced slope of field excitatory postsynaptic potential (fEPSP) when compared to the WT with vehicle control, whereas the decrease in LTP was restored in APP/PS1 mice that were infused with KYL (17 μg; 0.23 μg/μL). Similarly, depletion of EphA4 expression in the CA1 region of the hippocampus in APP/PS1 mice by lentiviral-based EphA4 shRNA for 3-4 weeks alleviated the impairment of LTP (FIGS. 3g & h). The reduced LTP in APP/PS1 mice infected with green fluorescent protein (GFP) expressing virus, when compared to WT mice expressing GFP, was partially rescued by EphA4 knockdown in the CA1 region of the hippocampus. This partial rescue may be explained by the infection of only a proportion of neurons in the CA1 region with the EphA4-shRNA expressing virus (data not shown). Taken together, these findings show that the inhibition of EphA4 signaling ameliorates the synaptic dysfunctions in an AD mouse model, as evidenced by the restoration of normal synaptic transmission and rescue of LTP impairment. Thus, it would be of great interest to study whether blocking EphA4-ligand interaction is a promising intervention strategy for AD.

A Small Molecule EphA4 Inhibitor Identified by Virtual Screening

Figure 10:
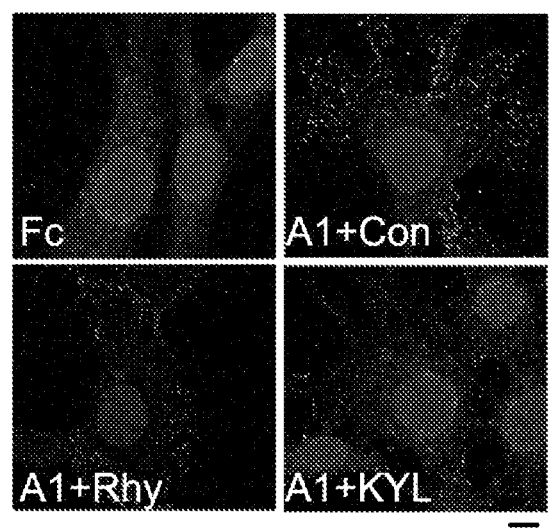
FIG. 10. Rhy inhibits the cellular binding of ephrin-A1. HT-22 cells were pre-incubated with Rhy (300 μM) or KYL (100 μM) for 10 min before treatment with 0.5 μg/mL biotinylated-ephrin-A1 (A1) for 45 min on ice. Scale bar=10 μm.
Figure 11:
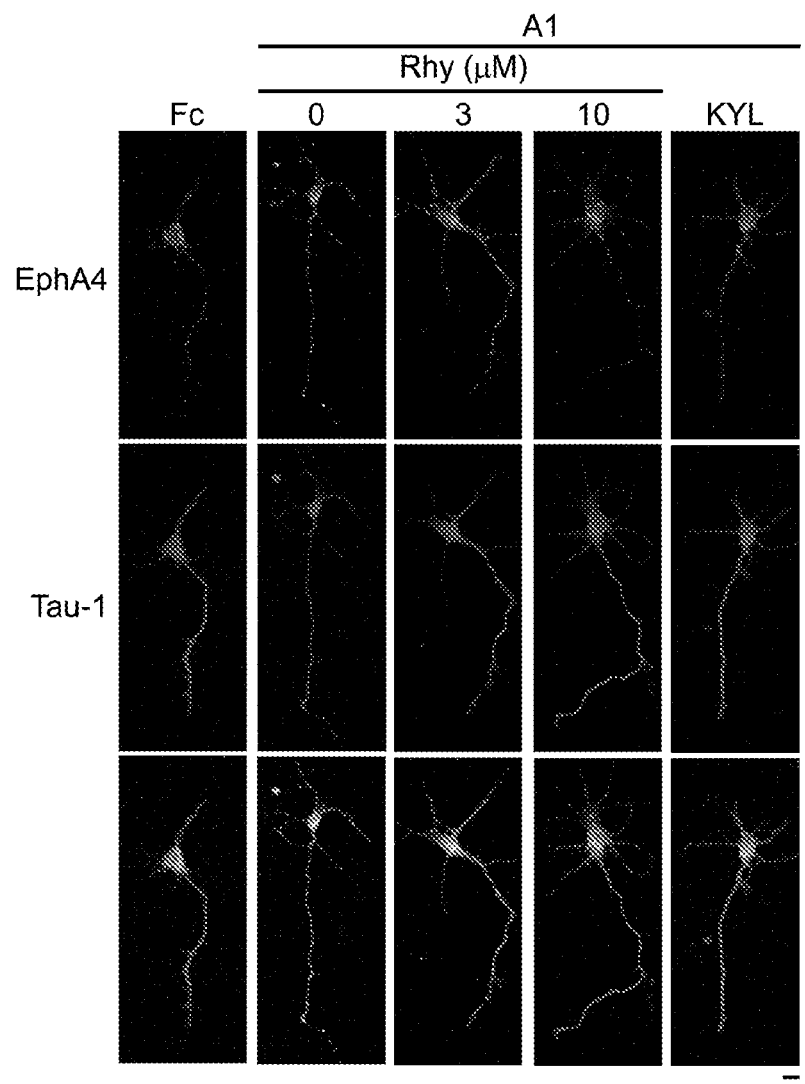
FIG. 11. Rhy abolishes ephrin-A1-induced EphA4 clustering. Cultured hippocampal neurons at 3 DIV were co-treated with clustered ephrin-A1 (A1) and Rhy at different concentrations or KYL (100 μM) as indicated, followed by staining for EphA4 and Tau-1. Representative images are shown. Scale bar=10 μm.

Detailed structural analysis of EphA4-ligand complex[32,37,38] provides a promising basis for the virtual screening of small molecules that modulate EphA4-ligand interaction. In particular, the uniqueness of the ligand-binding pocket in the ectodomain of EphA4 renders the receptor an ideal target for small molecule screening[37,39]. Thus, the inventors performed a virtual screening of an in-house traditional Chinese medicine database for EphA4 inhibitors through molecular docking. Molecular docking was performed between the extracellular domain of EphA4 and an in-house traditional Chinese medicine database containing 225 compounds together with a commercially available EphA4 inhibitor, Cpd1[35], previously identified by high-throughput screening. A small molecule, Rhy, was identified as one of the top 3 compounds that bind to EphA4 with the lowest docking energies. Rhy is the major alkaloid constituent of *Uncaria rhynchophylla* (Miq) Jack (UR), a Chinese medicinal herb commonly used in formulas targeting central nervous system diseases[40]. Nonetheless, the clinical applications of Rhy in neurodegenerative diseases such as AD have not been explored. Moreover, while this small molecule is reported to exhibit neuroprotective activity, its underlying mechanisms are largely unknown[40]. In the docking analysis, Rhy gives a significantly lower docking energy (−9.0 kcal/mol) than the previously identified EphA4 inhibitor, Cpd1 (−6.5 kcal/mol). This indicates that Rhy exhibited a higher potency in binding with EphA4 than that of Cpd1 (~67-fold higher binding affinity with EphA4; FIG. 4a)[39]. This strong binding affinity of Rhy may be attributed to its large interaction interface with the ligand-binding domain of human EphA4 (FIG. 4a). Notably Rhy forms extensive contacts with multiple hydrophobic residues on the ligand binding channel of EphA4 (FIG. 4a). Pull-down analysis revealed that biotinylated-Rhy (Bio-Rhy) bound specifically to the extracellular domain of EphA4 but not with that of EphB2 (FIG. 4b). To demonstrate whether Rhy competes with ephrin-A for binding to EphA4 in a cellular context, it was examined whether pretreatment with Rhy reduced the binding of exogenous ephrin-A1 on HT-22 cells, a cell line that expresses EphA4[41]. Similar to pretreatment with KYL peptide, Rhy pretreatment reduced the binding of ephrin-A1 to HT-22 cells (FIG. 4c; FIG. 10), suggesting that Rhy competes with ephrin-A1 for receptor binding on the cell surface. The effectiveness of Rhy as an EphA4 inhibitor was further confirmed by its ability to antagonize EphA4-dependent signaling and functions. While ephrin-A1 stimulation increased EphA4 tyrosine phosphorylation, number of EphA4 clusters, and EphA4-dependent growth cone collapse in cultured hippocampal neurons, pretreatment with Rhy reduced the specific phosphorylation (FIGS. 4d & e) and clustering (FIG. 4f; FIG. 11) of EphA4 as well as growth cone collapse (FIG. 4g) in a dose-dependent manner.

Figure 5:
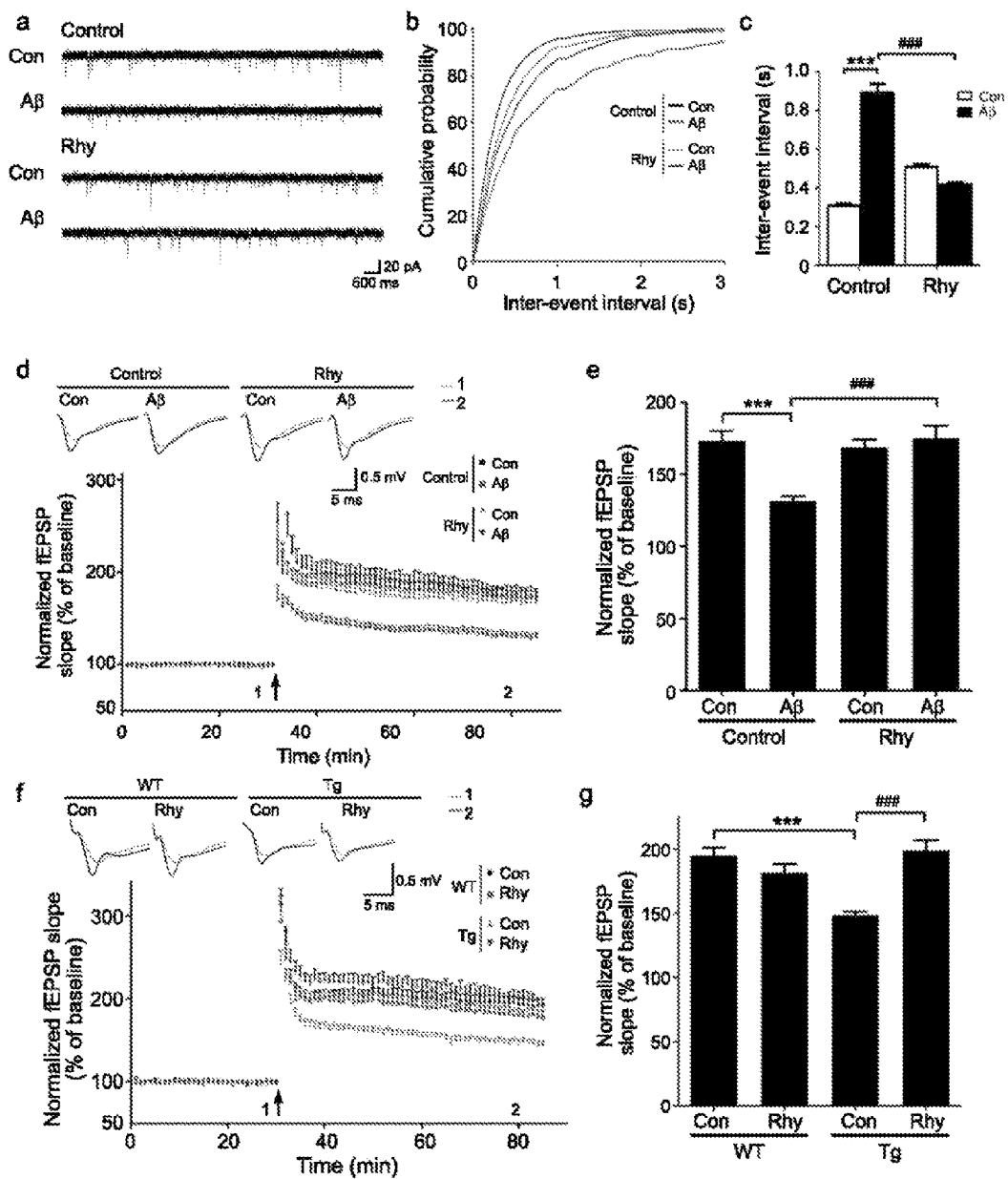
FIG. 5. Rhy rescues the Aβ-induced deficit in neurotransmission and LTP inhibition in AD mice. (a-c) Pretreatment with Rhy (10 μM) abolished the Aβ-induced reduction of neurotransmission. Hippocampal neurons were treated with Aβ in the presence of 10 μM Rhy. (a) Representative mEPSC traces. (b) Cumulative mEPSC inter-event interval distributions. (c) Mean±SEM of data from (b) (mEPSC inter-event interval: control=312.9±7.8 ms, Aβ=897.4±43.4 ms, Rhy=512.2±13.6 ms, Rhy+Aβ=420.6±9.6 ms; 17 neurons recorded in each condition from at least 3 experiments). *$p<0.001$ Aβ vs. control; ####$p<0.001$ vs. Aβ alone, one-way ANOVA followed by the Kruskal-Wallis test. (d, e) Rhy prevented the Aβ-induced inhibition of LTP. Acute hippocampal slices were treated with Aβ in the presence of Rhy (30 μM), and LTP in the CA1 of the Schaffer-collateral pathway was induced by HFS. (d) Averaged slopes of baseline-normalized fEPSP (mean±SEM). Traces recordings 5 min before (1) and 50 min after (2) LTP induction (arrow) are shown. (e) Quantification of mean fEPSP slopes during the last 10 min of the recording after LTP induction (mean±SEM); control=172.7±7.5%, n=6 brains, 10 slices; Aβ=131.1±3.9%, n=6 brains, 11 slices; Rhy=168.1±6.0%, n=6 brains, 12 slices; Rhy+Aβ=174.1±9.8%, n=6 brains, 10 slices. *$p<0.001$ Aβ vs. control, two-way ANOVA followed by Bonferroni post-test; ####$p<0.001$ vs. Aβ alone; one-way ANOVA followed by Student-Newman-Keuls test. (f, g) Rhy rescued the LTP impairment in APP/PS1 mutant mice. WT and APP/PS1 mutant mice were orally administered Rhy (50 mg·kg$^{-1}$·day$^{-1}$) for 3 weeks, and the LTP in the CA1 of the Schaffer-collateral pathway of the hippocampus was induced by HFS. (f) Averaged slopes of baseline-normalized fEPSP (mean±SEM). Trace recordings 5 min before (1) and 50 min after (2) LTP induction (arrow) are shown. (g) Quantification of mean fEPSP slopes during the last 10 min of the recording after LTP induction (mean±SEM); WT, control=194.0±7.0%, n=7 brains, 11 slices; WT, Rhy=180.5±7.7%, n=7 brains, 12 slices; Tg, control=147.6±3.5%, n=7 brains, 8 slices; Tg, Rhy=198.1±8.9%, n=6 brains, 11 slices. ***$p<0.001$ WT vs. Tg, ####$p<0.001$ control Vs. Rhy, two-way ANOVA followed by Bonferroni post-test. (d, g) Inset traces are example field excitatory postsynaptic potentials (fEPSPs) recorded before (gray) and after (black) HFS. Horizontal bars: 5 ms; vertical bars: 0.5 mV.
Figure 12:
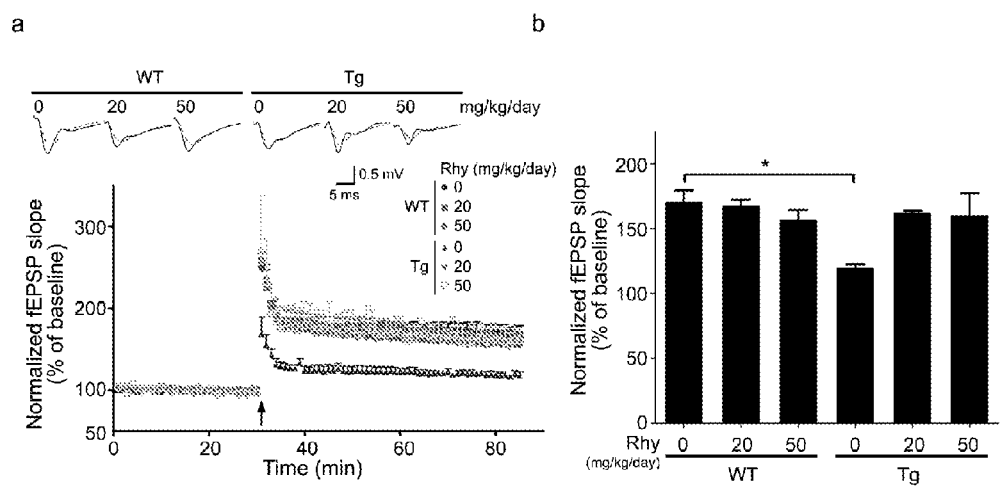
FIG. 12. Rhy rescues LTP impairment in Tg2576 mutant mice. WT and Tg2576 mutant mice were orally administered with Rhy (20 or 50 mg·kg$^{-1}$·day$^{-1}$) for 3 weeks, and LTP in the CA1 of the Shaffer-collateral pathway of the hippocampus was subsequently induced by HFS. (a) Averaged slopes of baseline-normalized fEPSP (mean±SEM). Trace recordings 5 min before (1) and 50 min after (2) LTP induction are shown. Inset traces are example field excitatory postsynaptic potentials (fEPSPs) recorded before (gray) and after (black) HFS. Horizontal bar: 5 ms; vertical bar: 0.5 mV. (b) Quantification of mean fEPSP slopes of the last 10 mins of the recording after LTP induction (mean±SEM); WT, Con=170.1±9.7%, n=3 brains, 6 slices; WT, 20 Rhy=167.3±5.2%, n=2 brains, 4 slices; WT, 50 Rhy=156.2.±8.5%, n=3 brains, 5 slices; Tg, Con=119.0±3.7%, n=3 brains, 6 slices; Tg, 20 Rhy=161.9±2.9% n=2 brains, 3 slices; Tg, 50 Rhy=159.7±17.9%, n=3 brains, 4 slices. *$p<0.05$; one-way ANOVA followed by Student-Newman-Keuls test.

Oral Administration of Rhy Reverses the Inhibition of Hippocampal Synaptic Plasticity in AD Mouse Models Given that blockade of EphA4 signaling enhances neurotransmission and synaptic plasticity during AD progression, we further examined the effects of Rhy on Aβ-induced synaptic deficits. Importantly, pretreatment of cultured hippocampal neurons with Rhy rescued the Aβ-induced impairment of mEPSC and LTP. While Aβ reduced the frequency of mEPSC (i.e., increased the inter-event interval), Rhy rescued the Aβ-induced reduction in mEPSC frequency (FIG. 5a-c). Furthermore, pretreatment of cultured hippocampal neurons with Rhy prevented Aβ from suppressing LTP, whereas treatment with Rhy alone did not affect the hippocampal LTP (FIGS. 5d & e). Importantly, oral administration of Rhy (50 mg·kg$^{-1}$·day$^{-1}$) to ~5-month-old APP/PS1 mice for 3-4 week alleviated the impairment of synaptic plasticity (FIGS. 5f & g). Compared to the WT mice, APP/PS1 mice (Tg) exhibited a decrease in LTP in response to HFS. Rhy administration completely rescued the reduction of LTP in APP/PS1 mice. Rhy exhibited a similar rescue effect on LTP inhibition in a dose-dependent manner in another AD mouse model, Tg2576 mice, which express high levels of the Swedish mutated form of human APP (FIG. 12).

Figure 6:
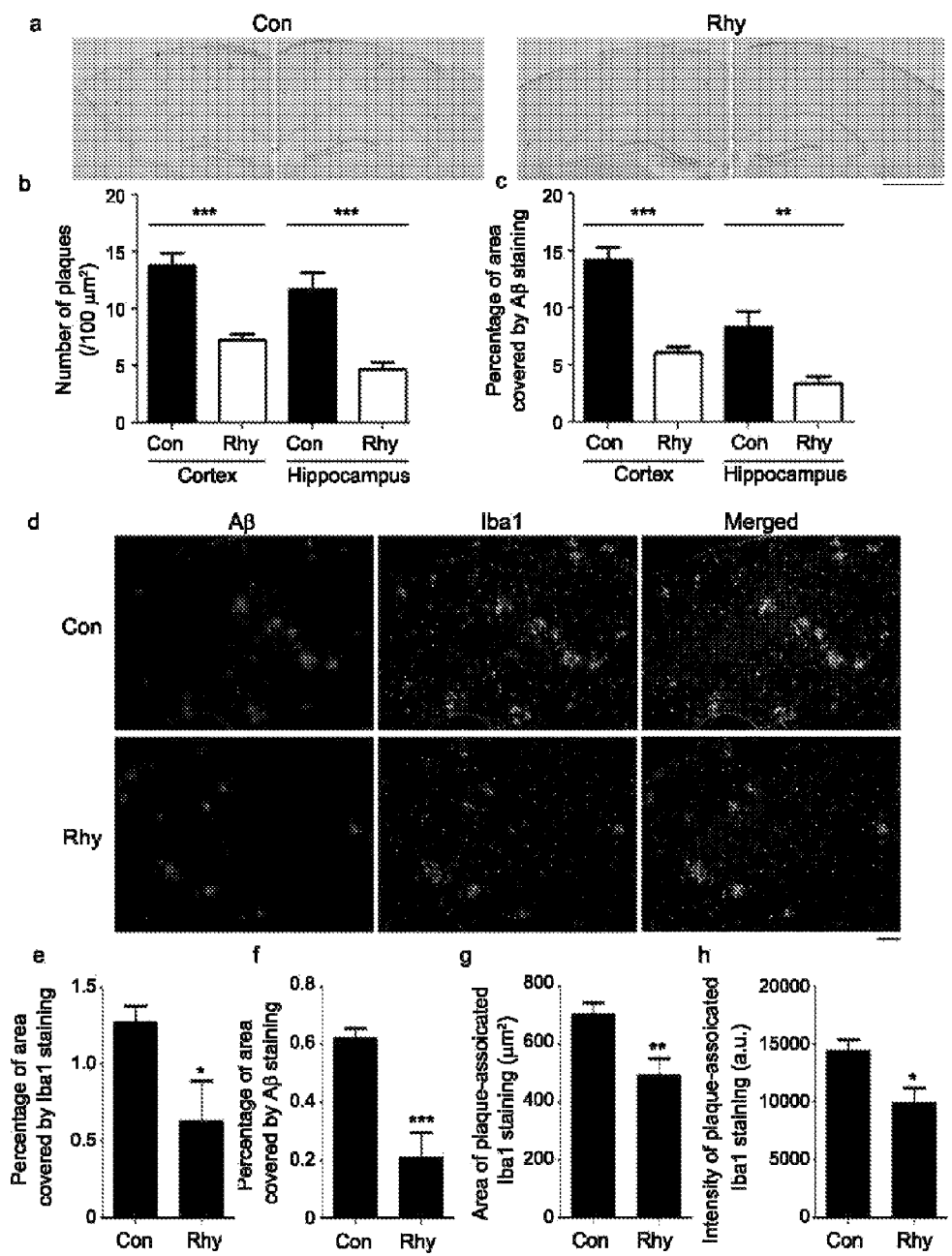
FIG. 6. Rhy administration leads to reduced amyloid plaque deposition and microglial activation. (a-c) DAB staining of amyloid plaque deposition in APP/PS1 mice after administered with Rhy for ~10 weeks (at 7.5-8 months old). (a) Representative images. Scale bar=1 mm. (b & c) Quantification of the number and percentage of total area covered by Aβ staining (amyloid plaque deposition) in cortex and hippocampus (>4 sections from each brain, n=4 brains). Data were presented as mean±SEM, *$p<0.001$, $p<0.01$, Student's t-test. (d-h) Mouse brain sections of Rhy-administered APP/PS1 mice were co-immunostained with antibodies against β-amyloid (red; for amyloid plaque deposition) and Iba-1 (green; for microglial activation). (d) Representative images of corresponding cortical regions. Scale bar=100 μm. (e-g) Quantification analysis. Percentage of area covered by Iba1 staining (e), Area (f) and intensity (g) of plaque-associated Iba1 staining (>2 sections from each brain, n=3 brains). Data were presented as mean±SEM, *$p<0.05$, $p<0.01$, *$p<0.001$, Student's t-test.

In addition to rescuing synaptic alterations in AD mouse model, Rhy also improved certain features of AD pathology. The inventors found that the number and total area of amyloid plaques decreased significantly in the cortex and hippocampus of APP/PS1 mice following 10-week administration of Rhy, when compared to treatment with water (FIG. 6a-e). Activation of microglia surrounding amyloid plaques is correlated with the deposition of amyloid plaques[42]. While extensive plaque-associated microgliosis occurred in the cortex of APP/PS1 mice, as revealed by Iba1 staining, significant reduction of plaque-associated reactive microglia was observed in the APP/PS1 mice administered with Rhy (FIG. 6f-h). Thus, Rhy, which was identified as a small molecular inhibitor of EphA4 by virtual screening, effectively rescued the deficits in synaptic plasticity in AD mouse models and slowed down the progression of AD.

Discussion

Emerging evidence revealed that synaptic loss and dysfunction, which accompany neural network failure and cognitive decline in AD, may represent the major causes of early AD development. Thus, the amelioration of synaptic dysfunction is a promising therapeutic approach for the treatment of cognitive decline in AD. The present findings demonstrate that EphA4 plays a key role in mediating the synaptic dysfunctions in AD and is a new therapeutic target for AD. Blockade of EphA4-ligand interaction using multiple approaches, including peptides and small molecules, can rescue the impaired synaptic plasticity upon disease progression. The development of small molecule inhibitors that target EphA4-ligand interaction might prove to be an effective disease-modifying treatment for AD.

EphA4 is a Cellular Target of Aβ

Although Ephs are implicated in the regulation of synaptic functions and plasticity, the possibility of members of the Eph family being cellular targets of Aβ at synapses was only investigated recently[15,26]. Whereas EphB2 is downregulated in AD and mediates Aβ-dependent synaptic dysfunctions[15], the present study revealed that EphA4 is overactivated in AD and results in synaptic dysfunctions. Recent genome-wide association studies (GWASs) identified that a single nucleotide polymorphism located proximal to EPHA4[43] and the EPHA1 gene are associated with late-onset AD[44]. Further studies aiming to identify mutations or polymorphisms of EPHA4 are warranted to elucidate whether the EPHA4 gene is associated with AD. Furthermore, it is important to examine how different members of the Eph family are involved and whether these signaling pathways crosstalk during AD progression.

How does Aβ induce EphA4 activation? Given that Aβ binds to EphB2 at the fibronectin type III domain[15] and that EphA4 also contains this same domain, Aβ might stimulate EphA4 activation through direct binding to the receptor. Alternatively, Aβ might regulate ephrin A3-EphA4 interaction to trigger EphA4 signaling. This possibility is supported by the fact that activation of postsynaptic dendritic EphA4 in the hippocampus is critically dependent upon its interaction with ephrin-A3 present in astrocytes, and that EphA4 tyrosine phosphorylation decreases in the hippocampus of ephrin-A3-knockout mice[45] and increases in mice expressing ephrin-A3[46]. Finally, Aβ might enhance EphA4 activation through regulation of neuronal activity[47]. The inventors' previous finding on the activation of EphA4 in response to chronic increase in neural activity is consistent with this possibility[27].

Pathophysiological Roles of EphA4 in AD

EphA4 is a key regulator of synaptic structure and functions in the adult hippocampus[24,27,29]. The interaction between EphA4 and its ligand ephrin-A3 produces bidirectional (i.e., forward and reverse) signals, both of which are critical for the regulation of hippocampal functions. Activation of postsynaptic EphA4 by astrocytic ephrinA enables the activation of EphA4 forward signaling in the adult rodent hippocampus and results in spine loss as well as the removal of surface AMPA receptors[27,29]. EphA4 causes the retraction of dendritic spines probably through reorganization of the actin cytoskeleton in a Cdk5-RhoA-dependent manner[24], PLCγ1-cofilin-dependent fashion[48], or by the regulation of adhesion receptors[23]. EphA4 triggers the degradation of AMPA receptors in cultured hippocampal neurons in a proteasome-dependent manner and ultimately their removal from synapses[27]. Both dendritic spine reduction and AMPA receptor removal are critical factors that contribute to synaptic loss and dysfunction during AD progression[10,34]. Another interesting feature of EphA4 is that the receptor is able to trigger reverse signaling in astrocytes through ephrin-A3 and modulate glutamate uptake by lowering glutamate transporters in glial cells[46]. EphA4- or ephrin-A3-knockout mice exhibit increased expression of glial glutamate transporters (e.g., GLAST and GLT1), whereas ephrin-A3 overexpression in astrocytes reduces the levels of these proteins. Thus, EphA4-ephrinA3 reverse signaling enhances glutamate accumulation at the synaptic cleft. While AD mice exhibit abnormal glutamate uptake[49], it will be of interest to examine whether EphA4 reverse signaling is involved in synaptic dysfunctions in AD through dysregulation of glutamate uptake. Furthermore, EphA4 was recently implicated in the regulation of the expression of inflammation-related genes in spinal cord injury[50]. Whether EphA4 regulates other pathways that contribute to AD pathology, such as inflammation, remains unknown.

EphA4 as a Target for Therapeutic Intervention in AD

Reversing synaptic dysfunctions is a potential therapeutic strategy against cognitive decline in AD. The identification of EphA4 as a cellular target of AD in the present study and the detailed structural characterization of EphA4-ligand interaction[32,37,38] offer great promise for developing EphA4 inhibitors for the treatment of AD. Indeed, various strategies for targeting EphA4 and ephrins (e.g., the recombinant extracellular domain of EphA4 fused to the Fc region of an antibody, and specific peptides and small molecules that bind to EphA4)[51] have been developed. Rhy, the small molecule identified in the present study, and the peptide KYL[52], which binds to EphA4 at the ligand-binding domain and inhibits ephrin binding, effectively alleviate the Aβ-induced synaptic dysfunction and synaptic plasticity defect in AD transgenic mouse models. While additional studies are required to exclude the possibility that Aβ binds to EphA4 at the ligand-binding domain and that these EphA4 inhibitors directly block EphA4-Aβ interaction, it is interesting to speculate that the endogenous interaction between EphA4 and ephrin mediates the Aβ-triggered synaptic deficits and dysfunction. Thus, the development of an intervention that targets EphA4-ligand interaction may be a promising therapeutic strategy for AD. In addition to AD, EphA4 inhibitors can be used as therapeutic agents for the treatment of various diseases that involve EphA4, including but not limited to amyotrophic lateral sclerosis[53] and spinal cord injury[54].

Figure 4:
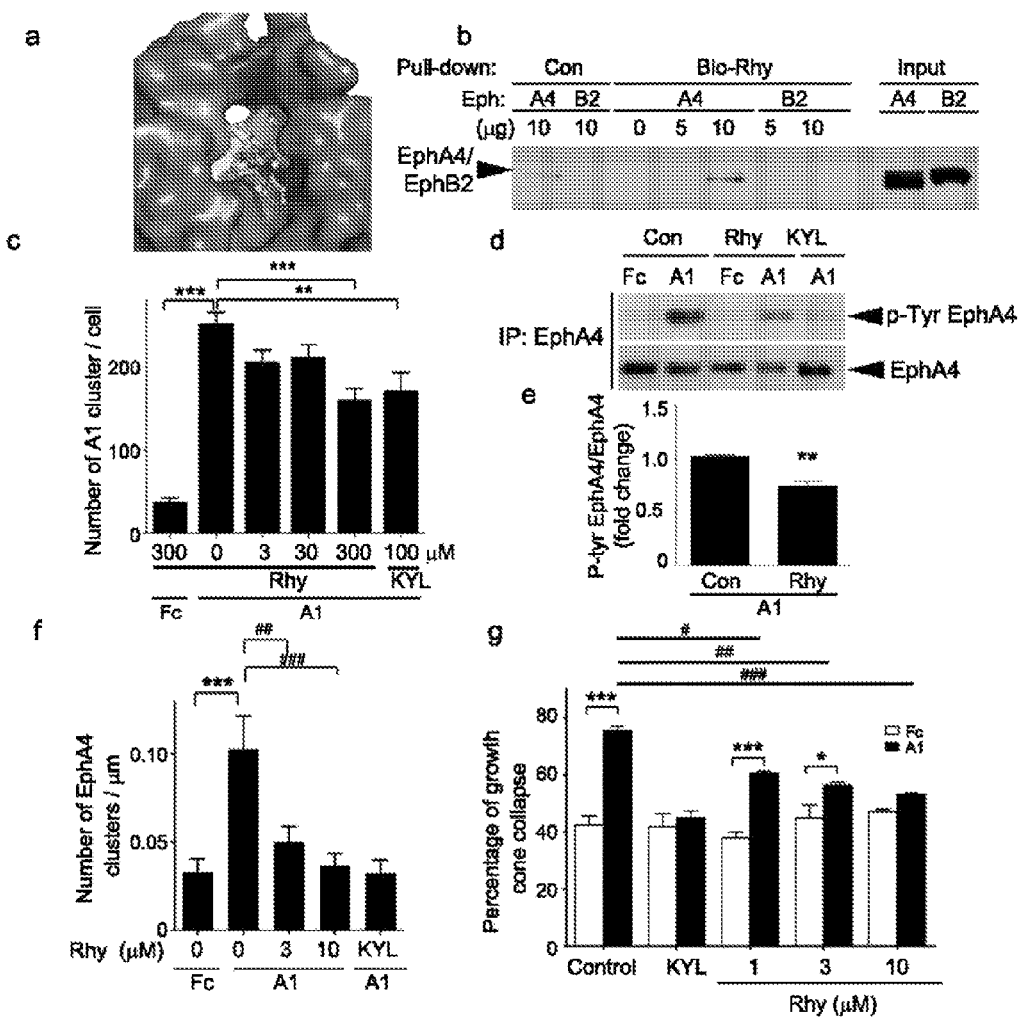
FIG. 4. A small-molecule, Rhy, is a novel inhibitor of EphA4. (a) A docking conformation of Rhy in complex with EphA4. The ligand-binding domain of EphA4 (green) is shown in surface representation, whereas Rhy is shown as sticks (cyan blue). The oxygen, nitrogen and amine hydrogen atoms of Rhy are colored in red, blue, and white, respectively. The four residues on EphA4 that form significant hydrophobic interactions with Rhy are: Ile$^{59}$ in D-E loop (orange), Phe$^{154}$ in I-J loop (red), Leu$^{166}$ in K and Val$^{195}$ in M β-strand (yellow). Moreover, the carbonyl and methoxyl oxygen atoms at ether linkage of Rhy form two strong hydrogen bonds with EphA4 at Asp$^{158}$ (~2.1 Å) and Arg$^{162}$ (~2.1 Å) within the J β-strand and J-K loop (purple). (b) Rhy binds specifically to EphA4. Rhy binds the extracellular domain of EphA4 but not that of EphB2. In vitro pull-down assay of recombinant EphA4-Fc or EphB2-Fc proteins with biotinylated Rhy coupled with streptavidin-beads (experiment were repeated for three times). (c, d) Rhy inhibited Eph-ephrin-A interaction and EphA4 tyrosine phosphorylation. (c) Rhy reduces the binding of ephrin-A1 to the surface of HT22 cells. HT-22 cells were pre-incubated with Rhy or KYL for 10 min before treatment with biotinylated-ephrin-A1 (A1; 0.5 μg/mL). Quantification analysis of biotinylated ephrin-A1 clusters on HT-22 cell surface. $p<0.01$, *$p<0.001$, one-way ANOVA followed by the Student-Newman-Keuls test. (d) Cortical neurons at 6 DIV were preincubated with Rhy for 30 min before being treated with ephrin-A1 for 30 min. Lysate was collected and immunoprecipitated with EphA4 antibody. Western blot analysis for P-Tyr. (e) Quantification analysis data are presented as mean±SEM ($p<0.01$, Student's t-test, n=5). (f, g) Rhy inhibited EphA4-dependent signaling and cellular functions. (f) The presence of Rhy abolished ephrin-A1-induced EphA4 clustering (A1). *$p<0.005$ vs. Fc, ##$p<0.01$, ####$p<0.001$ vs. A1, one-way ANOVA followed by the Student-Newman-Keuls test. (g) Rhy inhibited ephrin-A1-stimulated growth cone collapse (mean±SEM, >150 neurons from at least 3 experiments). *$p<0.05$, ***$p<0.001$, A1 vs. Fc in different conditions, two-way ANOVA followed by Bonferroni post-test; #$p<0.05$, ###$p<0.01$, ####$p<0.001$ vs. A1 in the control condition, one-way ANOVA followed by the Student-Newman-Keuls test. Similar to Rhy, Cpd1 also inhibited ephrin-A1-stimulated growth cone collapse albeit at concentration exceeding 10 μM (data not shown).

The mechanisms underlying the beneficial effect of Rhy in AD remain to be elucidated. Interestingly, Rhy has previously been suggested to be an NMDA antagonist[55] and a calcium channel blocker[56], which may also alleviate the synaptic dysfunctions of AD. However, a subsequent study revealed that Rhy neither binds to NMDA receptor nor inhibits the glutamate-induced $Ca^{2+}$ influx[57]; the present inventors also found that Rhy is unable to inhibit NMDA current in hippocampal neurons (data not shown). It is therefore unlikely that the beneficial effect of Rhy on the reversal of synaptic dysfunction in AD is due to the inhibitory action of Rhy on NMDA receptors. Here, the inventors identify Rhy as a EphA4 inhibitor through our efforts to screen for small molecules that target the ligand-binding domain of EphA4 using a structure-based in silico screening approach. The inhibitory activity of Rhy against EphA4 is confirmed by its ability to prevent ligand binding, ligand-induced activation of the receptor and its downstream signaling (FIG. 4). Given the beneficial effect of Rhy in alleviating synaptic plasticity defect in AD transgenic mice (FIG. 5), it is believed that Rhy can be used as a therapeutic agent for AD. Future characterization of the structural details of the binding interface of Rhy and EphA4 as well as with other Eph members may allow optimization of the structure of Rhy through chemical derivation, which may ultimately lead to the identification of new EphA4 inhibitors with higher affinity, specificity and potency.

In conclusion, the present findings provide evidence that EphA4 is critical for mediating the impairment of synaptic plasticity in AD pathology. Understanding the molecular and cellular mechanisms downstream of EphA4 may lead to the identification of new compounds that are useful for AD therapy. Targeting EphA4 may be beneficial for the prevention and treatment of AD. Importantly, the ability of a small molecule inhibitor of EphA4, Rhy, to alleviate synaptic impairment in AD models provides support for this intervention strategy.

Materials and Methods

Chemical, Antibodies and Virus

The antibodies used included anti-EphA4 and anti-Cdk5 antibodies (Santa Cruz Biotechnology); anti-PSD-95 (Bio-Affinity Reagents); anti-β-amyloid (6F/3D against Aβ8-17, Dako); anti-Iba-1 (Wako Pure Chemical Industries); phosphotyrosine antibody (4G10), and anti-Tau-1 antibody (Millipore); anti-actin (Sigma); phospho-Tyr 602 (p-Y602 EphA4) (ECM Biosciences); and Fc and goat antibody to human Fc (Jackson ImmunoResearch). Histone H1 recombinant protein and roscovitine were purchased from Millipore, [2,5-dimethylpyrrolyl benzoic acid (Cpd1)] from Matrix Scientific, and Rhy from Baoji Herbest Bio-Tech. Ephrin-A1, EphA4-Fc, EphB2-Fc, biotinylated-ephrin-A1-Fc, and biotinylated EphA4-Fc recombinant proteins were purchased from R&D Systems; KYL peptide from Biosynthesis; and Aβ monomer from rPeptide. The lentivirus expressing EphA4 shRNA was constructed as previously described[24,58]. The virus was packaged by the Gene Transfer Vector Core of the University of Iowa.

Synthesis of Biotinylated-Rhy and Preparation of β-Amyloid Oligomers and Ephrin

Synthesis of Bio-Rhy employed a nucleophilic substitution reaction between $N_1$ of Rhy and tert-butyl(6-bromohexyl)carbamate. The tert-butyloxycarbonyl group of the product was detached, to yield 1-hexanamine-substituted Rhy. Bio-Rhy was then obtained by reacted the substituted-Rhy with biotin in the presence of a coupling reagent.

Oligomeric Aβ (Aβ) was prepared as described previously[59,60]. Briefly, 0.5 mg monomeric Aβ1-42 was dissolved in 22.2 μL dry DMSO and then diluted in ice-cold phenol-red free F-12 medium to yield a final Aβ concentration of 100 μM. The Aβ solution was incubated at 4° C. for 24 h and then centrifuged at 14,000×g for 10 min. The supernatant was frozen in liquid nitrogen and stored at −20° C. for up to 1 month. Unless specified, cultured neurons or hippocampal slices were typically treated with Aβ at 500 nM.

Ephrin-A1-Fc was pre-clustered with goat anti-human Fc antibody (1:4.5)[24] and incubated at room temperature for 60 min before use. The growth cone collapse assay was performed in hippocampal neurons with ephrin-A1 0.1 μg/mL as described previously[61].

Virtual Screening of an In-House Traditional Chinese Medicine Database by Molecular Docking AutoDock 4.0 was employed to perform the docking between EphA4 (PDB code 2WO2) and our in-house traditional Chinese medicine database containing 225 chemical compounds[63,64]. The Lamarckian genetic algorithm was used with the following parameters: number of individuals in population, 200; maximum number of energy evaluations, 5,000,000; maximum of generations, 27,000; number of genetic algorithm runs, 20.

Cell Culture and Acute Hippocampal Slices

Primary cortical and hippocampal neurons were prepared from embryonic day 18-19 rat embryos as described previously[24]. Briefly, cortical neurons ($6 \times 10^6$ per plate) were plated on 100-mm culture dishes coated with poly-D-lysine (12.5 µg/mL; Sigma). Rat hippocampal neurons were seeded on 18-mm coverslips coated with poly-D-lysine (50 µg/mL) at a density of $0.5 \times 10^5$/18-mm coverslip for immunocytochemical analysis, $0.1 \times 10^5$/18-mm coverslip for growth cone collapse assay, or $1 \times 10^5$ or $1.5 \times 10^5$/18-mm coverslip for mEPSC recording. Neurons were fed Neurobasal medium (Invitrogen) supplemented with 2% B27 (Invitrogen). Acute brain slices were prepared from P15-P17 Sprague-Dawley rats. Briefly, the rats were rapidly capitated, and their brains were immersed in ice-cold artificial cerebrospinal fluid (ACSF). The hippocampus was dissected, and 300-µm-thick slices were prepared using a vibratome (Lieca). The slices were then transferred into an incubating chamber containing circulating ACSF equilibrated with 95% $O_2$+5% $CO_2$ and held at room temperature for at least 2 h for recovery prior to experiments[65].

AD Mouse Models, shRNA Knockdown, Peptide Infusion, and Drug Administration

APP/PS1 double-transgenic mice were obtained from Jackson Laboratory (B6C3-Tg[APPswe, PSEN1dE9] 85Dbo/J)[66]. These mice were generated by incorporating a human/murine APP construct bearing the Swedish double mutation and the exon-9-deleted PSEN1 mutation (APPswe+PSEN1/dE9). APP transgenic mice (Tg2576) expressing a double mutant of human AβPP ($Lys^{670} \rightarrow Asn^{670}$, $Met^{671} \rightarrow Leu^{671}$) were also used[31]. Both sexes were used for experiments, and all mice used in this study were produced by the Animal Care Facility of The Hong Kong University of Science and Technology. The genotype was confirmed by polymerase chain reaction analysis of tail biopsies. Four to five mice of the same sex were housed in a cage with food and water ad libitum with a 12-hour light/dark cycle.

To investigate the effect of blocking EphA4 signaling by KYL peptide in AD mice, 4-5-month-old AD transgenic mice were implanted with Alzet mini-osmotic pumps, model 1004, pumping its contents at 0.11 µL/h for 28 days. Pumps were loaded with either 0.23 µg/µL KYL peptide (17 µg) or vehicle solvent in artificial cerebrospinal fluid (CSF). The mini-osmotic pumps were adjusted intracerebroventricularly in the right hemisphere. EphA4 in the CA1 regions of APP/PS1 mice was knocked down by injecting vesicular stomatitis virus glycoprotein G-pseudotyped lentiviral particles with pFUGW-shEphA4 bilaterally into the corresponding regions as described previously[58]. AD mice were orally administered with Rhy at 20 or 50 mg·kg$^{-1}$·day$^{-1}$ (0.01 g/mL water) by daily gavage for 3-4 weeks prior to LTP measurements.

Synaptosome Preparation, Immunoprecipitation, and Western Blot Analysis

Hippocampal synaptosomes were prepared as described previously[67]. Acute hippocampal slices from P15-P17 rats were lysed in radioimmunoprecipitation assay (RIPA) buffer (1% Triton X-100, 1% sodium deoxycholate, 0.1% SDS, 150 mM NaCl, 10 mM sodium phosphate, 2 mM EDTA, and 0.2% sodium vanadate) with various protease inhibitors. For the Cdk5 kinase assay, cultured cortical neurons [16 days in vitro (DIV)] were lysed in lysis buffer A (20 mM Tris [pH 7.6], 150 mM NaCl, 1 mM EDTA, 1 mM EGTA, 1 mM NaF, and 0.5% Nonidet P-40) with various protease inhibitors. Western blot analysis was performed as described previously[24].

For the immunoprecipitation assay, lysates were immunoprecipitated with the corresponding antibody for 2 h at 4° C. followed by incubation with protein G Sepharose for 1 h at 4° C.[24]. The samples were washed with RIPA buffer or buffer A and resuspended in SDS sample buffer. EphA4 tyrosine phosphorylation was detected by western blot analysis using 4G10 antibody.

Immunocytochemical, Immunohistochemical, Confocal Microscopy, and Quantitative Analyses To examine the subcellular localization of EphA4 and PSD-95 in Aβ-treated neurons, neurons were fixed with methanol for 20 min at −20° C.[24]. Immunostaining was performed as described previously[68]. Briefly, the neurons were incubated with anti-PSD-95 antibody (1:500) and anti-EphA4 antibody (1:1000) in GDB buffer overnight at 4° C., washed with phosphate buffer, and incubated with corresponding secondary antibody for 1 h at room temperature. For image acquisition, cells were mounted in ProLong antifade reagent (Invitrogen), and images were acquired using a Zeiss Laser Scanning Confocal Microscope (LSM7 DUO) with a 63× oil-immersion objective using z-stack acquisition mode.

For immunohistochemical analysis, mice were anesthetised, transcardially perfused with saline followed by 4% paraformaldehyde (pH 7.4), and the brains were removed[66]. After overnight postfixation and a series of cryoprotection, the brains were coronally sectioned at a thickness of 20 µm using a cryostat (Microm HM 560, Thermo Scientific). The sections were stained with β-amyloid (1:200) and Iba1 (1:500) antibodies overnight at 4° C., followed by incubation with appropriate fluorescence-conjugated secondary antibodies and mounted in Hydromount (National diagnostics). Images were taken with a Leica DMRA microscope. For 3,3-diaminobenzidine (DAB) staining, the sections were rehydrated and subjected to antigen retrieval. The sections were then incubated with β-amyloid antibody diluted in Dako REAL Antibody Diluent (Dako Cytomation) overnight at 4° C., followed by secondary antibody incubation (using Dako REAL EnVision/HRP, Rabbit/Mouse) at room temperature for 1 h. β-amyloid staining was then developed by DAB method at room temperature for 10 mins (Dako REAL DAB+Chromogen). The sections were then counterstained with heamatoxylin, dehydrated in ascending concentrations of ethanol, cleared with xylene, and mounted in DPX. Images were taken using a Zeiss Lumar.V12 microscope.

Images from the same experiment were obtained using identical acquisition settings, and images were analyzed with Metamorph software (Meta Image Series 7.5, Universal Imaging Corp.)[24,58]. For quantifying the EphA4 and PSD-95 clusters, two dendrite segments from each neuron were analyzed for quantification. The outlines of dendrites were manually traced. The basal threshold values for the background of all images in each experiment were measured. The average of these threshold values was then applied to all images in the same experiment. To measure the density of clusters in dendrites, the images were first thresholded to include the clusters with intensity 2-fold greater than the signal of an adjacent dendrite, and the total number of clusters and dendrite length were measured automatically. For quantification of DAB, Iba1 or Aβ staining, images were thresholded to include the clusters with intensity of 2.5 fold higher than that of the background signal in the control. The cortical and hippocampal regions were traced, and the amyloid deposition was quantified as the number and the percentage of area (the area covered by Aβ staining over the area of interest) of plaques in the cortex or in the hippocampus. For quantifying plaque-associated Iba1 staining, the area and intensity of Iba1 staining surrounding amyloid deposition was measured.

Densitometric quantification of protein band intensity was performed using the NIH Image J program. Statistical analysis was performed using Student's t-test or ANOVA where appropriate followed by different tests as indicated in the figure legends. All experiments were performed at least 3 times except indicated.

Cdk5 Kinase Assay

The Cdk5/p35 kinase assay was performed in the kinase buffer (20 mM MOPS [pH 7.4], 15 mM $MgCl_2$, and 100 μM ATP) containing 1-2 μCi [γ-$^{32}$P] ATP and 8 μg histone-H1 protein for 30 min at 30° C.[24]. The phosphorylated histone-H1 protein was then separated using 15% SDS-PAGE and visualized by autoradiography.

Rhy-EphA4-Binding Assay

For the pull-down analysis, Bio-Rhy was bound to streptavidin magnetic beads for 1 h, the beads was then incubated with recombinant EphA4-Fc or EphB2-Fc in the presence of 0.5% BSA for 1 h. After incubation, the beads were washed 4 times with DPBS and the presence of Eph in the complex was determined by western blot analysis.

To examine Rhy whether inhibited the binding of ephrin-A1 to the cell surface of HT-22 cells, the cell-based binding assay was performed as described previously with some modifications[69]. HT-22 cells were seeded on poly-D-lysine coverslips. The cells were pre-incubated with different concentrations of Rhy or KYL for 10 min at 4° C., followed by incubation with 0.5 μg/mL biotinylated-ephrin-A1 for 45 min at 4° C. The cells were then fixed with 4% paraformaldehyde and then immunostained with Alexa Fluor 488-conjugated Streptavidin antibody (Molecular Probes) for surfacing labeling of biotinylated ephrin-A1.

EphA4 Clustering and Growth Cone Collapse Assay

Neurons at 3 DIV were pretreated with different concentrations of Rhy or KYL as a control for 15 min, with pre-clustered ephrin-A1 for another 15 min, and fixed with 4% paraformaldehyde[61]. For EphA4 clustering, neurons were stained with anti-EphA4 and anti-Tau-1 antibodies. For the growth cone collapse assay, neurons were stained with Alexa Fluor 555-conjugated phalloidin (Molecular Probes) for filamentous actin and anti-Tau-1 antibody for axons. Collapsed growth cones were scored in a double-blinded manner. The experiments were repeated at least 3 times, and >50 neurons were analyzed for each experiment. Data are presented as mean±SEM.

Dendritic Spine Analysis

Cultured rat hippocampal neurons were transfected with GFP plasmid at 14-16 DIV and exposed to Aβ at 24-28 DIV for 24 h after treatment with 30 μM KYL peptide. The neurons were fixed with 4% paraformaldehyde and examined using confocal microscopy using a 63× objective lens as previously described[24].

Electrophysiology

For miniature EPSC recordings, hippocampal neurons at ~25-28 DIV were co-treated with or without 500 nM Aβ together with the testing reagents for 24 h. Whole-cell patch-clamp recordings were made at room temperature with external solution containing (in mM) 110 NaCl, 5 KCl, 2 $CaCl_2$, 0.8 $MgCl_2$, 10 HEPES, and 10 D-glucose (pH 7.4) as well as an internal solution containing (in mM) 135 $CsCl_2$, 10 HEPES, 2 $MgCl_2$, 4 NaATP, 0.4 NaGTP, and 0.5 EGTA (pH 7.2)[24,27]. Picrotoxin (200 μm) was included in the external solution to block GABAergic IPSCs along with 0.5 μM TTX to prevent action potential-evoked EPSCs. For miniature EPSC recordings, cells were held at −70 mV. The pipette resistances for these experiments were typically 3-5 MΩ, while series resistances were 15-20 MΩ. The minis from each cell was recorded for 1 min in each condition. The measurement of mEPSC was according to that described in Mini Analysis Program for measuring AMPA receptor EPSCs (Synaptosoft Inc.). Only recording epochs in which series and input resistances varied <10% were analyzed. Data are presented as the mean±SEM of at least 3 experiments.

For LTP recordings, mouse brains were immediately dissected after sacrifice and soaked in ice-cold 95% $O_2$/5% $CO_2$ (aCSF)[58]. Brain slices (300 μm thick) were prepared using a vibrating tissue slicer (HM650V; Thermo), and soaked in oxygenated buffer for 2 h at 32° C. The hippocampal regions were resected and placed at the center of a MED-P210A probe (Panasonic International Inc) with 64 embedded recording electrodes. The slices were then perfused with Aβ at 500 nM in oxygenated aCSF for 2 h before LTP induction[70]. For treatment with EphA4 inhibitors, the slices were pretreated with peptides or chemicals for 1 h before application of Aβ. fEPSPs were recorded using a MED64 multichannel recording system, and the data were collected from the dendritic layer of area CA1 at a sampling rate of 10 kHz. For each slice, the baseline stimulus intensity was set at the level that elicited ~50% of the maximum fEPSP response determined according to the input-output curve. LTP was induced by 3 trains of HFS (100 Hz, 1 s, delivered 30 s apart). The magnitude of LTP was quantified as a percentage change in the fEPSP slope (10%-90%) taken during the 60-min interval after LTP induction.

Example 2

Corylin and Dendrobine Inhibit EphA4 Signaling

To screen for small molecule EphA4 inhibitors, the inventors performed a molecular docking analysis using a small molecule library. In addition to Rhy, two small molecules (screened from one TCM database) also exhibit EphA4 inhibition activity. Their ability in inhibiting EphA4 inhibiting the EphA4-dependent growth cone collapse using cultured hippocampal neurons was performed. When rat hippocampal neurons were treated with the small molecules (Corylin, Dendrobine) at the concentrations indicated in FIG. 13 and treated with ephrin-A1, the compounds inhibited ephrin-A1-stimulated growth cone collapse.

Example 3

Compounds Derived from Cpd1 Inhibit EphA4 Signaling

As described in Noberini et al., supra, Cpd1 has the chemical name of 2-hydroxy-4-(2,5-dimethyl-1-pyrrolyl) benzoic acid and has the chemical formula of:

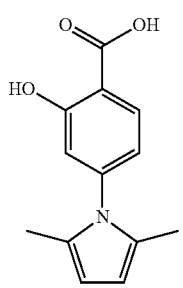

Figure 15:
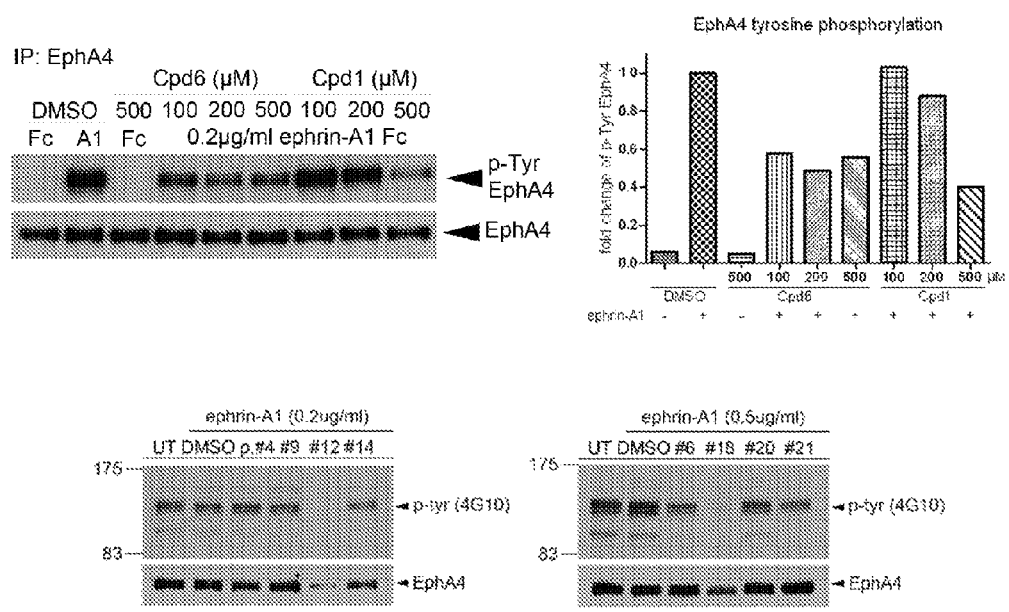
FIG. 15. Derivatives of cpd1: compounds 6, 14, and 21 exhibit inhibitory effect on EphA4 signaling. The inhibitory effect was indicated by the compounds' ability to suppress tyrosine phosphorylation of EphA4 upon exposure to ephrin A1.

The present inventors have generated several chemical derivatives from Cpd1 and found compounds 6, 14, and 21 to possess the activity of EphA4 signaling inhibitors. These Cpd1-derived compounds are shown in FIG. 14 by their chemical name and formula. Their EphA4 inhibitory effect is shown in FIG. 15. Briefly, rat cortical neurons were treated with the compounds derived from Cpd1 at varying concentrations and treated with Ephrin-A1. FIG. 15 shows the results of western blot analysis for EphA4 tyrosine phosphorylation.

Example 4

Synthesis of Novel Rhy Derivatives

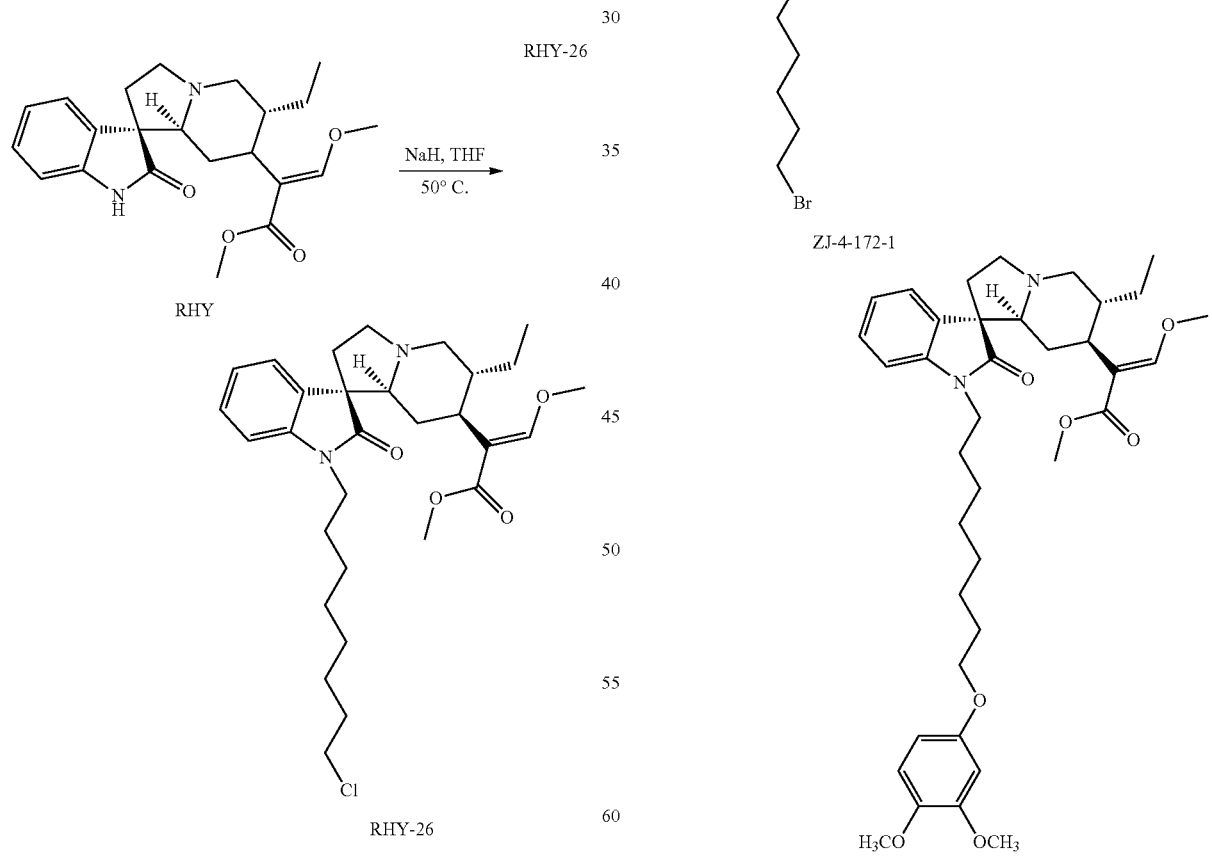

To the solution of Rhy (100 mg) in tetrahydrofuran (THF, 5 mL), was added sodium hydride (NaH, 50 mg), followed with 1,8-dichlorooctane (0.24 mL). The mixture was heated to 50° C., and after stirring for 20 h, the reaction was quenched with water (10 mL), extracted with dichol-oromethane (DCM, 3×15 mL), and washed with saturated NaHCO₃ aqueous (20 mL). The combined organic layers were dried over Na₂SO₄, filtered, and the solvent was removed in vacuo. The residue was purified by column chromatography (silica gel, MeOH/DCM=1:30) to give RHY-26 (5 mg) as yellow oil.

Step 1:

To the solution of RHY (100 mg) in THF (2 mL), was added NaH (50 mg), followed with 1,8-dibromooctane (0.20 mL). The mixture was heated to 50° C., and after stirring for 20 h, the reaction was quenched with water (10 mL), extracted with DCM (3×15 mL), and washed with saturated NaHCO₃ aqueous (20 mL). The combined organic layers were dried over Na₂SO₄, filtered, and the solvent was removed in vacuo. The residue was purified by column chromatography (silica gel, MeOH/DCM=1:20) to give ZJ-4-172-1 (70 mg) as yellow oil.

Step 2:

To the solution of ZJ-4-172-1 (70 mg) in DMF (1 mL), was added NaH (20 mg), followed with 3,4-dimethoxyphenol (56 mg). The mixture was heated to 50° C., and after stirring for 20 h, the reaction was quenched with water (5 mL), extracted with DCM (3×5 mL), and washed with saturated NaHCO₃ aqueous (10 mL). The combined organic layers were dried over Na₂SO₄, filtered, and the solvent was removed in vacuo. The residue was purified by column chromatography (silica gel, MeOH/DCM=1:33) to give RHY-37 (20 mg) as yellow oil.

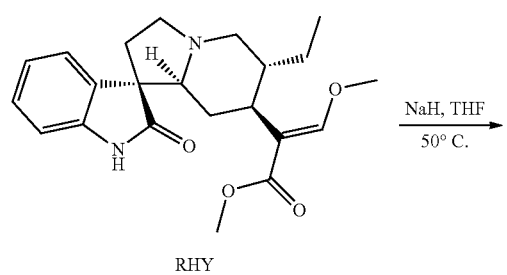

RHY

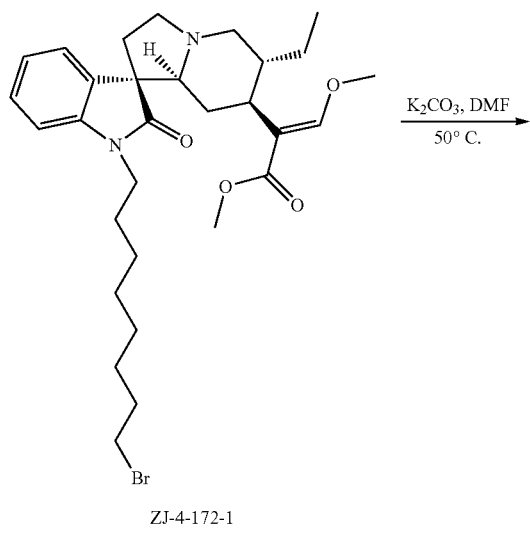

ZJ-4-172-1

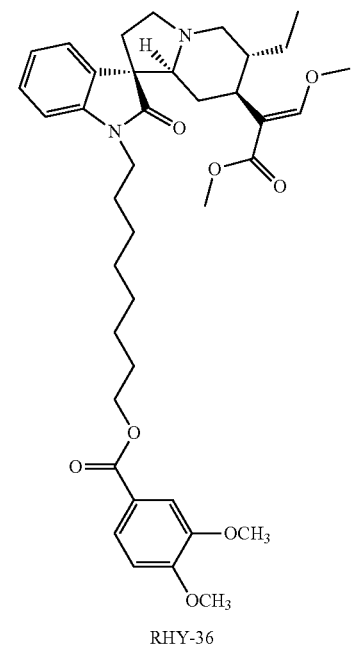

RHY-36

Step 1:

To the solution of RHY (100 mg) in THF (2 mL), was added NaH (50 mg), followed with 1,8-dibromooctane (0.20 mL), the mixture was heated up to 50° C., after stirring for 20 h, the reaction was quenched with water (10 mL), extracted with DCM (3×15 mL), washed with saturated NaHCO₃ aqueous (20 mL). The combined organic layers were dried over Na₂SO₄, filtered and the solvent was removed in vacuo. The residue was purified by column chromatography (silica gel, MeOH/DCM=1:20) to give ZJ-4-172-1 (70 mg) as yellow oil.

Step 2:

To the solution of ZJ-4-172-1 (40 mg) in DMF (1 mL), was added K₂CO₃ (38 mg), followed with 3,4-dimethoxybenzoic acid (38 mg), the mixture was heated up to 50° C., after stirring for 20 h, the reaction was quenched with water (5 mL), extracted with DCM (3×5 mL), washed with saturated NaHCO₃ aqueous (10 mL). The combined organic layers were dried over Na₂SO₄, filtered and the solvent was removed in vacuo. The residue was purified by column chromatography (silica gel, MeOH/DCM=1:33) to give RHY-36 (10 mg) as yellow oil.

RHY-42

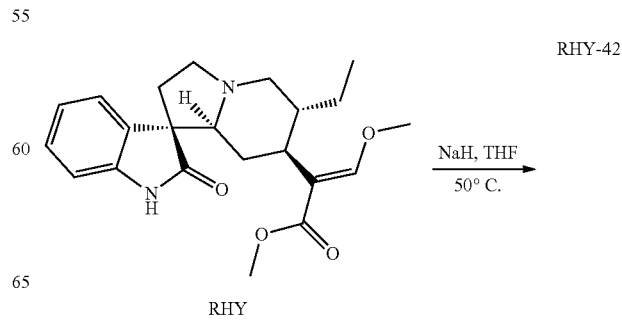

RHY

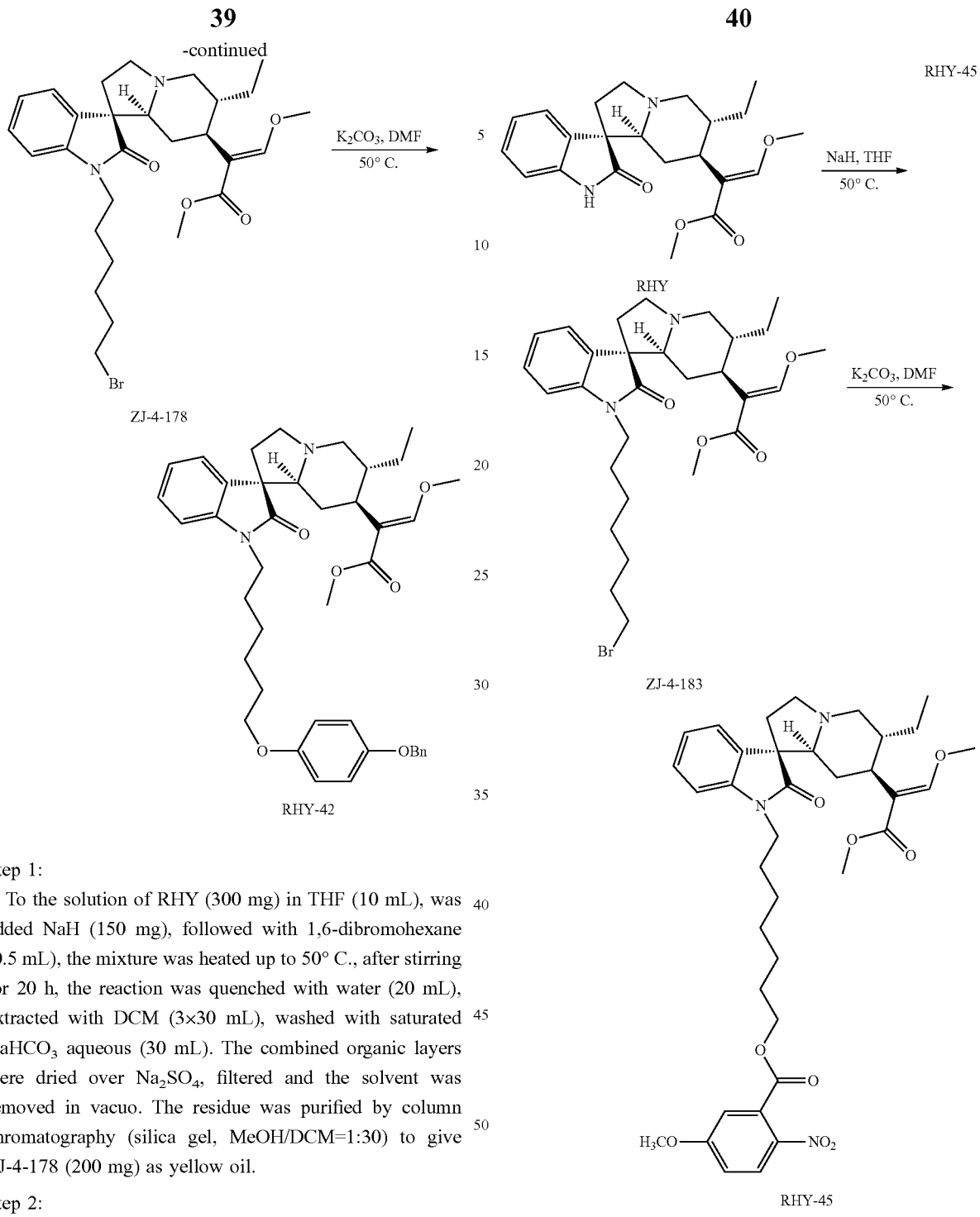

Step 1:

To the solution of RHY (300 mg) in THF (10 mL), was added NaH (150 mg), followed with 1,6-dibromohexane (0.5 mL), the mixture was heated up to 50° C., after stirring for 20 h, the reaction was quenched with water (20 mL), extracted with DCM (3×30 mL), washed with saturated NaHCO$_3$ aqueous (30 mL). The combined organic layers were dried over Na$_2$SO$_4$, filtered and the solvent was removed in vacuo. The residue was purified by column chromatography (silica gel, MeOH/DCM=1:30) to give ZJ-4-178 (200 mg) as yellow oil.

Step 2:

To the solution of ZJ-4-178 (90 mg) in DMF (3 mL), was added K$_2$CO$_3$ (68 mg), followed with 4-(benzyloxy)phenol (100 mg), the mixture was heated up to 50° C., after stirring for 20 h, the reaction was quenched with water (10 mL), extracted with DCM (3×10 mL), washed with saturated NaHCO$_3$ aqueous (20 mL). The combined organic layers were dried over Na$_2$SO$_4$, filtered and the solvent was removed in vacuo. The residue was purified by column chromatography (silica gel, MeOH/DCM=1:30) to give RHY-42 (50 mg) as yellow oil.

Step 1:

To the solution of RHY (300 mg) in THF (10 mL), was added NaH (150 mg), followed with 1,7-dibromoheptane (0.53 mL), the mixture was heated up to 50° C., after stirring for 20 h, the reaction was quenched with water (20 mL), extracted with DCM (3×30 mL), washed with saturated NaHCO$_3$ aqueous (30 mL). The combined organic layers were dried over Na$_2$SO$_4$, filtered and the solvent was removed in vacuo. The residue was purified by column chromatography (silica gel, MeOH/DCM=1:30) to give ZJ-4-183 (220 mg) as yellow oil.

Step 2:

To the solution of ZJ-4-183 (60 mg) in DMF (2 mL), was added K$_2$CO$_3$ (50 mg), followed with 5-methoxy-2-nitrobenzoic acid (64 mg), the mixture was heated up to 50° C., after stirring for 20 h, the reaction was quenched with water (10 mL), extracted with DCM (3×10 mL), washed with saturated NaHCO$_3$ aqueous (20 mL). The combined organic layers were dried over Na$_2$SO$_4$, filtered and the solvent was removed in vacuo. The residue was purified by column chromatography (silica gel, MeOH/DCM=1:30) to give RHY-45 (20 mg) as yellow oil.

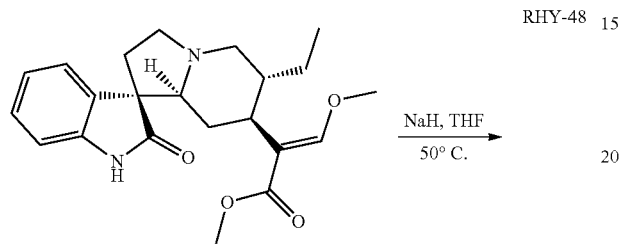

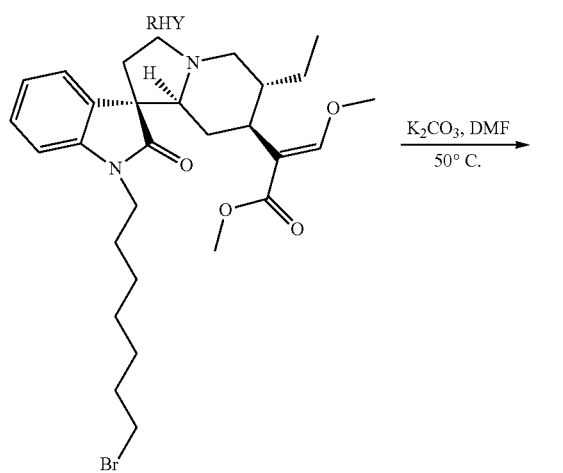

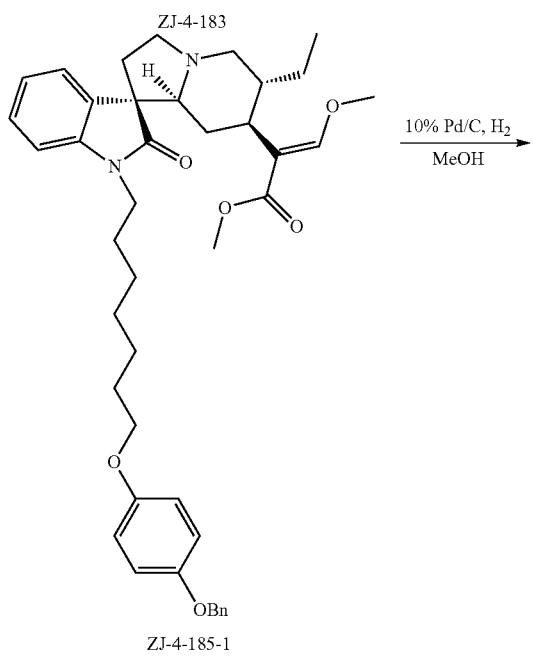

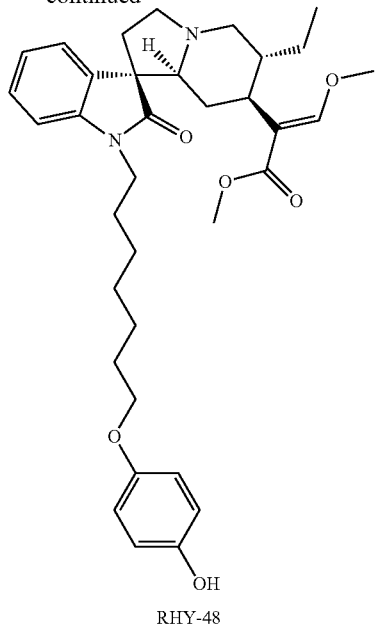

Step 1:

To the solution of RHY (300 mg) in THF (10 mL), was added NaH (150 mg), followed with 1,7-dibromoheptane (0.53 mL), the mixture was heated up to 50° C., after stirring for 20 h, the reaction was quenched with water (20 mL), extracted with DCM (3×30 mL), washed with saturated NaHCO$_3$ aqueous (30 mL). The combined organic layers were dried over Na$_2$SO$_4$, filtered and the solvent was removed in vacuo. The residue was purified by column chromatography (silica gel, MeOH/DCM=1:30) to give ZJ-4-183 (220 mg) as yellow oil.

Step 2:

To the solution of ZJ-4-183 (60 mg) in DMF (2 mL), was added K$_2$CO$_3$ (45 mg), followed with 4-(benzyloxy)phenol (50 mg), the mixture was heated up to 50° C., after stirring for 20 h, the reaction was quenched with water (10 mL), extracted with DCM (3×10 mL), washed with saturated NaHCO$_3$ aqueous (20 mL). The combined organic layers were dried over Na$_2$SO$_4$, filtered and the solvent was removed in vacuo. The residue was purified by column chromatography (silica gel, MeOH/DCM=1:30) to give ZJ-4-185-1 (30 mg) as yellow oil.

Step 3:

To the solution of ZJ-4-185-1 (20 mg) in MeOH (2 mL), was added 10% Pd/C (10 mg), the mixture was stirred for 20 h in H$_2$, then the mixture was filtered over a pad of Celite (MeOH eluent) and the solvent was evaporated in vacuo. The crude product was purified by column chromatography (silica gel, MeOH/DCM=1:30) to give RHY-48 (10 mg) as yellow oil.

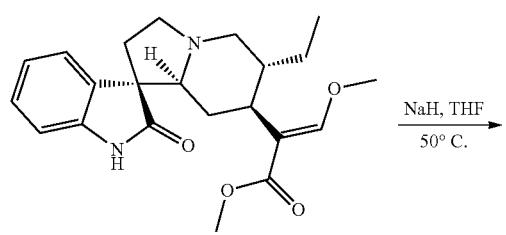

RHY

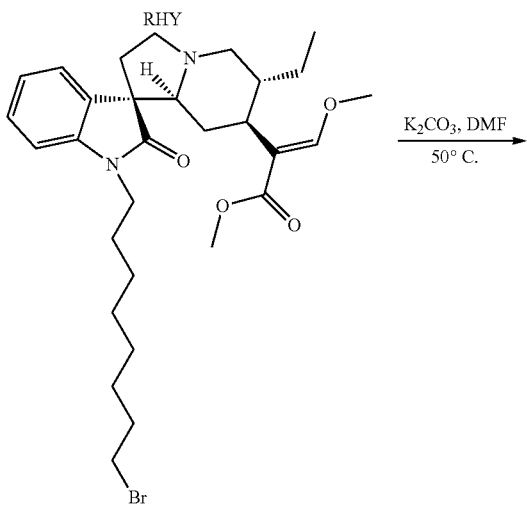

ZJ-4-189

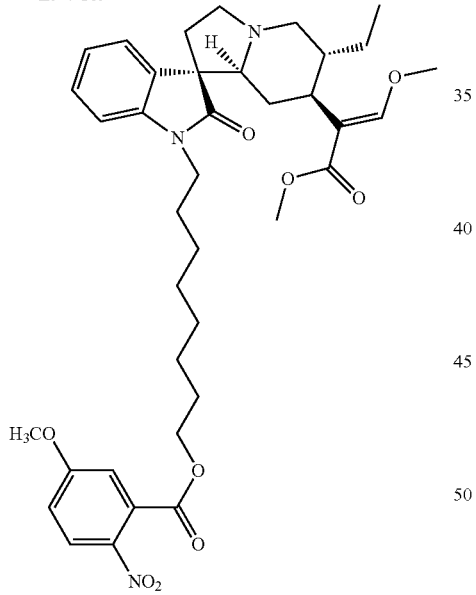

RHY-50

Step 1:
To the solution of RHY (300 mg) in THF (15 mL), was added NaH (150 mg), followed with 1,8-dibromooctane (0.58 mL), the mixture was heated up to 50° C., after stirring for 20 h, the reaction was quenched with water (20 mL), extracted with DCM (3×30 mL), washed with saturated NaHCO$_3$ aqueous (30 mL). The combined organic layers were dried over Na$_2$SO$_4$, filtered and the solvent was removed in vacuo. The residue was purified by column chromatography (silica gel, MeOH/DCM=1:30) to give ZJ-4-189 (200 mg) as yellow oil.

Step 2:
To the solution of ZJ-4-189 (60 mg) in DMF (2 mL), was added K$_2$CO$_3$ (60 mg), followed with 5-methoxy-2-nitrobenzoic acid (50 mg), the mixture was heated up to 50° C., after stirring for 20 h, the reaction was quenched with water (10 mL), extracted with DCM (3×10 mL), washed with saturated NaHCO$_3$ aqueous (20 mL). The combined organic layers were dried over Na$_2$SO$_4$, filtered and the solvent was removed in vacuo. The residue was purified by column chromatography (silica gel, MeOH/DCM=1:30) to give RHY-50 (20 mg) as yellow oil.

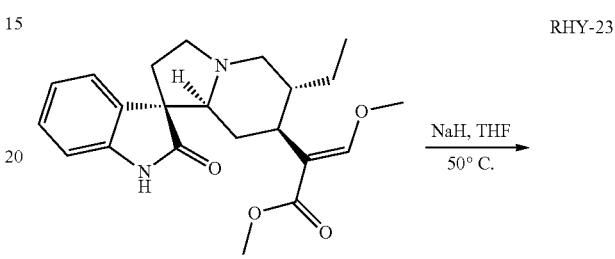

RHY

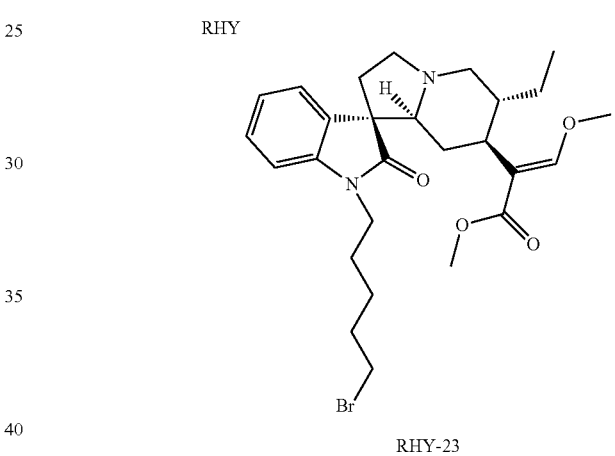

RHY-23

To the solution of RHY (100 mg) in THF (5 mL), was added NaH (50 mg), followed with 1,5-dibromopentane (0.18 mL), the mixture was heated up to 50° C., after stirring for 20 hrs, the reaction was quenched with water (10 mL), extracted with DCM (3×15 mL), washed with saturated NaHCO$_3$ aqueous (20 mL). The combined organic layers were dried over Na$_2$SO$_4$, filtered and the solvent was removed in vacuo. The residue was purified by column chromatography (silica gel, MeOH/DCM=1:30) to give RHY-23 (100 mg) as yellow oil.

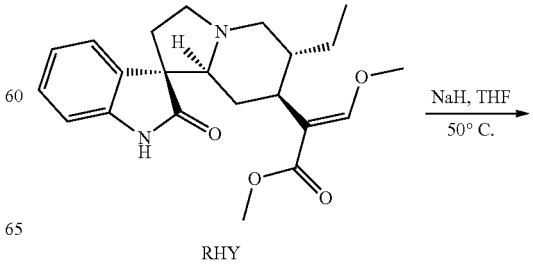

RHY

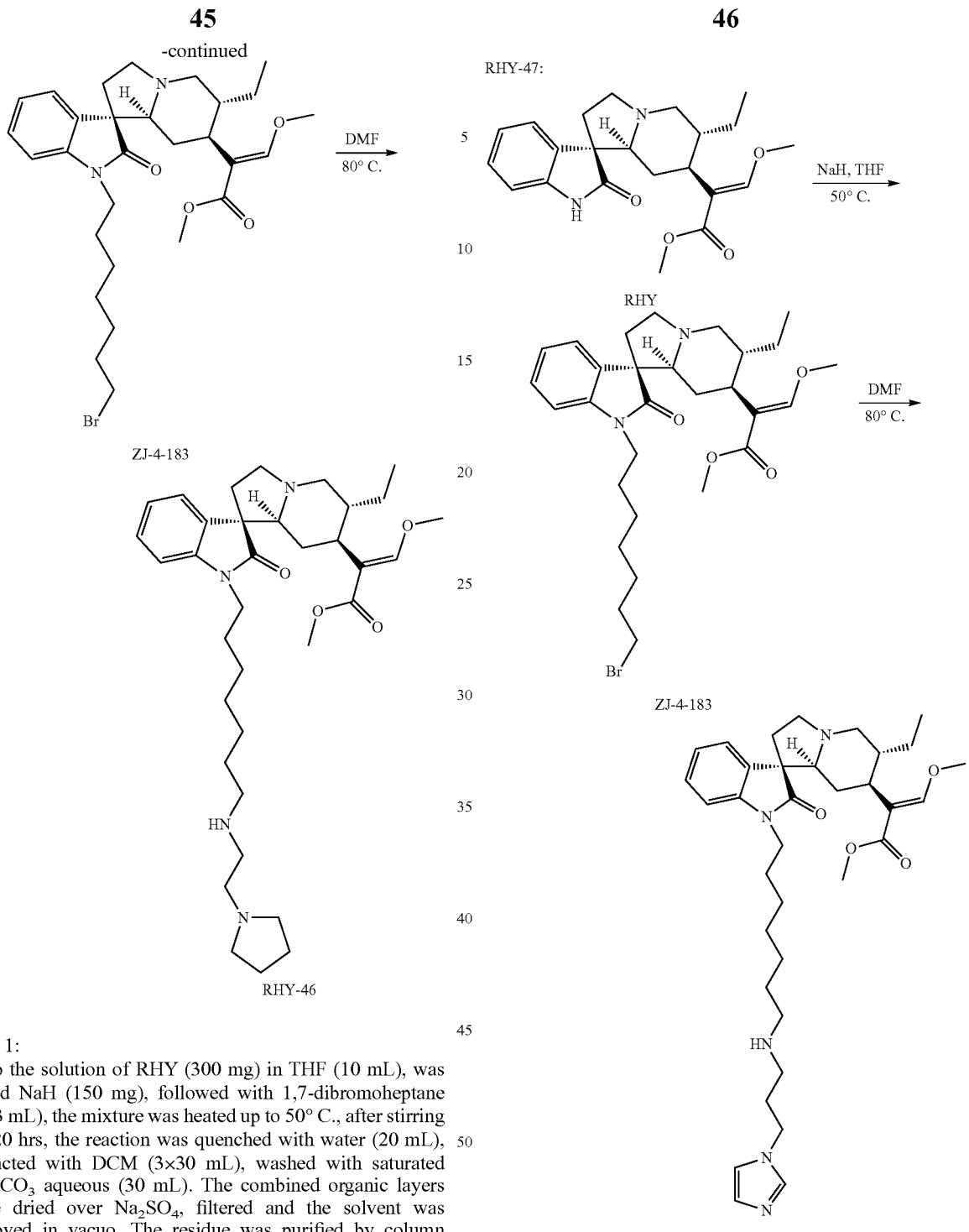

Step 1:
To the solution of RHY (300 mg) in THF (10 mL), was added NaH (150 mg), followed with 1,7-dibromoheptane (0.53 mL), the mixture was heated up to 50° C., after stirring for 20 hrs, the reaction was quenched with water (20 mL), extracted with DCM (3×30 mL), washed with saturated NaHCO₃ aqueous (30 mL). The combined organic layers were dried over Na₂SO₄, filtered and the solvent was removed in vacuo. The residue was purified by column chromatography (silica gel, MeOH/DCM=1:30) to give ZJ-4-183 (220 mg) as yellow oil.

Step 2:
To the solution of ZJ-4-183 (70 mg) in DMF (1 mL), was added 2-(pyrrolidin-1-yl)ethanamine (90 μL), the mixture was heated up to 80° C., after stirring for 20 hrs, the reaction was quenched with saturated NaHCO₃ aqueous (10 mL), extracted with DCM (3×10 mL), washed with saturated H₂O (20 mL). The combined organic layers were dried over Na₂SO₄, filtered and the solvent was removed in vacuo. The residue was purified by column chromatography (silica gel, MeOH/DCM/NH₃.H₂O=6:100:1) to give RHY-46 (10 mg) as yellow oil.

RHY-47:

Step 1:
To the solution of RHY (300 mg) in THF (10 mL), was added NaH (150 mg), followed with 1,7-dibromoheptane (0.53 mL), the mixture was heated up to 50° C., after stirring for 20 hrs, the reaction was quenched with water (20 mL), extracted with DCM (3×30 mL), washed with saturated NaHCO₃ aqueous (30 mL). The combined organic layers were dried over Na₂SO₄, filtered and the solvent was removed in vacuo. The residue was purified by column chromatography (silica gel, MeOH/DCM=1:30) to give ZJ-4-183 (220 mg) as yellow oil.

Step 2:

To the solution of ZJ-4-183 (70 mg) in DMF (1 mL), was added 3-(1H-imidazol-1-yl)propan-1-amine (90 μL), the mixture was heated up to 80° C., after stirring for 20 hrs, the reaction was quenched with saturated NaHCO$_3$ aqueous (10 mL), extracted with DCM (3×10 mL), washed with saturated H$_2$O (20 mL). The combined organic layers were dried over Na$_2$SO$_4$, filtered and the solvent was removed in vacuo. The residue was purified by column chromatography (silica gel, MeOH/DCM/NH$_3$.H$_2$O=6:100:1) to give RHY-47 (15 mg) as yellow oil.

Example 5

Functional and Analytical Assays

Ephrin-A1-Induced EphA4 Cluster Assay

The ability of the Rhy derivatives in inhibiting EphA4 signaling was examined in the EphA4 clustering assay. Rat hippocampal neurons were seeded on 48-well plates coated with poly-D-lysine (50 μg/mL) at 6000 cells per well. Neurons were incubated with Neurobasal medium (Invitrogen) supplemented with 2% B27 (Invitrogen). Neurons at 3 DIV were pretreated with Rhy or the Rhy derivatives for 20 min, followed by pre-clustered ephrin-A1 (0.25 μg/mL) ligand for another 40 min, and fixed with 4% paraformaldehyde. Neurons were then immunostained with anti-EphA4 and anti-Tau-1 antibodies. The cellular imaging and quantification of EphA4 clusters was performed using IN Cell Analyzer 6000 high content assay system (GE Healthcare). EphA4 clusters were quantified by calculating the proportion of total area of EphA4 clusters on axons against Tau positive area. Statistical analysis was performed with one-way ANOVA followed by Newman-Keuls Multiple Comparison Test (Prism 5 GraphPad Software).

Analytical Detection of Rhy

Identity and amount of Rhy was analyzed using a Waters Acquity UPLC system coupled to an AB SCIEX 4500 QTRAP system equipped with a turbo V source and electrospray ionization (ESI) probe (UPLC-MS/MS). Rhy in acetonitrile (ACN) was separated on a C18 column (BEH C18, 50×2.1 mm, 1.7 μm, 40° C.) with the mobile phase consisted of 0.1% formic acid in water and ACN. Five microliters of sample was injected and eluted by the following program at the flow rate of 0.6 ml/min: 0-4.0 min, 10~35% ACN; 4.0-4.1 min, 100% ACN; 7.0-7.1 min, 100-10% ACN, 7.1-10 min, 10% ACN. Detection of Rhy was carried out with the positive ionization mode. The ESI conditions were as follows: declustering potential 120 V, entrance potential 10 V, collision cell exit potential 12 V, collision energies 38 V, curtain gas 50 (arbitrary units), collision gas 10 (arbitrary units), ion spray voltage 4500 kV, source temperature 500° C., ion source gas 1:45 (arbitrary units), ion source gas 2:60 (arbitrary units). Multiple-reaction-monitoring (MRM) was used to determine and measure Rhy by three pairs of parent/daughter ions at m/z 385.1→353.1, 385.1→269.1, 385.1→160.1. Under this condition, the retention time of Rhy is 2.56 min.

In Vitro Stability Assay for Rhy

Rhy of 3 μM in acetonitrile (ACN) was added into serum prepared from C57Bl/6 mouse, and the mixture was incubated at various time intervals. Incubation was terminated by the addition of ACN. The mixture was spun down and half of the supernatant was air-dried. The residue was redissolved in ACN and injected into the UPLC-MS/MS system.

Blood and Brain Penetration Assay for Rhy

Male C57Bl/6 mice (16-week-old) were obtained from the Hong Kong University of Science and Technology (HKUST) Animal Care Facility and acclimatized in the laboratory a week before the study. Rhy (5 mg/mL) was dissolved in water and orally given 50 mg/kg at a volume of 10 mL/kg. The procedures in this study were approved by HKUST Animal Ethics Committee and conducted in accordance with the Code of Practice and Use of Animals for Experimental Purpose.

Terminal blood (K$_2$EDTA tubes) and brain tissues were collected at different time intervals (0, 10, 15, 30, 45, 60, 90, 120, 240, 480 min) after Rhy administration (n=6). Plasma was obtained by centrifuging the blood at 3,800×g at 4° C. for 10 min. Mouse brains were collected after a 30-min cardiac perfusion with 0.9% saline. Whole mouse brain with the addition of 80 μL 0.9% saline was subjected to homogenization for 10 s (Precellys Minilys) at 4000 rpm with ceramic beads. The plasma (80 μL) and brain homogenates of Rhy-administered mouse or with 204 Rhy of desired concentrations (9 data points ranging 2.5-500 ng/mL) were then extracted with ~1 mL methanol and vortexed for 3 min. Samples were centrifuged at 12,000×g at 4° C. for 10 min. The supernatants were transferred to a new tube and the remaining samples were subjected to another extraction. The supernatants obtained from the two extractions were pooled and evaporated to dryness. The dried samples were dissolved in 0.3 mL methanol, vortexed for 30 s followed by ultrasonication for 5 min and centrifuged at 17,900×g for 5 min. The supernatant (80 μL) was transferred into vial for UPLC-MS/MS analysis. $C_{max}$, $T_{max}$ and $t_{1/2}$ of Rhy in mouse plasma and brain were calculated using software Phoenix WinNonlin 6.3. The recovery rate of Rhy from mouse plasma and brain was 82% and 68%, respectively. The $R^2$ value of the standard curves of Rhy in plasma and brain was 0.9987 and 0.9963, respectively.

Example 6

Figure 16:
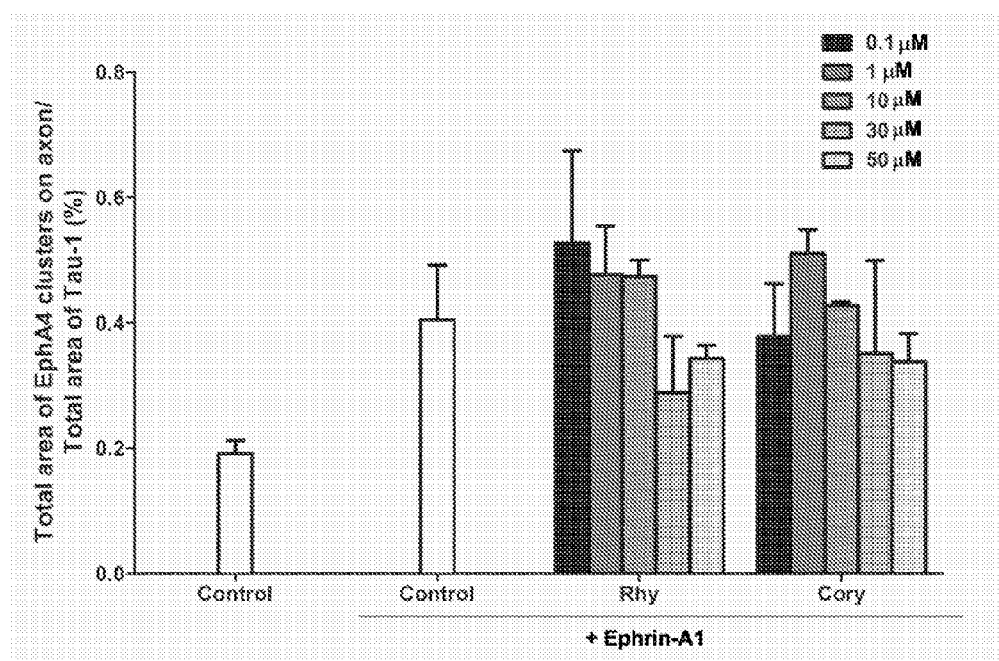
FIG. 16. Rhynchophylline (Rhy) and Corylin (Cory) inhibit Ephrin-A1 induced EphA4 clusters by calculating the proportion of total area of EphA4 clusters on axons against Tau positive area.

Rhynchcophylline and Corylin Inhibit Ephrin-A1-Induced EphA4 Clusters in Cultured Hippocampal Neurons It has been demonstrated that Rhynchophylline (Rhy) and corylin (Cory) are EphA4 inhibitor. The effect of Rhy and Cory on inhibiting EphA4-mediated cellular functions was examined using the ephrin-A1-induced EphA4 cluster assay. Neurons were pretreated with Rhy or Cory for 20 min, which was then followed with pre-clustered ephrin-A1 for another 40 min. The neurons were stained for EphA4 and Tau-1 antibodies. EphA4 clusters were quantified by calculating the proportion of total area of EphA4 clusters on axons against Tau positive area. As shown in FIG. 16, Rhy and Cory reduced the ephrin-A1-induced EphA4 clustering in cultured hippocampal neurons.

Example 7

Figure 17:
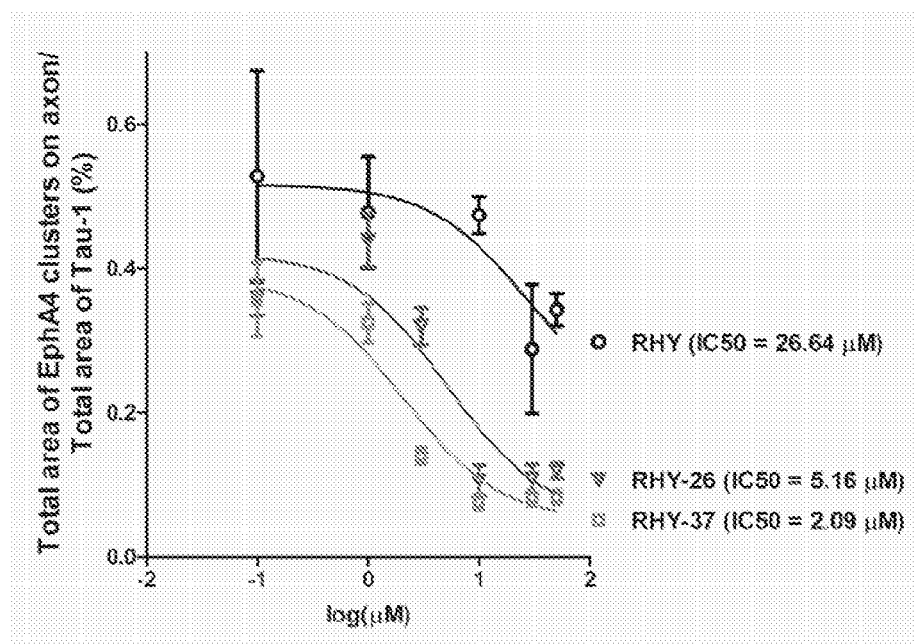
FIG. 17. Novel compounds RHY-26 and RHY-37 exhibit more potent effects on EphA4 inhibition. By calculating the proportion of total area of EphA4 clusters on axons against Tau positive area, the novel compounds RHY-26 and RHY-37 are 5- and 12-fold more potent than Rhy.

Novel Derivatives of Rhy, RHY-26 and RHY-37, Exhibit More Potent EphA4 Inhibition The effect of Rhy and its derivatives on inhibiting EphA4-mediated cellular functions was examined using the ephrin-A1-induced EphA4 cluster assay. Neurons were pretreated with Rhy or the Rhy derivatives for 20 min, which was then followed with pre-clustered ephrin-A1 for another 40 min. The neurons were stained for EphA4 and Tau-1 antibodies. EphA4 clusters were quantified by calculating the proportion of total area of EphA4 clusters on axons against Tau positive area. As shown in FIG. 17, Rhy and its derivatives significantly reduced, in a dose-dependent manner, the ephrin-A1-induced EphA4 clustering in cultured hippocampal neurons. The inhibitory effect of the novel derivatives, RHY-26 and RHY-37, on EphA4 clusters was 5- and 12-fold greater respectively, compared to Rhy.

Example 8

Figure 18:
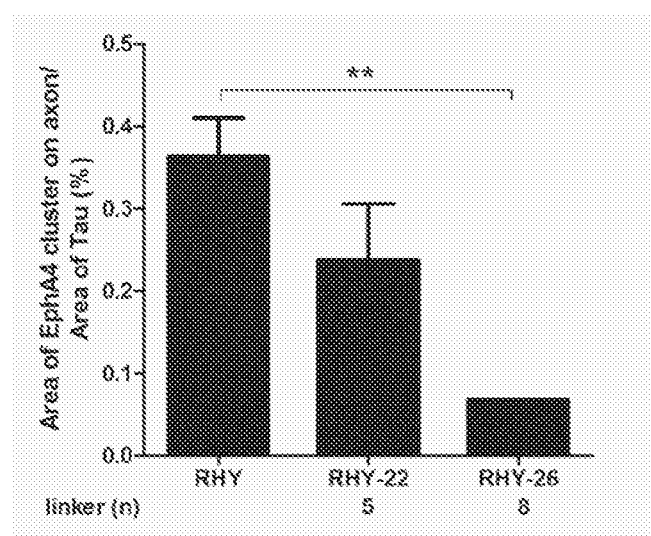
FIG. 18. Novel compound RHY-26 exhibits a potent EphA4 inhibitory effect. By calculating the proportion of total area of EphA4 clusters on axons against Tau positive area, the novel compound RHY-26 significantly reduced EphA4 clusters by ~80%.

Novel Compound RHY-26 Exhibits a More Potent Effect on EphA4 Inhibition than Rhy A group of compounds have been modified from Rhy with the N1 site substituted with a chloro group connected by methylenes. The effect of Rhy, RHY-22 (5-methylene linker), and RHY-26 (8-methylene linker) on inhibiting EphA4-mediated cellular functions was examined using the ephrin-A1-induced EphA4 cluster assay. Neurons were pretreated with Rhy or the Rhy derivatives (30 µM) for 20 min, which was then followed with pre-clustered ephrin-A1 for another 40 min. The neurons were stained for EphA4 and Tau-1 antibodies. As shown in FIG. 18, derivatives with chloro substitutes reduced ephrin-A1-induced EphA4 clustering by ~40-80% in cultured hippocampal neurons when compared to Rhy, indicated that the addition of a chloro group linked to the N1 site of Rhy by methylenes allows increasing the potency on EphA4 inhibition. The potency of RHY-61 (3-methylene linker), RHY-62 (9-methylene linker), RHY-63 (6-methylene linker), RHY-64 (7-methylene linker), RHY-65 (10 methylene linker), RHY-66 (11-methylene linker), and RHY-67 (12-methylene linker) as EphA4 inhibitors is also tested and verified in the same assay system.

Example 9

Figure 19:
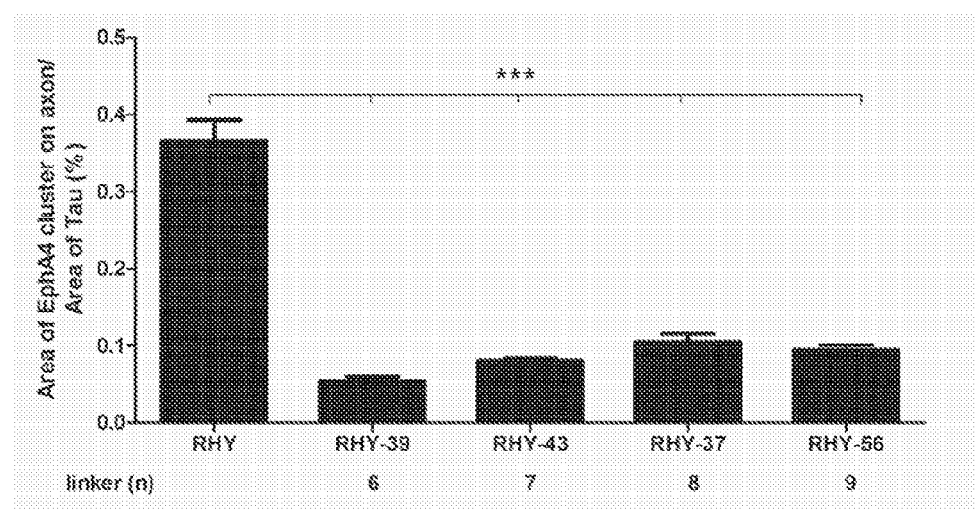
FIG. 19. Novel compounds RHY-39, RHY-43, RHY-37 and RHY-56 exhibit a more potent effect on EphA4 inhibition than Rhy. By calculating the proportion of total area of EphA4 clusters on axons against Tau positive area, the novel compounds with modification of 3,4-dimethoxy-phenoxy at N₁ of Rhy linked by methylenes (n) significantly reduced the EphA4 clusters when compared to Rhy.

Novel Compounds RHY-37, RHY-39, RHY-43, RHY-56 Exhibit a More Potent Effect on EphA4 Inhibition than Rhy A group of compounds have been modified from Rhy with the $N_1$ site substituted with a 3,4-dimethoxy-phenoxy group connected by methylenes. The effect of Rhy, RHY-39 (6-methylene linker), RHY-43 (7-methylene linker), RHY-37 (8-methylene linker), and RHY-56 (9-methylene linker) on inhibiting EphA4-mediated cellular functions was examined using the ephrin-A1-induced EphA4 cluster assay. Neurons were pretreated with Rhy or the Rhy derivatives (30 µM) for 20 min, which was then followed with pre-clustered ephrin-A1 for another 40 min. The neurons were stained for EphA4 and Tau-1 antibodies. As shown in FIG. 19, RHY-39, RHY-43, and RHY-37 and RHY-56 significantly reduced the ephrin-A1-induced EphA4 clustering by ~70-80% in cultured hippocampal neurons when compared to Rhy, indicating that the addition of a 6 to 9 methylene-linked 3,4-dimethoxy-phenoxy group at the $N_1$ site of Rhy allows increasing the potency on EphA4 inhibition.

Example 10

Figure 20:
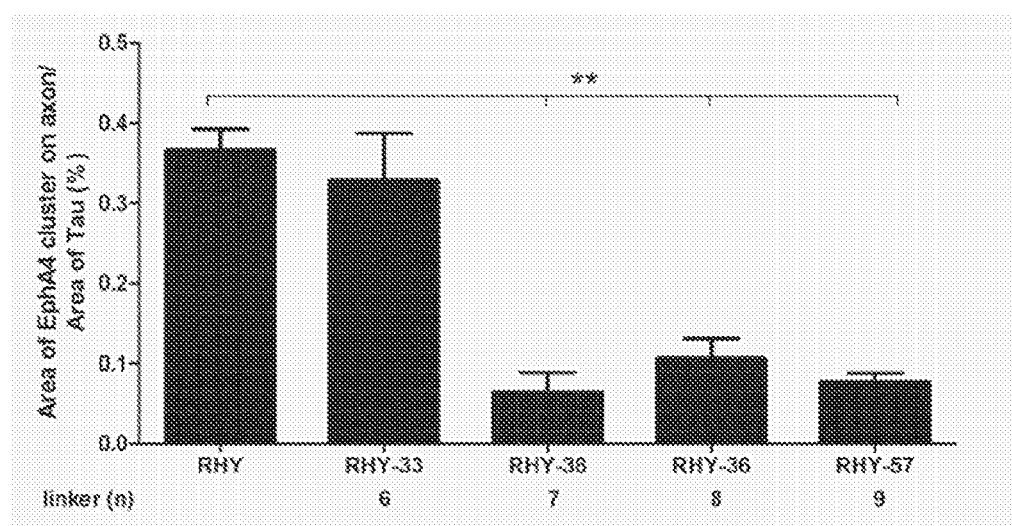
FIG. 20. Novel compounds RHY-38, RHY-36, RHY-57 exhibit a more potent effect on EphA4 inhibition than Rhy. By calculating the proportion of total area of EphA4 clusters on axons against Tau positive area, the novel compounds with modification of dimethoxybenzoate at $N_1$ of Rhy linked by methylenes (n) significantly reduced the EphA4 clusters when compared to Rhy.

Novel Compounds RHY-38, RHY-36, RHY-57 Exhibit a More Potent Effect on EphA4 Inhibition than Rhy A group of compounds have been modified from Rhy with the $N_1$ site substituted with dimethoxybenzoate connected by methylenes. The effect of Rhy, RHY-33 (6-methylene linker), RHY-38 (7-methylene linker), RHY-36 (8-methylene linker) and RHY-57 (9-methylene linker) on inhibiting EphA4-mediated cellular functions was examined using the ephrin-A1-induced EphA4 cluster assay. Neurons were pretreated with Rhy or the Rhy derivatives (50 µM) for 20 min, which was then followed with pre-clustered ephrin-A1 for another 40 min. The neurons were stained for EphA4 and Tau-1 antibodies. As shown in FIG. 20, all the compounds with this modification reduced the ephrin-A1-induced EphA4 clustering by ~20-80% in cultured hippocampal neurons. RHY-38, RHY-36, and RHY-57 exhibited more potent activity than Rhy, and RHY-33 showed comparable potency as Rhy, indicating that the addition of a 6-9 methylene-linked dimethoxybenzoate allows maintaining or increasing the potency on EphA4 inhibition.

Example 11

Figure 21:
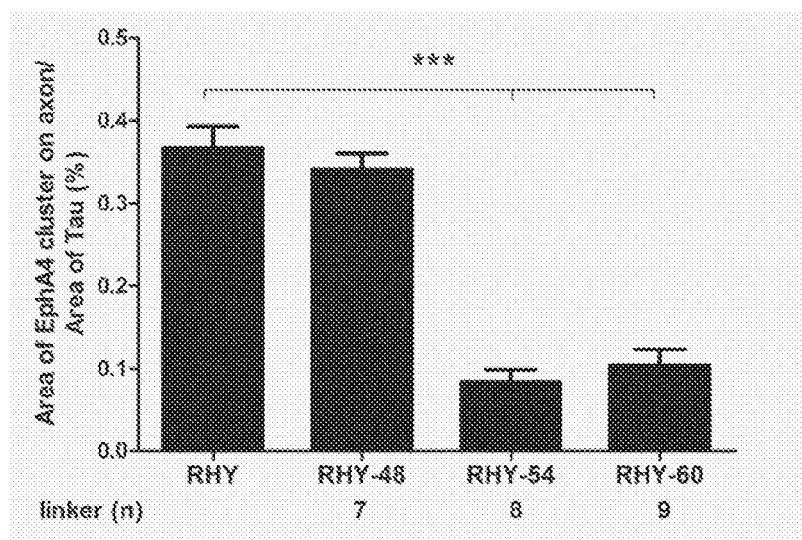
FIG. 21. Novel compounds RHY-54 and RHY-60 exhibits a more potent effect on EphA4 inhibition than Rhy. By calculating the proportion of total area of EphA4 clusters on axons against Tau positive area, the novel compounds with modification of a hydroxyl-phenoxy group at $N_1$ of Rhy linked by methylenes (n) significantly reduced the EphA4 clusters when compared to Rhy.

Novel Compounds RHY-54 and RHY-60 Exhibits a More Potent Effect on EphA4 Inhibition than Rhy A group of compounds have been modified from Rhy with the $N_1$ site substituted with dimethoxybenzoate connected by methylenes. The effect of Rhy, RHY-48 (7-methylene linker), RHY-54 (8-methylene linker) and RHY-60 (9-methylene linker) on inhibiting EphA4-mediated cellular functions was examined using the ephrin-A1-induced EphA4 cluster assay. Neurons were pretreated with Rhy or the derivatives (30 µM) for 20 min, which was then followed with pre-clustered ephrin-A1 for another 40 min. The neurons were stained for EphA4 and Tau-1 antibodies. As shown in FIG. 21, compounds with this group of modification showed inhibitory effect on ephrin-A1-induced EphA4 clustering with RHY-54 and RHY60 significantly more potent than Rhy, with RHY-48 showing comparable potency to Rhy, indicating that the addition of a methylene-linked hydroxyl-phenoxy group at $N_1$ of Rhy allows maintaining or increasing the potency on EphA4 inhibition.

Example 12

Figure 22:
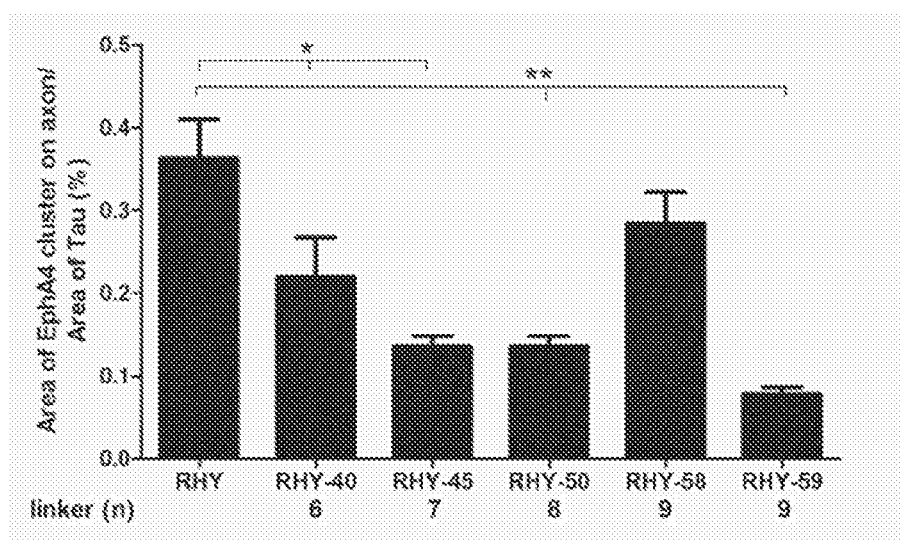
FIG. 22. Novel compounds RHY-40, RHY-45, RHY-50 and RHY-59 exhibit a higher potency on EphA4 inhibition than Rhy. By calculating the proportion of total area of EphA4 clusters on axons against Tau positive area, the novel compounds with modification of a methoxy-nitro benzoate or methoxy-phenyl acrylic acid linked to $N_1$ site of Rhy by methylenes (n) significantly reduced EphA4 clusters when compared to Rhy.

Novel Compounds RHY-40, RHY-45, RHY-50, RHY-59 Exhibit More Potent Effects on EphA4 Inhibition than Rhy A group of compounds have been modified from Rhy with the $N_1$ site substituted with a methoxy-nitro benzoate or methoxy-phenyl acrylic acid connected by methylenes. The effect of Rhy, RHY-40 (6-methylene linker), RHY-45 (7-methylene linker), RHY-50 (8-methylene linker), RHY-58 and RHY-59 (9-methylene linker) on inhibiting EphA4-mediated cellular functions was examined using the ephrin-A1-induced EphA4 cluster assay. Neurons were pretreated with Rhy or the Rhy derivatives (30 µM) for 20 min, which was then followed with pre-clustered ephrin-A1 for another 40 min. The neurons were stained for EphA4 and Tau-1 antibodies. As shown in FIG. 22, all the compounds reduced ephrin-A1-induced EphA4 clustering by ~30-60% in cultured hippocampal neurons. When compared to Rhy, RHY-40, RHY-45, RHY-50, and RHY-59 are being more potent, indicating that the addition of a methylene-linked methoxy-nitro benzoate or methoxy-phenyl acrylic acid at $N_1$ site of Rhy allows increasing the potency on EphA4 inhibition.

Example 13

Figure 23:
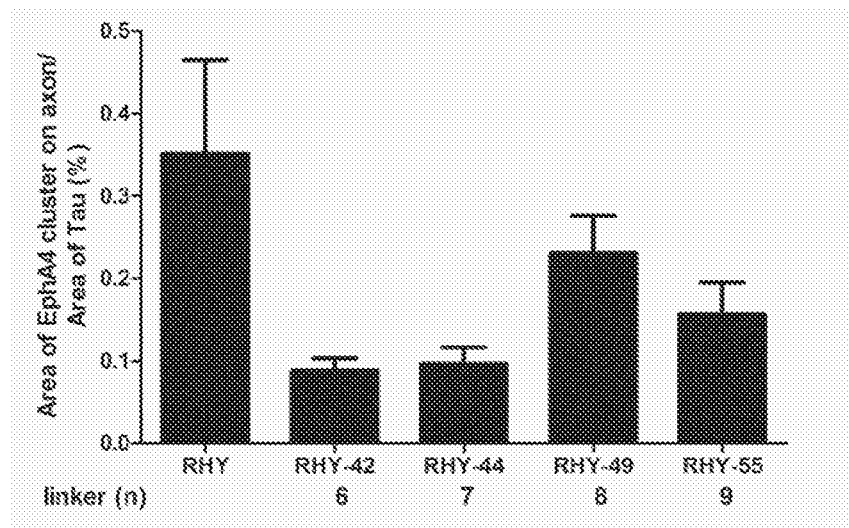
FIG. 23. Novel compounds RHY-42, RHY-44, RHY-49 and RHY-55 exhibit a higher potency on EphA4 inhibition. By calculating the proportion of total area of EphA4 clusters on axons against Tau positive area, novel compounds with modification of benzyloxy-phenoxy group at $N_1$ of Rhy linked by methylenes significantly reduced the EphA4 clusters when compared to Rhy.

Novel Compounds RHY-42, RHY-44, RHY-49 and RHY-55 Exhibit EphA4 Inhibition Activity A group of compounds have been modified from Rhy with the $N_1$ site substituted with a benzyloxy-phenoxy group connected by methylenes. The effect of Rhy, RHY-42 (6-methylene linker), RHY-44 (7-methylene linker), RHY-49 (8-methylene linker), and RHY-55 (9-methylene linker) on inhibiting EphA4-mediated cellular functions was examined using the ephrin-A1-induced EphA4 cluster assay. Neurons were pretreated with Rhy or the Rhy derivatives (30 μM) for 20 min, which was then followed with pre-clustered ephrin-A1 for another 40 min. The neurons were stained for EphA4 and Tau-1 antibodies. As shown in FIG. 23, compounds with this modification reduced the ephrin-A1-induced EphA4 clustering by ~40-60% in cultured hippocampal neuron, indicating that the addition of a methylene-linked benzyloxy-phenoxy group allows increasing the potency on EphA4 inhibition.

Example 14

Figure 24:
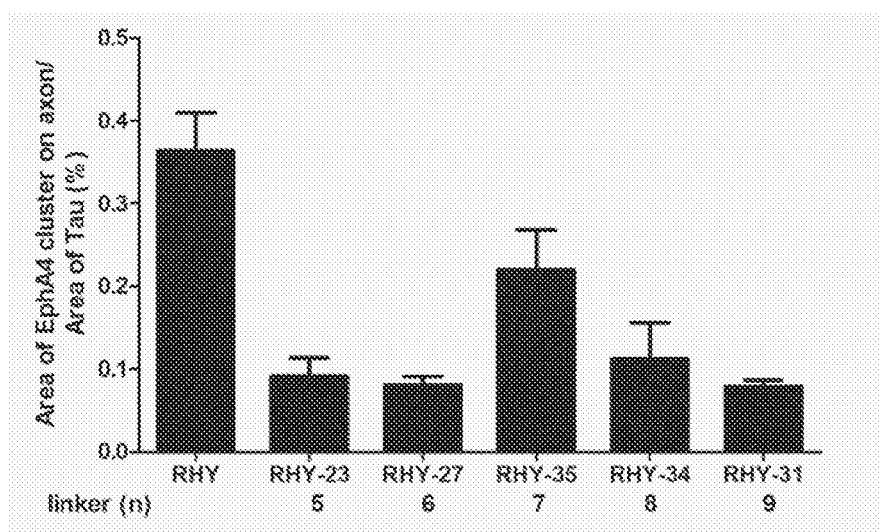
FIG. 24. Novel compounds RHY-23, 27, RHY-35, RHY-34, RHY-31 exhibit a higher potency on EphA4 inhibition. By calculating the proportion of total area of EphA4 clusters on axons against Tau positive area, novel compounds with modification of bromo group at $N_1$ of Rhy linked by methylenes (n) reduced the EphA4 clusters when compared to Rhy.

Novel RHY Derivatives with Bromo-Substitute Exhibit a More Potent Effect on EphA4 Inhibition than Rhy A group of compounds have been modified from Rhy with the $N_1$ site substituted with a bromo group connected by methylenes. The effect of Rhy, RHY-23 (5-methylene linker), RHY-27 (6-methylene linker), RHY-35 (7-methylene linker), RHY-34 (8-methylene linker), and RHY-31 (9-methylene linker) on inhibiting EphA4-mediated cellular functions was examined using the ephrin-A1-induced EphA4 cluster assay. Neurons were pretreated with Rhy or the Rhy derivatives (30 μM) for 20 min, which was then followed with pre-clustered ephrin-A1 for another 40 min. The neurons were stained for EphA4 and Tau-1 antibodies. As shown in FIG. 24, modification with bromo-group at $N_1$ site of Rhy reduced the ephrin-A1-induced EphA4 clustering by ~50-70% in cultured hippocampal neurons when compared to Rhy, indicating that the addition of a 5-9 methylene-linked bromo group at $N_1$ site of Rhy allows increasing the potency on EphA4 inhibition.

Example 15

Figure 25:
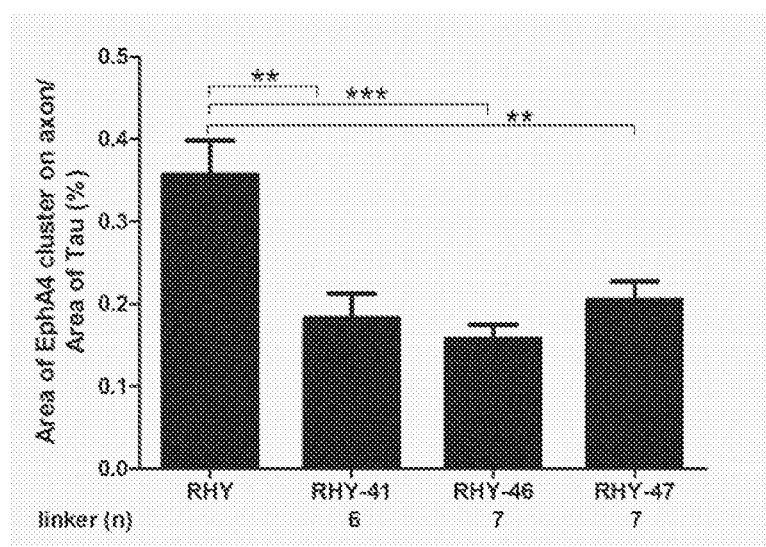
FIG. 25. Novel compound RHY-41, 46 and 47 exhibit a higher potency on EphA4 inhibition. By calculating the proportion of total area of EphA4 clusters on axons against Tau positive area, novel compounds with modification of pyrrolidin-1-yl-ethylamino or imidazole-1-yl-propylamino group at $N_1$ of Rhy linked by methylenes significantly reduced the EphA4 clusters when compared to Rhy.

Novel RHY Derivatives with Substitutes Contain Amino Group Exhibit a More Potent Effect on EphA4 Inhibition than Rhy A group of compounds have been modified from Rhy with the $N_1$ site substituted with a pyrrolidin-1-yl-ethylamino or imidazole-1-yl-propylamino group connected by methylenes. The effect of Rhy, RHY-41 (6-methylene linker), RHY-46 (7-methylene linker), RHY-53 (8-methylene linker) or RHY-47 (7-methylene linker) on inhibiting EphA4-mediated cellular functions was examined using the ephrin-A1-induced EphA4 cluster assay. Neurons were pretreated with Rhy or the Rhy derivatives (50 μM) for 20 min, which was then followed with pre-clustered ephrin-A1 for another 40 min. The neurons were stained for EphA4 and Tau-1 antibodies. As shown in FIG. 25, modification with pyrrolidin-1-yl-ethylamino or imidazole-1-yl-propylamino group at $N_1$ site of Rhy reduced the ephrin-A1-induced EphA4 clustering by ~40-50% in cultured hippocampal neurons, indicating that the addition of these groups of moieties linked with 5-9 methylenes allows increasing the potency on EphA4 inhibition. The potency of RHY-53 (8-methylene linker) as an EphA4 inhibitor is also tested and verified in the same assay system.

Example 16

Figure 26:
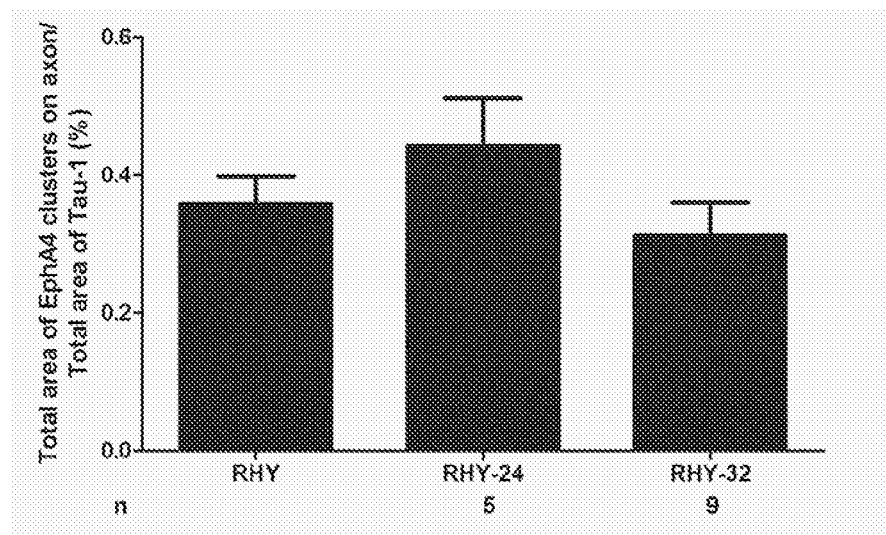
FIG. 26. Novel compound RHY-32 exhibits a higher potency on EphA4 inhibition. By calculating the proportion of total area of EphA4 clusters on axons against Tau positive area, novel compounds with modification of amino-hexylamino group at $N_1$ of Rhy linked by methylenes significantly reduced the EphA4 clusters when compared to Rhy.

Novel RHY Derivatives with Amino-Hexylamino Group Exhibit a More Potent Effect on EphA4 Inhibition than Rhy A group of compounds have been modified from Rhy with the $N_1$ site substituted with a amino-hexylamino group connected by methylenes. The effect of Rhy, RHY-24 (5-methylene linker) and RHY-32 (9-methylene linker) on inhibiting EphA4-mediated cellular functions was examined using the ephrin-A1-induced EphA4 cluster assay. Neurons were pretreated with Rhy or the Rhy derivatives (50 μM) for 20 min, which was then followed with pre-clustered ephrin-A1 for another 40 min. The neurons were stained for EphA4 and Tau-1 antibodies. As shown in FIG. 26, modification with amino-hexylamino group at $N_1$ site of Rhy reduced the ephrin-A1-induced EphA4 clustering by ~20% in cultured hippocampal neurons, indicating that the addition of a 5-9 or 6-9 methylene-linked amino-hexylamino group allows maintaining or increasing the potency on EphA4 inhibition.

Example 17

Figure 27:
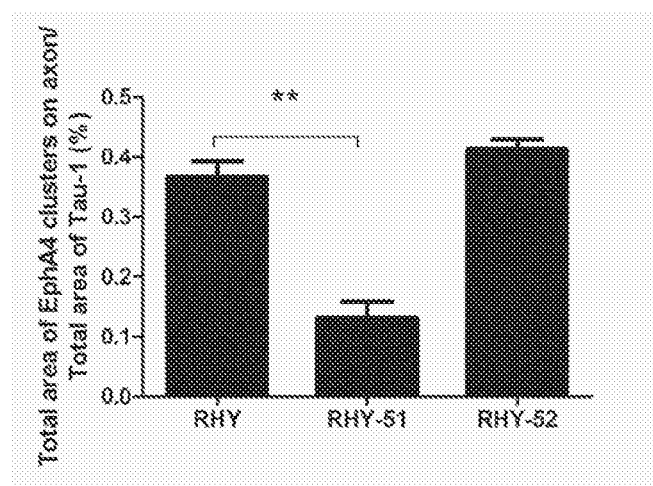
FIG. 27. Novel compound RHY-51 exhibits a higher potency on EphA4 inhibition than Rhy. By calculating the proportion of total area of EphA4 clusters on axons against Tau positive area, novel compounds with iodo-benzoate or iodo-bromo-benzoate at $N_1$ of Rhy linked by methylenes significantly reduced the EphA4 clusters when compared to Rhy.

Novel RHY-51 and RHY-52 Exhibit a More Potent Effect on EphA4 Inhibition than Rhy A group of compounds have been modified from Rhy with the $N_1$ site substituted with a iodo-benzoate or iodo-bromo-benzoate connected by methylenes. The effect of Rhy, RHY-51 (iodo-benzoate with 8-methylene linker) and RHY-52 (iodo-bromo-benzoate with 8-methylene linker) on inhibiting EphA4-mediated cellular functions was examined using the ephrin-A1-induced EphA4 cluster assay. Neurons were pretreated with Rhy or the Rhy derivatives (30 μM) for 20 min, which was then followed with pre-clustered ephrin-A1 for another 40 min. The neurons were stained for EphA4 and Tau-1 antibodies. As shown in FIG. 27, these modifications with at $N_1$ site of Rhy reduced the ephrin-A1-induced EphA4 clustering by ~20-70% in cultured hippocampal neurons, indicating that the addition of these groups of moieties linked with methylenes allows maintaining or in increasing the potency on EphA4 inhibition.

Example 18

Figure 28:
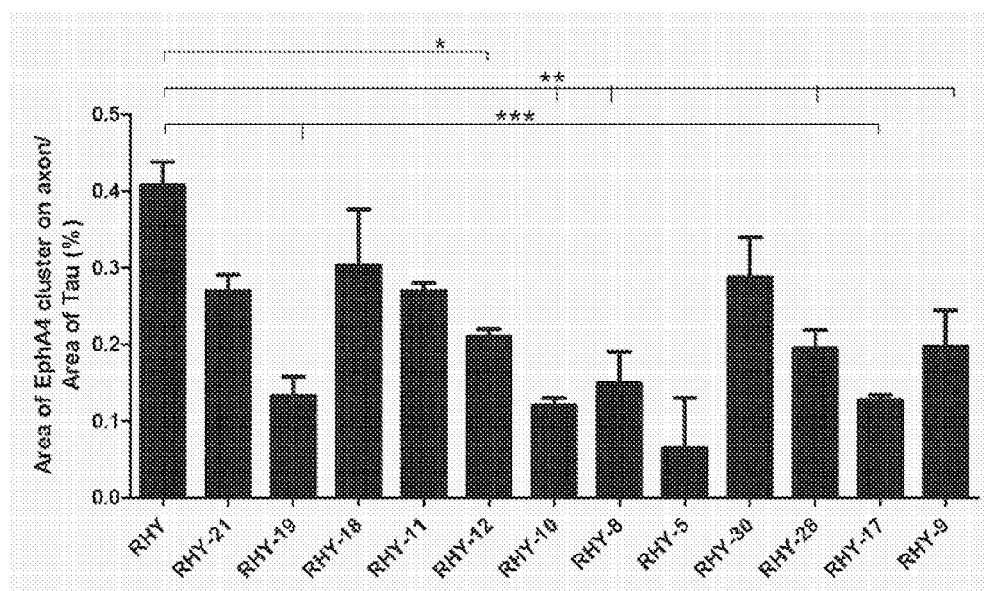
FIG. 28. All the compounds showed inhibitory effect on EphA4 cluster formation. By calculating the proportion of total area of EphA4 clusters on axons against Tau positive area, novel compounds RHY-10, RHY-28, RHY-9, RHY-19, RHY-5, RHY-17 significantly reduced the EphA4 clusters compared to Rhy.

Modification of $N_1$ of Rhy Exhibit a More Potent Effect on EphA4 Inhibition than Rhy A group of compounds modified from Rhy, substituted at $N_1$ site with 4-benzoylbenzyl (RHY-21), 3-chloro-benzyl (RHY-19), methyl (RHY-18), 4-methyl-benzyl (RHY-11), 4-methoxy-benzyl (RHY-12), biphenyl-2-ylmethyl (RHY-10), 2,6-dichloro-benzyl (RHY-8), 4-bromo-benzyl (RHY-5), benzoyl (RHY-30), (4-methoxy-phenyl)-ethanone (RHY-28), allyl (RHY-17), phenyl-allyl (RHY-9), pyridine-2-ylmethyl (RHY-15), pyridine-3-ylmethyl (RHY-14), or pyridine-4-ylmethyl (RHY-16) was examined for their abilities on inhibiting EphA4-mediated cellular functions using the ephrin-A1-induced EphA4 cluster assay. Neurons were pretreated with Rhy or the Rhy derivatives (50 μM) for 20 min, which was then followed with pre-clustered ephrin-A1 for another 40 min. The neurons were stained for EphA4 and Tau-1 antibodies. As shown in FIG. 28, all the compounds showed inhibitory effect on EphA4 cluster formation where RHY-10, RHY-28, RHY-9, RHY-19, RHY-5, RHY-17 being the most significant.

Example 19

Figure 29:
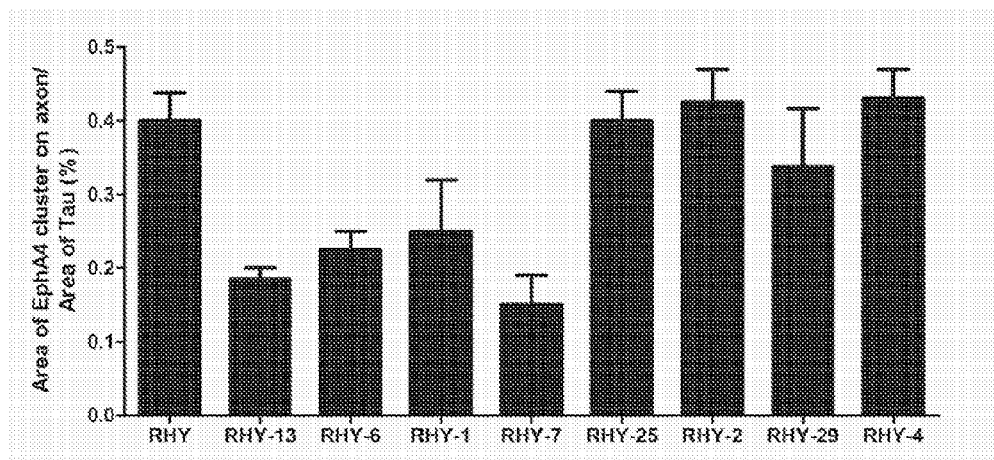
FIG. 29. All the compounds showed inhibitory effect on EphA4 cluster formation. By calculating the proportion of total area of EphA4 clusters on axons against Tau positive area, novel compounds RHY-13, RHY-6, RHY-1 and RHY-7 significantly reduced the EphA4 clusters compared to Rhy.

Novel Compounds RHY-13, RHY-6, RHY-1, RHY-7 Significantly Reduced the EphA4 Clusters Compared to Rhy A group of compounds modified from Rhy, substituted at $N_1$ site with methyl-(RHY-13), benzyl- (RHY-6), methoxybenzyl (RHY-1), tert-butyl-benzyl (RHY-7) or biotinylated- (RHY-25, RHY-2, RHY-3), dimeric- (RHY-29), dimethylated at C23 (RHY-4) was examined for their abilities on inhibiting EphA4-mediated cellular functions using the ephrin-A1-induced EphA4 cluster assay. Neurons were pretreated with Rhy or the Rhy derivatives (50 μM) for 20 min, which was then followed with pre-clustered ephrin-A1 for another 40 min. The neurons were stained for EphA4 and Tau-1 antibodies. As shown in FIG. 29, all the compounds showed inhibitory effect on EphA4 cluster formation where RHY-13, RHY-6, RHY-1 and RHY-7 being the most prominent.

Example 20

Rhy is Detectable in Brain and Plasma after Oral Administration

The pharmacological activities of Rhy prompted an examination of the accessibility or stability of Rhy in the brain or plasma after systemic administration. To investigate the stability of Rhy, the amount of remaining Rhy was first measured after incubating the compound with mouse serum at different time intervals. Concentrations of Rhy were determined by HPLC-MS/MS analysis. Rhy was detected with three pairs of precursor-product ion peaks with the multiple reaction monitoring mode at a retention time of ~2.56 min. It was found that the concentrations of Rhy remained relatively unchanged in serum for the first 60 min and reduced by ~20% over the 360-min incubation period (FIG. 30A).

Next, it was examined whether Rhy could be detected in mouse plasma and brain after oral administration. Rhy was extracted from plasma and from buffered-saline perfused brain of mice at various time intervals after a single oral administration at 50 mg/kg (in 10 mL/kg). Rhy was readily detected in both plasma and brain at 10 min after administration (FIG. 30B). The concentration of Rhy in plasma peaked at ~0.5 h ($T_{max}$=30.84±2.52 min, $C_{max}$=583.20±32.86 ng/mL) and reduced by 50% at ~1.5 h ($t_{1/2}$=81.12±12.06 min). In the brain, the level of Rhy peaked at ~1 h ($T_{max}$=55.02±9.18 min, $C_{max}$=442.73±27.38 ng/brain) with a $t_{1/2}$ at ~2 h (107.22±27.30 min) (FIG. 30C). After 3 h of administration, the level of Rhy dropped to 10% of $C_{max}$ in both plasma and brain. Taken together, it was demonstrated that after oral administration, Rhy rapidly enters into the systemic circulation from the digestive system and is detected in the blood. Moreover, the compound can pass through the blood-brain barrier and being detected in mouse brain tissues.

Example 21

Corylin Restores the Normal LTP Induction in AD Mouse Model

Figure 31:
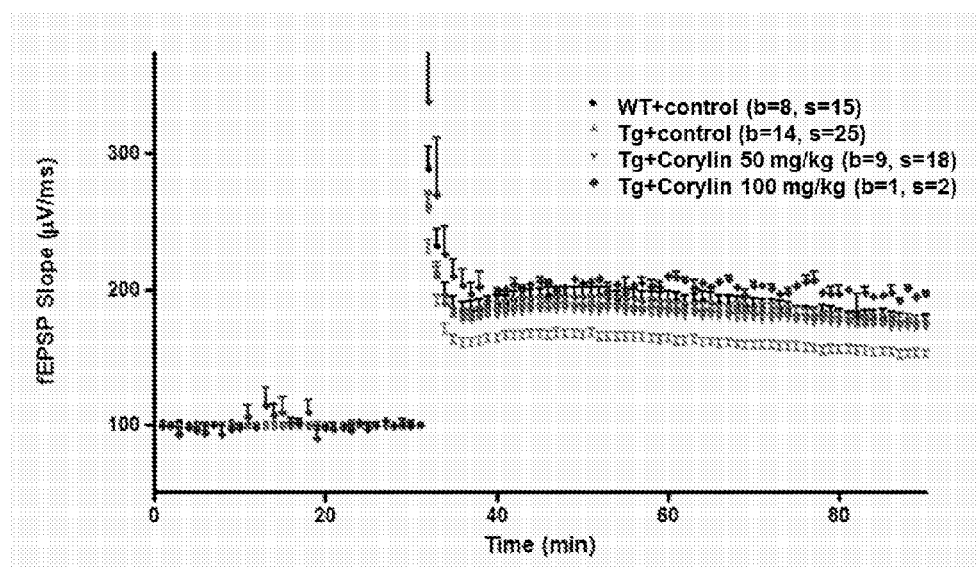
FIG. 31. Corylin rescued the LTP impairment in APP/PS1 mutant mice. WT and APP/PS1 mutant (Tg) mice were orally administered corylin (50-100 mg·kg-1·day-1) or water (control) for 3 weeks, and LTP induced by HFS in the CA1 region of the SC pathway of the hippocampus was measured. The graph showed the averaged slopes of baseline-normalized fEPSP (mean±SEM).

WT and APP/PS1 mutant (Tg) mice were orally administered with corylin (10 mg/mL in water) by daily gavage for 3-4 weeks prior to LTP measurements. LTP induced by 3 trains of HFS (100 Hz for 1 s delivered 30 s apart) in the CA1 region of the SC pathway of the hippocampus was measured. The magnitude of LTP was quantified as the percentage change in the fEPSP slope (10-90%) taken during the 60-min interval after LTP induction. As shown in FIG. 31, impaired LTP was observed in Tg mice (green trace) compared to WT mice (black trace). Treatment of corylin at 50 or 100 mg/kg rescued the LTP impairment in Tg mice and restored to a level comparable to control mice.

Example 22

Rhy Administration Increases Adult Neurogenesis in Hippocampus of APP/PS1 Mouse

Figure 32:
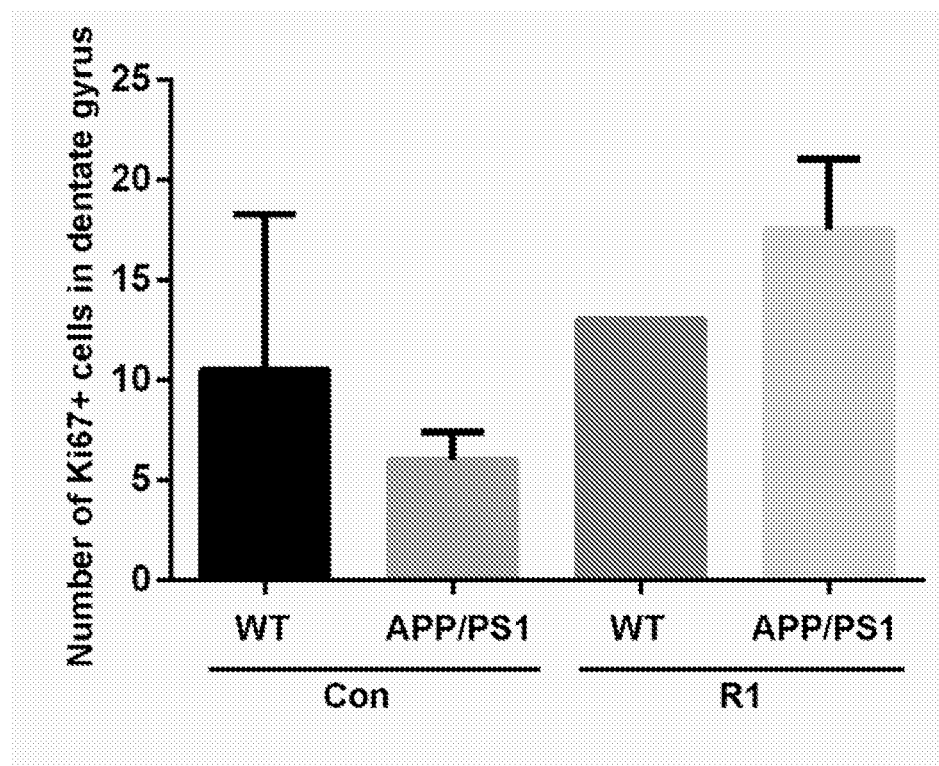
FIG. 32. Rhy administration increases adult neurogenesis in hippocampus of APP/PS1 mice. APP/PS1 mice were orally administered with Rhy (50 mg/kg) for over three months. Rhy (R1) administration increased the number of Ki-67+ neural progenitors in dentate gyrus of hippocampus in APP/PS1 mice.

APP/PS1 mice were orally administered with Rhy (50 mg/kg) for over three months. The mouse brains were sectioned and stained with Ki67 antibody, which labelled all cells in the cell cycle, but not those differentiated progenitors and newly born neurons. As shown in FIG. 32, Rhy (R1) administration increased the number of Ki-67+ neural progenitors in dentate gyms of hippocampus in APP/PS1 mice compared to the control-treated mice.

All patents, patent applications, and other publications, including GenBank Accession Numbers, cited in this application are incorporated by reference in the entirety for all purposes.

REFERENCES

1. Selkoe, D. J. Alzheimer's disease is a synaptic failure. *Science* 298, 789-791 (2002).
2. Walsh, D. M., et al. Naturally secreted oligomers of amyloid [beta] protein potently inhibit hippocampal long-term potentiation in vivo. *Nature* 416, 535-539 (2002).
3. Shankar, G. M., et al. Amyloid-[beta] protein dimers isolated directly from Alzheimer's brains impair synaptic plasticity and memory. *Nat Med* 14, 837-842 (2008).
4. Huang, Y. & Mucke, L. Alzheimer mechanisms and therapeutic strategies. *Cell* 148, 1204-1222 (2012).
5. Lacor, P. N., et al. Synaptic Targeting by Alzheimer's-Related Amyloid β Oligomers. *The Journal of Neuroscience* 24, 10191-10200 (2004).
6. Ting, J. T., Kelley, B. G., Lambert, T. J., Cook, D. G. & Sullivan, J. M. Amyloid precursor protein overexpression depresses excitatory transmission through both presynaptic and postsynaptic mechanisms. *Proc Natl Acad Sci USA* 104, 353-358 (2007).
7. Koffie, R. M., et al. Oligomeric amyloid β associates with postsynaptic densities and correlates with excitatory synapse loss near senile plaques. *Proceedings of the National Academy of Sciences* 106, 4012-4017 (2009).

8. Shankar, G. M., et al. Natural oligomers of the Alzheimer amyloid-beta protein induce reversible synapse loss by modulating an NMDA-type glutamate receptor-dependent signaling pathway. *J Neurosci* 27, 2866-2875 (2007).
9. Li, S., et al. Soluble Oligomers of Amyloid β Protein Facilitate Hippocampal Long-Term Depression by Disrupting Neuronal Glutamate Uptake. *Neuron* 62, 788-801 (2009).
10. Hsieh, H., et al. AMPAR Removal Underlies Aβ-Induced Synaptic Depression and Dendritic Spine Loss. *Neuron* 52, 831-843 (2006).
11. Venkitaramani, D. V., et al. β-Amyloid Modulation of Synaptic Transmission and Plasticity. *The Journal of Neuroscience* 27, 11832-11837 (2007).
12. Snyder, E. M., et al. Regulation of NMDA receptor trafficking by amyloid-beta. *Nat Neurosci* 8, 1051-1058 (2005).
13. Renner, M., et al. Deleterious Effects of Amyloid β Oligomers Acting as an Extracellular Scaffold for mGluR5. *Neuron* 66, 739-754 (2010).
14. Zhao, W.-Q., et al. Insulin Receptor Dysfunction Impairs Cellular Clearance of Neurotoxic Oligomeric Aβ. *Journal of Biological Chemistry* 284, 18742-18753 (2009).
15. Cisse, M., et al. Reversing EphB2 depletion rescues cognitive functions in Alzheimer model. *Nature* 469, 47-52 (2011).
16. Klein, R. Bidirectional modulation of synaptic functions by Eph/ephrin signaling. *Nat Neurosci* 12, 15-20 (2009).
17. Chen, Y., Fu, A. K. & Ip, N. Y. Bidirectional signaling of ErbB and Eph receptors at synapses. *Neuron Glia Biol* 4, 211-221 (2008).
18. Pasquale, E. B. Eph-ephrin bidirectional signaling in physiology and disease. *Cell* 133, 38-52 (2008).
19. Sheffler-Collins, S. I. & Dalva, M. B. EphBs: an integral link between synaptic function and synaptopathies. *Trends in Neurosciences* 35, 293-304 (2012).
20. Dalva, M. B., et al. EphB receptors interact with NMDA receptors and regulate excitatory synapse formation. *Cell* 103, 945-956 (2000).
21. Murai, K. K. & Pasquale, E. B. Eph receptors and ephrins in neuron-astrocyte communication at synapses. *Glia* 59, 1567-1578 (2011).
22. Pasquale, E. B. Eph receptor signalling casts a wide net on cell behaviour. *Nat Rev Mol Cell Biol* 6, 462-475 (2005).
23. Bourgin, C., Murai, K. K., Richter, M. & Pasquale, E. B. The EphA4 receptor regulates dendritic spine remodeling by affecting beta1-integrin signaling pathways. *J Cell Biol* 178, 1295-1307 (2007).
24. Fu, W. Y., et al. Cdk5 regulates EphA4-mediated dendritic spine retraction through an ephexin1-dependent mechanism. *Nat Neurosci* 10, 67-76 (2007).
25. Richter, M., Murai, K. K., Bourgin, C., Pak, D. T. & Pasquale, E. B. The EphA4 receptor regulates neuronal morphology through SPAR-mediated inactivation of Rap GTPases. *J Neurosci* 27, 14205-14215 (2007).
26. Chen, Y., Fu, A. K. Y. & Ip, N. Y. Eph receptors at synapses: Implications in neurodegenerative diseases. *Cellular Signalling* 24, 606-611 (2012).
27. Fu, A. K., et al. APC(Cdh1) mediates EphA4-dependent downregulation of AMPA receptors in homeostatic plasticity. *Nat Neurosci* 14, 181-189 (2011).
28. Simon, A. M., et al. Early changes in hippocampal Eph receptors precede the onset of memory decline in mouse models of Alzheimer's disease. *J Alzheimers Dis* 17, 773-786 (2009).
29. Murai, K. K., Nguyen, L. N., Irie, F., Yamaguchi, Y. & Pasquale, E. B. Control of hippocampal dendritic spine morphology through ephrin-A3/EphA4 signaling. *Nat Neurosci* 6, 153-160 (2003).
30. Sheng, M., Sabatini, B. L. & Sudhof, T. C. Synapses and Alzheimer's disease. *Cold Spring Harb Perspect Biol* 4 (2012).
31. Jacobsen, J. S., et al. Early-onset behavioral and synaptic deficits in a mouse model of Alzheimer's disease. *Proceedings of the National Academy of Sciences of the United States of America* 103, 5161-5166 (2006).
32. Bowden, T. A., et al. Structural Plasticity of Eph Receptor A4 Facilitates Cross-Class Ephrin Signaling. *Structure* 17, 1386-1397 (2009).
33. Murai, K. K., et al. Targeting the EphA4 receptor in the nervous system with biologically active peptides. *Mol Cell Neurosci* 24, 1000-1011 (2003).
34. Lacor, P. N., et al. Abeta oligomer-induced aberrations in synapse composition, shape, and density provide a molecular basis for loss of connectivity in Alzheimer's disease. *J Neurosci* 27, 796-807 (2007).
35. Noberini, R., et al. Small molecules can selectively inhibit ephrin binding to the EphA4 and EphA2 receptors. *J Biol Chem* 283, 29461-29472 (2008).
36. Lambert, M. P., et al. Diffusible, nonfibrillar ligands derived from Aβ1-42 are potent central nervous system neurotoxins. *Proceedings of the National Academy of Sciences* 95, 6448-6453 (1998).
37. Qin, H., et al. Structural characterization of the EphA4-Ephrin-B2 complex reveals new features enabling Eph-ephrin binding promiscuity. *J Biol Chem* 285, 644-654 (2010).
38. Singla, N., et al. Crystal structure of the ligand-binding domain of the promiscuous EphA4 receptor reveals two distinct conformations. *Biochemical and Biophysical Research Communications* 399, 555-559 (2010).
39. Qin, H., Shi, J., Noberini, R., Pasquale, E. B. & Song, J. Crystal structure and NMR binding reveal that two small molecule antagonists target the high affinity ephrin-binding channel of the EphA4 receptor. *J Biol Chem* 283, 29473-29484 (2008).
40. Zhou, J. & Zhou, S. Antihypertensive and neuroprotective activities of rhynchophylline: The role of rhynchophylline in neurotransmission and ion channel activity. *Journal of Ethnopharmacology* 132, 15-27 (2010).
41. Noberini, R., Koolpe, M., Lamberto, I. & Pasquale, E. B. Inhibition of Eph receptor-ephrin ligand interaction by tea polyphenols. *Pharmacol Res* 66, 363-373 (2012).

42. Cameron, B. & Landreth, G. E. Inflammation, microglia, and Alzheimer's disease. *Neurobiol Dis* 37, 503-509 (2010).
43. Shen, L., et al. Whole genome association study of brain-wide imaging phenotypes for identifying quantitative trait loci in MCI and AD: A study of the ADNI cohort. *NeuroImage* 53, 1051-1063 (2010).
44. Logue, M. W., et al. A comprehensive genetic association study of Alzheimer disease in African Americans. *Arch Neurol* 68, 1569-1579 (2011).
45. Carmona, M. A., Murai, K. K., Wang, L., Roberts, A. J. & Pasquale, E. B. Glial ephrin-A3 regulates hippocampal dendritic spine morphology and glutamate transport. *Proc Natl Acad Sci USA* 106, 12524-12529 (2009).
46. Filosa, A., et al. Neuron-glia communication via EphA4/ephrin-A3 modulates LTP through glial glutamate transport. *Nat Neurosci* 12, 1285-1292 (2009).
47. Palop, J. J. & Mucke, L. Amyloid-beta-induced neuronal dysfunction in Alzheimer's disease: from synapses toward neural networks. *Nat Neurosci* 13, 812-818 (2010).
48. Zhou, L., et al. EphA4 signaling regulates phospholipase Cgamma1 activation, cofilin membrane association, and dendritic spine morphology. *J Neurosci* 27, 5127-5138 (2007).
49. Masliah, E., et al. Abnormal Glutamate Transport Function in Mutant Amyloid Precursor Protein Transgenic Mice. *Experimental Neurology* 163, 381-387 (2000).
50. Munro, K. M., Perreau, V. M. & Turnley, A. M. Differential gene expression in the EphA4 knockout spinal cord and analysis of the inflammatory response following spinal cord injury. *PLoS One* 7, e37635 (2012).
51. Noberini, R., Lamberto, I. & Pasquale, E. B. Targeting Eph receptors with peptides and small molecules: progress and challenges. *Semin Cell Dev Biol* 23, 51-57 (2012).
52. Lamberto, I., et al. Distinctive binding of three antagonistic peptides to the ephrin-binding pocket of the EphA4 receptor. *Biochem J* 445, 47-56 (2012).
53. Van Hoecke, A., et al. EPHA4 is a disease modifier of amyotrophic lateral sclerosis in animal models and in humans. *Nat Med* 18, 1418-1422 (2012).
54. Goldshmit, Y., et al. EphA4 blockers promote axonal regeneration and functional recovery following spinal cord injury in mice. *PLoS One* 6, e24636 (2011).
55. Kang, T. H., et al. Rhynchophylline and isorhynchophylline inhibit NMDA receptors expressed in *Xenopus* oocytes. *Eur J Pharmacol* 455, 27-34 (2002).
56. Kang, T. H., et al. Protective effect of rhynchophylline and isorhynchophylline on in vitro ischemia-induced neuronal damage in the hippocampus: putative neurotransmitter receptors involved in their action. *Life Sci* 76, 331-343 (2004).
57. Kawakami, Z., Ikarashi, Y. & Kase, Y. Isoliquiritigenin is a novel NMDA receptor antagonist in kampo medicine yokukansan. *Cell Mol Neurobiol* 31, 1203-1212 (2011).
58. Shen, Y., Fu, W.-Y., Cheng, E. Y. L., Fu, A. K. Y. & Ip, N. Y. Melanocortin-4 Receptor Regulates Hippocampal Synaptic Plasticity through a Protein Kinase A-Dependent Mechanism. *The Journal of Neuroscience* 33, 464-472 (2013).
59. Lambert, M. P., et al. Vaccination with soluble Aβ oligomers generates toxicity-neutralizing antibodies. *Journal of Neurochemistry* 79, 595-605 (2001).
60. Klein, W. L. Aβ toxicity in Alzheimer's disease: globular oligomers (ADDLs) as new vaccine and drug targets. *Neurochemistry International* 41, 345-352 (2002).
61. Shi, L., et al. Alpha2-chimaerin interacts with EphA4 and regulates EphA4-dependent growth cone collapse. *Proc Natl Acad Sci USA* 104, 16347-16352 (2007).
62. Morris, G. M., et al. AutoDock4 and AutoDockTools4: Automated docking with selective receptor flexibility. *J Comput Chem* 30, 2785-2791 (2009).
63. Morris, G. M., et al. Automated docking using a Lamarckian genetic algorithm and an empirical binding free energy function. *Journal of Computational Chemistry* 19, 1639-1662 (1998).
64. Huey, R., Morris, G. M., Olson, A. J. & Goodsell, D. S. A semiempirical free energy force field with charge-based desolvation. *Journal of Computational Chemistry* 28, 1145-1152 (2007).
65. Thomas-Crusells, J., Vieira, A., Saarma, M. & Rivera, C. A novel method for monitoring surface membrane trafficking on hippocampal acute slice preparation. *J Neurosci Methods* 125, 159-166 (2003).
66. Wan, J., et al. Tyk2/STAT3 signaling mediates beta-amyloid-induced neuronal cell death: implications in Alzheimer's disease. *J Neurosci* 30, 6873-6881 (2010).
67. Bouvier, D., et al. EphA4 is localized in clathrin-coated and synaptic vesicles in adult mouse brain. *J Neurochem* 113, 153-165 (2010).
68. Sala, C., et al. Inhibition of dendritic spine morphogenesis and synaptic transmission by activity-inducible protein Homer1a. *J Neurosci* 23, 6327-6337 (2003).
69. Massa, S. M., et al. Small molecule BDNF mimetics activate TrkB signaling and prevent neuronal degeneration in rodents. *J Clin Invest* 120, 1774-1785 (2010).
70. Jo, J., et al. A[beta]1-42 inhibition of LTP is mediated by a signaling pathway involving caspase-3, Akt1 and GSK-3[beta]. *Nat Neurosci* 14, 545-547 (2011).

TABLE 1

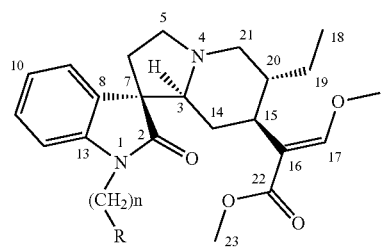

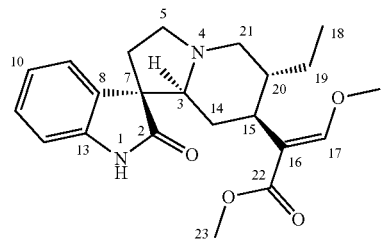

Rhynchophylline (Rhy)

| Cpd | R | Linker (n) | MW | Molecular Formula | $N_1$ substitute |
|---|---|---|---|---|---|
| RHY-61 | Cl | 3 | 460.99 | $C_{25}H_{33}ClN_2O_4$ | Chloro-propyl |
| RHY-22 | Cl | 5 | 489.05 | $C_{27}H_{37}ClN_2O_4$ | Chloro-pentyl |
| RHY-63 | Cl | 6 | 503.07 | $C_{28}H_{39}ClN_2O_4$ | Chloro-hexyl |
| RHY-64 | Cl | 7 | 517.10 | $C_{29}H_{41}ClN_2O_4$ | Chloro-heptyl |
| RHY-26 | Cl | 8 | 531.13 | $C_{30}H_{43}ClN_2O_4$ | Chloro-octyl |
| RHY-62 | Cl | 9 | 545.15 | $C_{31}H_{45}ClN_2O_4$ | Chloro-nonyl |
| RHY-65 | Cl | 10 | 559.18 | $C_{32}H_{47}ClN_2O_4$ | Chloro-decyl |
| RHY-66 | Cl | 11 | 573.21 | $C_{33}H_{49}ClN_2O_4$ | Chloro-undecyl |
| RHY-67 | Cl | 12 | 587.23 | $C_{34}H_{51}ClN_2O_4$ | Chloro-dodecyl |
| RHY-23 | Br | 5 | 533.50 | $C_{27}H_{37}BrN_2O_4$ | Bromo-pentyl |
| RHY-27 | Br | 6 | 547.52 | $C_{28}H_{39}BrN_2O_4$ | Bromo-hexyl |
| RHY-35 | Br | 7 | 561.55 | $C_{29}H_{41}BrN_2O_4$ | Bromo-heptyl |
| RHY-34 | Br | 8 | 575.58 | $C_{30}H_{43}BrN_2O_4$ | Bromo-octyl |
| RHY-31 | Br | 9 | 589.60 | $C_{31}H_{45}BrN_2O_4$ | Bromo-nonyl |
| RHY-33 | 3,4-dimethoxy benzoate | 6 | 648.79 | $C_{37}H_{48}N_2O_8$ | Dimethoxy-benzoate-hexyl |
| RHY-38 | 3,4-dimethoxy benzoate | 7 | 662.81 | $C_{38}H_{50}N_2O_8$ | Dimethoxy-benzoate-heptyl |
| RHY-36 | 3,4-dimethoxy benzoate | 8 | 676.84 | $C_{39}H_{52}N_2O_8$ | Dimethoxy-benzoate-octyl |
| RHY-57 | 3,4-dimethoxy benzoate | 9 | 690.87 | $C_{40}H_{54}N_2O_8$ | Dimethoxy-benzoate-nonyl |
| RHY-39 | 3,4-dimethoxy phenoxy | 6 | 620.78 | $C_{36}H_{48}N_2O_7$ | Dimethoxy-phenoxy-hexyl |
| RHY-43 | 3,4-dimethoxy phenoxy | 7 | 634.80 | $C_{37}H_{50}N_2O_7$ | Dimethoxy-phenoxy-heptyl |
| RHY-37 | 3,4-dimethoxy phenoxy | 8 | 648.83 | $C_{38}H_{52}N_2O_7$ | Dimethoxy-phenoxy-octyl |
| RHY-56 | 3,4-dimethoxy phenoxy | 9 | 662.86 | $C_{39}H_{54}N_2O_7$ | Dimethoxy-phenoxy-nonyl |
| RHY-48 | 4-hydroxy-phenoxy | 7 | 590.75 | $C_{35}H_{46}N_2O_6$ | (4-Hydroxy-phenoxy)-heptyl |
| RHY-54 | 4-hydroxy-phenoxy | 8 | 604.78 | $C_{36}H_{48}N_2O_6$ | (4-Hydroxy-phenoxy)-octyl |
| RHY-60 | 4-hydroxy-phenoxy | 9 | 618.80 | $C_{37}H_{50}N_2O_6$ | (4-Hydroxy-phenoxy)-nonyl |
| RHY-42 | 4-benzyloxy-phenoxy | 6 | 666.85 | $C_{41}H_{50}N_2O_6$ | (4-Benzyloxy-phenoxy)-hexyl |
| RHY-44 | 4-benzyloxy-phenoxy | 7 | 680.87 | $C_{42}H_{52}N_2O_6$ | (4-Benzyloxy-phenoxy)-heptyl |
| RHY-49 | 4-benzyloxy-phenoxy | 8 | 694.90 | $C_{43}H_{54}N_2O_6$ | (4-Benzyloxy-phenoxy)-octyl |
| RHY-55 | 4-benzyloxy-phenoxy | 9 | 706.20 | $C_{44}H_{56}N_2O_6$ | (4-Benzyloxy-phenoxy)-nonyl |
| RHY-40 | 5-methoxy-2-nitro-benzoate | 6 | 663.76 | $C_{36}H_{45}N_3O_9$ | 5-Methoxy-2-nitro-benzoate-hexyl |
| RHY-45 | 5-methoxy-2-nitro-benzoate | 7 | 677.78 | $C_{37}H_{47}N_3O_9$ | 5-Methoxy-2-nitro-benzoate-heptyl |
| RHY-50 | 5-methoxy-2-nitro-benzoate | 8 | 691.81 | $C_{38}H_{49}N_3O_9$ | 5-Methoxy-2-nitro-benzoate-octyl |
| RHY-58 | 5-methoxy-2-nitro-benzoate | 9 | 705.84 | $C_{39}H_{51}N_3O_9$ | 5-Methoxy-2-nitro-benzoate-nonyl |
| RHY-51 | 2-iodo-benzoate | 8 | 742.68 | $C_{37}H_{47}IN_2O_6$ | 2-Iodo-benzoic acid-octyl |
| RHY-52 | 2-iodo-4-bromo-benzoate | 8 | 821.58 | $C_{37}H_{46}BrIN_2O_6$ | 2-Iodo-4-bromo-benzoic acid-octyl |
| RHY-59 | (4-methoxy-phenyl)-acrylic acid | 9 | 686.88 | $C_{41}H_{54}N_2O_7$ | (4-Methoxy-phenyl)-acrylic acid-nonyl |
| RHY-41 | 2-pyrrolidin-1-yl-ethylamino | 6 | 580.80 | $C_{34}H_{52}N_4O_4$ | (2-Pyrrolidin-1-yl-ethylamino)-hexyl |
| RHY-46 | 2-pyrrolidin-1-yl-ethylamino | 7 | 594.83 | $C_{35}H_{54}N_4O_4$ | (2-Pyrrolidin-1-yl-ethylamino)-heptyl |
| RHY-53 | 2-pyrrolidin-1-yl-ethylamino | 8 | 608.85 | $C_{36}H_{56}N_4O_4$ | (2-Pyrrolidin-1-yl-ethylamino)-octyl |
| RHY-47 | 3-imidazol-1-yl-propylamino | 7 | 605.81 | $C_{35}H_{51}N_5O_4$ | (3-Imidazol-1-yl-propylamino)-heptyl |
| RHY-24 | 6-amino-hexylamino | 5 | 568.79 | $C_{33}H_{52}N_4O_4$ | 5-(6-Amino-hexylamino)-pentyl |
| RHY-32 | 6-amino-hexylamino | 9 | 624.90 | $C_{37}H_{60}N_4O_4$ | 5-(6-Amino-hexylamino)-nonyl |

TABLE 2

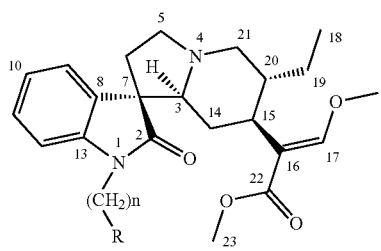

| Cpd | R | Linker (n) | MW | Molecular Formula |
|---|---|---|---|---|
| RHY-18 | methyl | 0 | 398.50 | $C_{23}H_{30}N_2O_4$ |
| RHY-11 | 4-methyl-benzyl | 0 | 488.62 | $C_{30}H_{36}N_2O_4$ |
| RHY-12 | 4-methoxy-benzyl | 0 | 504.62 | $C_{30}H_{36}N_2O_5$ |
| RHY-10 | biphenyl-2-ylmethyl | 0 | 550.69 | $C_{35}H_{38}N_2O_4$ |
| RHY-21 | 4-benzoyl-benzyl | 0 | 578.70 | $C_{36}H_{38}N_2O_5$ |
| RHY-19 | 3-chloro-benzyl | 0 | 509.04 | $C_{29}H_{33}ClN_2O_4$ |
| RHY-8 | 2,6-dichloro-benzyl | 0 | 543.48 | $C_{29}H_{32}Cl_2N_2O_4$ |
| RHY-5 | 4-bromo-benzyl | 0 | 589.95 | $C_{29}H_{34}BrClN_2O_4$ |
| RHY-30 | benzoyl | 0 | 488.57 | $C_{29}H_{32}N_2O_5$ |

TABLE 2-continued

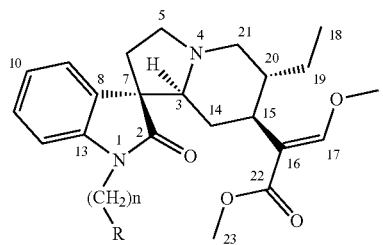

| Cpd | R | Linker (n) | MW | Molecular Formula |
|---|---|---|---|---|
| RHY-28 | (4-methoxy-phenyl)-ethanone | 0 | 532.63 | $C_{31}H_{36}N_2O_6$ |
| RHY-17 | allyl | 0 | 424.53 | $C_{25}H_{32}N_2O_4$ |
| RHY-9 | phenyl-allyl | 0 | 500.63 | $C_{31}H_{36}N_2O_4$ |
| RHY-15 | pyridin-2-ylmethyl | 0 | 475.58 | $C_{28}H_{33}N_3O_4$ |
| RHY-14 | pyridin-3-ylmethyl | 0 | 475.58 | $C_{28}H_{33}N_3O_4$ |
| RHY-16 | pyridin-4-ylmethyl | 0 | 475.58 | $C_{28}H_{33}N_3O_4$ |
| RHY-20 | 3-methyl-1H-quinoxalin-2-one | 0 | 542.63 | $C_{31}H_{34}N_4O_5$ |

TABLE 3

| Cpd | Molecular Structure | MW | Molecular Formula | Modification |
|---|---|---|---|---|
| Rhy | 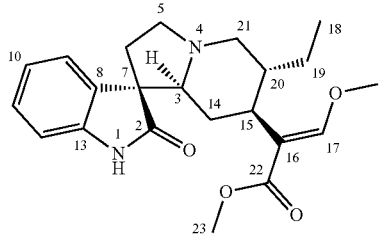 | 384.47 | $C_{22}H_{28}N_2O_4$ | |
| RHY-13 | 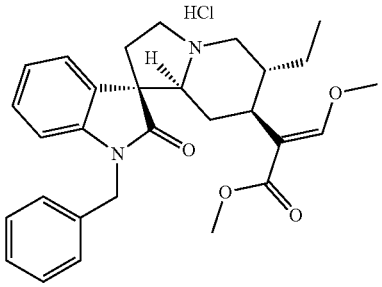 | 413.53 | $C_{24}H_{33}N_2O_4+$ | Methyl at $N_1$ |
| RHY-6 | 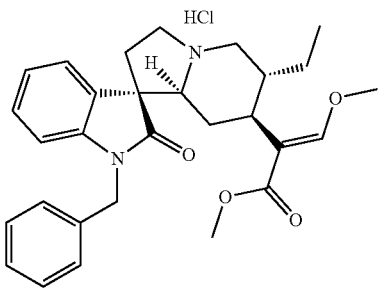 | 511.05 | $C_{29}H_{35}ClN_2O_4$ | Benzyl at $N_1$ |

TABLE 3-continued
| Cpd | Molecular Structure | MW | Molecular Formula | Modification |
|---|---|---|---|---|
| RHY-1 | 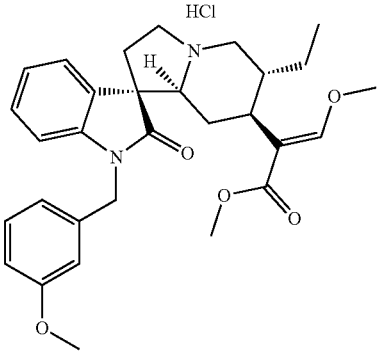 HCl | 541.08 | $C_{30}H_{37}ClN_2O_5$ | 3-Methoxy-benzyl |
| RHY-7 | 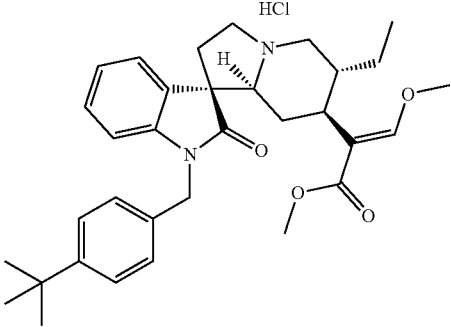 HCl | 567.16 | $C_{33}H_{43}ClN_2O_4$ | 4-tert-Butyl-benzyl |
| RHY-25 | 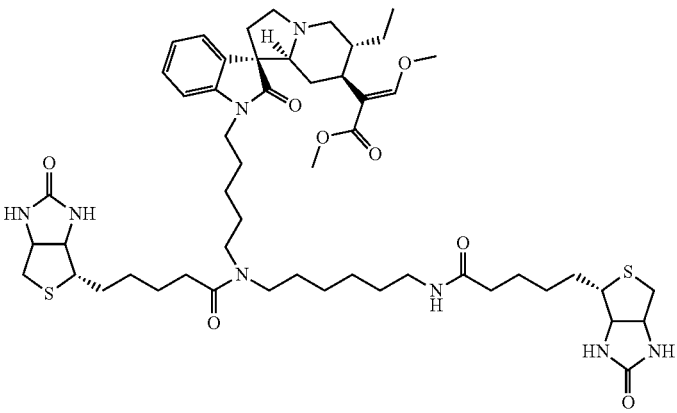 | 1021.38 | $C_{53}H_{80}N_8O_8S_2$ | Biotinylation at $N_1$ |
| RHY-2 | 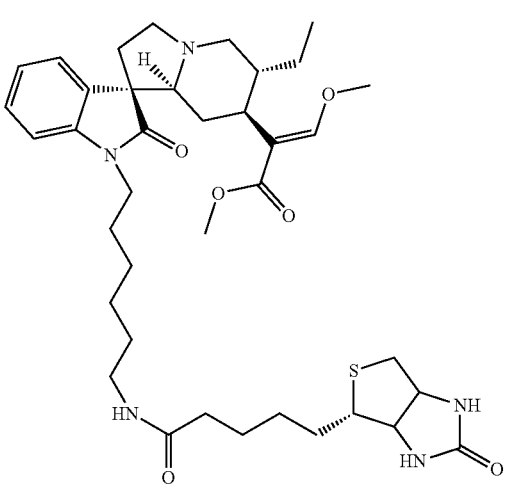 | 709.94 | $C_{38}H_{55}N_5O_6S$ | Biotinylation at $N_1$ |

TABLE 3-continued

| Cpd | Molecular Structure | MW | Molecular Formula | Modification |
|---|---|---|---|---|
| RHY-29 | 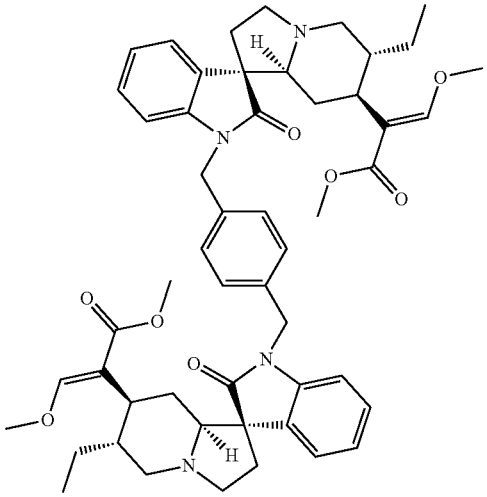 | 871.07 | $C_{52}H_{62}N_4O_8$ | |
| RHY-4 | 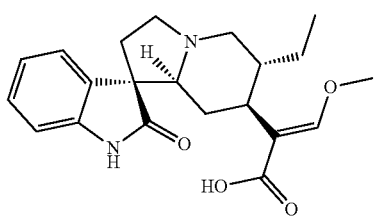 | 370.44 | $C_{21}H_{26}N_2O_4$ | Demethylation at C23 |
| RHY-3 | 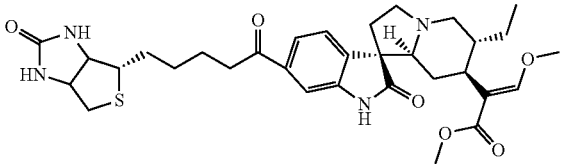 | 610.76 | $C_{32}H_{42}N_4O_6S$ | Biotinylation at C11 |

What is claimed is:

1. A compound of Formula I:

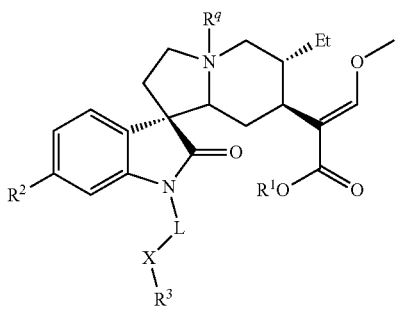

I or a pharmaceutically acceptable salt thereof; wherein
each $R^1$ is a member independently selected from the group consisting of hydrogen and alkyl;
each $R^2$ is a member independently selected from the group consisting of hydrogen and acyl;
each $R^q$ is a member independently selected from the group consisting of an electron pair, lower alkyl, allyl, and arylmethyl;

L is an alkylene;
X is selected from the group consisting of a bond, —O—, —S—, and —N($R^4$)—;
$R^3$ is selected from the group consisting of hydrogen, halo, alkyl, alkenyl, alkynyl, aryl, arylalkyl, heteroarylalkyl, aroylmethyl, acyl, acylalkyl, $(R^4)_2$N-alkylene, and

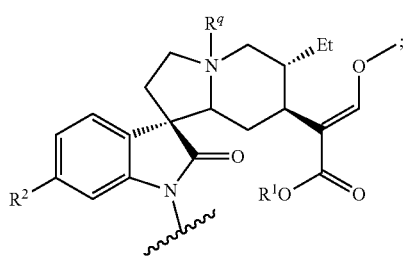

and
each $R^4$ is independently selected from the group consisting of hydrogen, alkyl, alkenyl, aryl, arylalkyl, heteroarylalkyl, acyl, and acylmethyl;
provided that the compound is an EphA4 inhibitor.

2. The compound of claim 1, wherein R¹ is methyl.

3. The compound of claim 1, wherein R² is hydrogen or biotinyl.

4. The compound of claim 1, wherein R$^q$ is methyl or an electron pair.

5. The compound of claim 1, wherein L is an alkylene group of the formula —(CH$_2$)$_n$, wherein n is an integer from 3 to 12.

6. The compound of claim 5, wherein n is an integer from 5 to 10, from 5 to 9, from 6 to 10, or from 6 to 8.

7. The compound of claim 1, wherein X is a bond, —O—, or —NH—.

8. The compound of claim 1, wherein (i) R³ is not hydrogen;

(ii) R³ is halo;

(iii) R³ is methyl, heterocyclylalkyl, or heteroarylalkyl;

(iv) R³ is aryl;

(v) R³ is arylalkyl;

(iv) R³ is acyl; or (v) R³ is (4-methoxybenzoyl)methyl, allyl, cinnamyl, 6-aminohexyl, 2-pyrrolidin-1-ylethyl, 3-imidazol-1-yl-propyl, or (R⁴)NH-alkylene.

9. The compound of claim 1, wherein X is —O—; and wherein R³ is 4-hydroxyphenyl, 4-benzyloxyphenyl, or 3,4-dimethoxyphenyl.

10. The compound of claim 1, wherein R⁴ is hydrogen or biotinyl.

11. A method for treating a subject suffering from a disease involving EphA4 signaling, comprising administering to the subject an effective amount of an inhibitor for EphA4 signaling, wherein the disease is selected from the group consisting of Alzheimer's disease, traumatic brain injury, stroke, spinal cord injury, inflammation, depression, and anxiety; and the inhibitor is

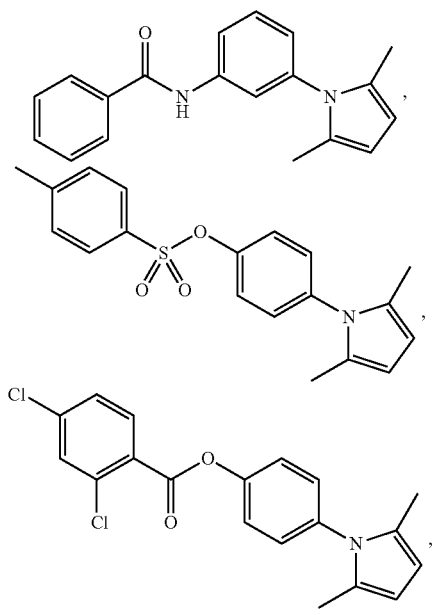

or a compound of Formula I:

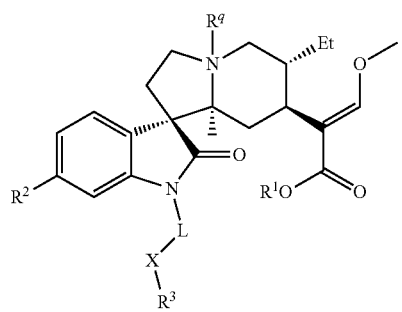

or a pharmaceutically acceptable salt thereof; wherein each R¹ is a member independently selected from the group consisting of hydrogen and alkyl;

each R² is a member independently selected from the group consisting of hydrogen and acyl;

each R$^q$ is a member independently selected from the group consisting of an electron pair, lower alkyl, allyl, and arylmethyl;

L is an alkylene;

X is selected from the group consisting of a bond, —O—, —S—, and —N(R⁴)—;

R³ is selected from the group consisting of hydrogen, halo, alkyl, alkenyl, alkynyl, aryl, arylalkyl, heteroarylalkyl, aroylmethyl, acyl, acylalkyl, (R⁴)$_2$N-alkylene, and

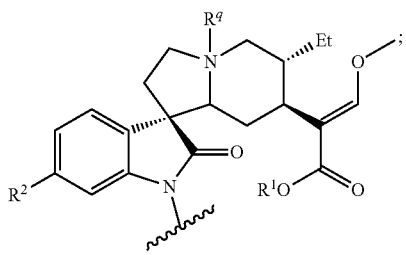

and each R⁴ is independently selected from the group consisting of hydrogen, alkyl, alkenyl, aryl, arylalkyl, heteroarylalkyl, acyl, and acylmethyl.

12. The method of claim 11, wherein the inhibitor is the compound of Formula I.

13. The method of claim 11, wherein the inhibitor is present in a pharmaceutical composition along with a pharmaceutically acceptable excipient.

14. A kit for treating a disease involving EphA4 signaling, comprising an inhibitor for EphA4 signaling, wherein the disease is selected from the group consisting of Alzheimer's disease, traumatic brain injury, stroke, spinal cord injury, inflammation, depression, and anxiety; and the inhibitor is

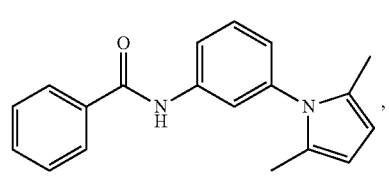

-continued

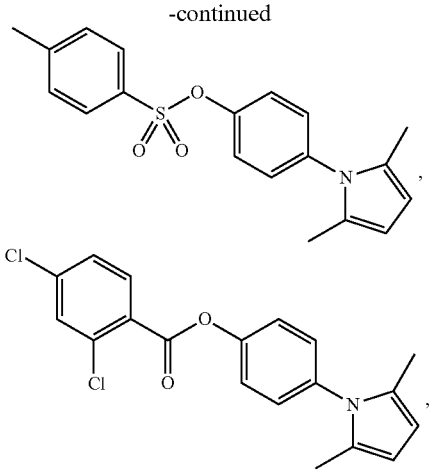

or a compound of Formula I:

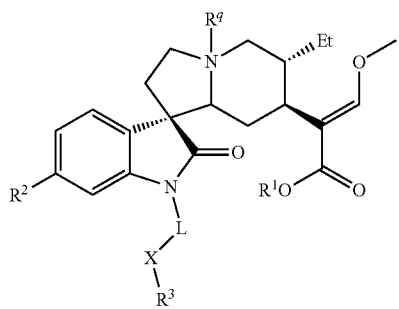

or a pharmaceutically acceptable salt thereof; wherein
each $R^1$ is a member independently selected from the group consisting of hydrogen and alkyl;
each $R^2$ is a member independently selected from the group consisting of hydrogen and acyl;
each $R^q$ is a member independently selected from the group consisting of an electron pair, lower alkyl, allyl, and arylmethyl;
L is an alkylene;
X is selected from the group consisting of a bond, —O—, —S—, and —N($R^4$)—;
$R^3$ is selected from the group consisting of hydrogen, halo, alkyl, alkenyl, alkynyl, aryl, arylalkyl, heteroarylalkyl, aroylmethyl, acyl, acylalkyl, $(R^4)_2$N-alkylene, and

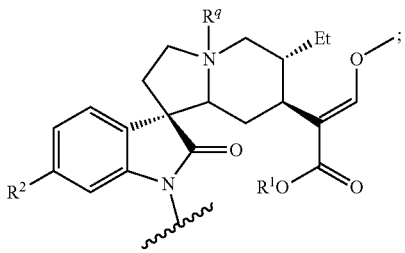

and
each $R^4$ is independently selected from the group consisting of hydrogen, alkyl, alkenyl, aryl, arylalkyl, heteroarylalkyl, acyl, and acylmethyl.

15. The kit of claim 14, comprising multiple containers containing the inhibitor in a daily administration dosage.

16. The kit of claim 14, wherein the inhibitor is the compound of Formula I.

17. The kit of claim 14, wherein the inhibitor is present in a pharmaceutical composition along with a pharmaceutically acceptable excipient.

18. The kit of claim 17, wherein the pharmaceutical composition is formulated for oral administration.

19. The kit of claim 14, further comprising an instructional manual.

20. The method of claim 11, wherein the inhibitor is

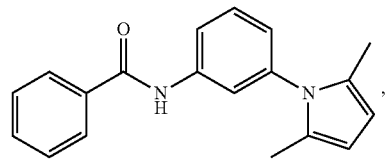

21. The compound of claim 1, wherein the compound is selected from the group consisting of:

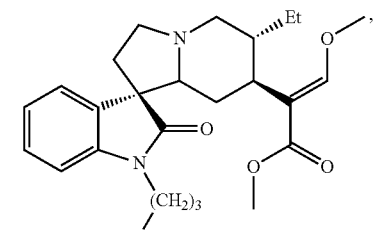

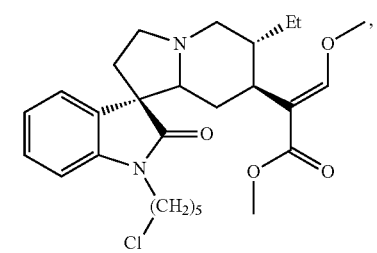

71
-continued
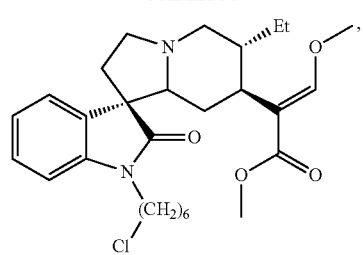
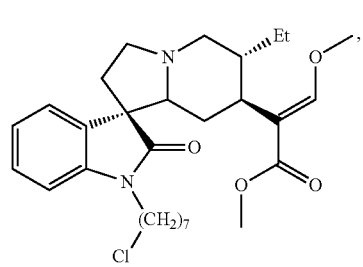
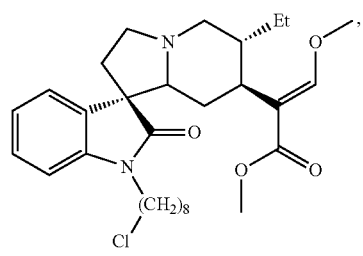
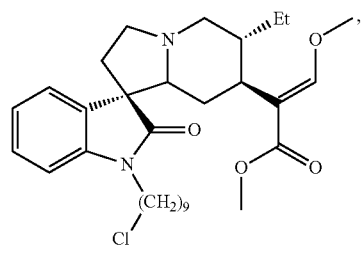
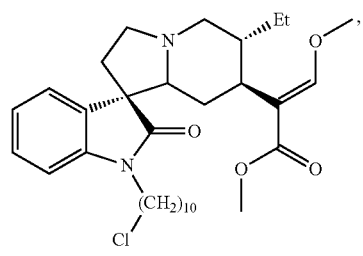
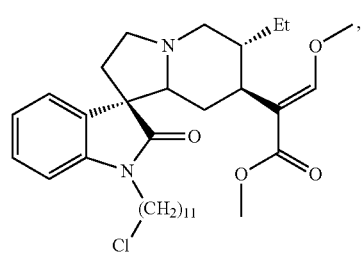
72
-continued
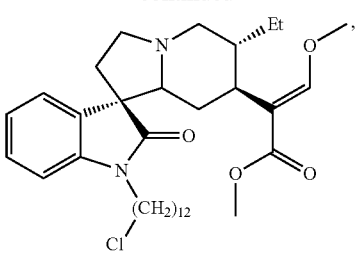
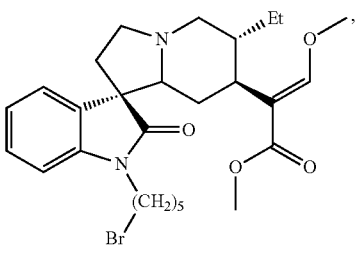
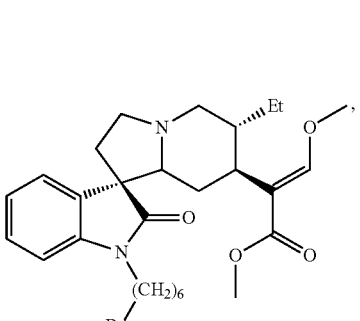
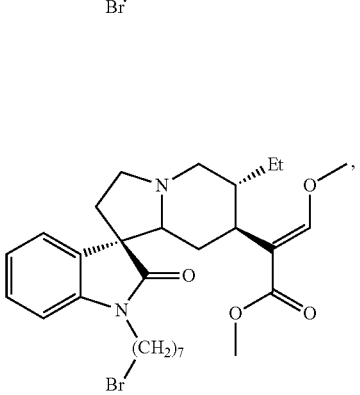
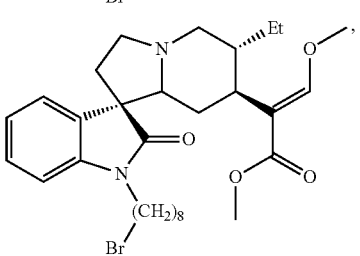
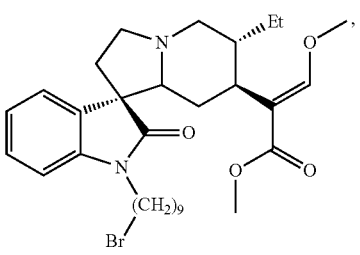

73
-continued
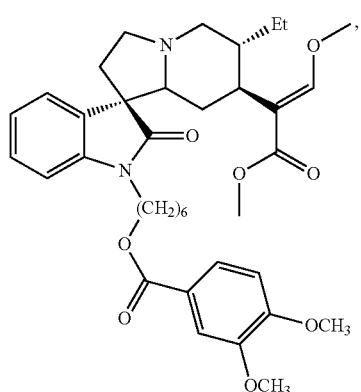
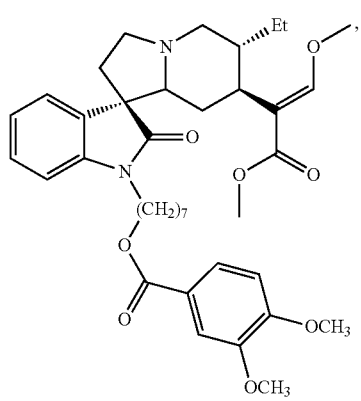
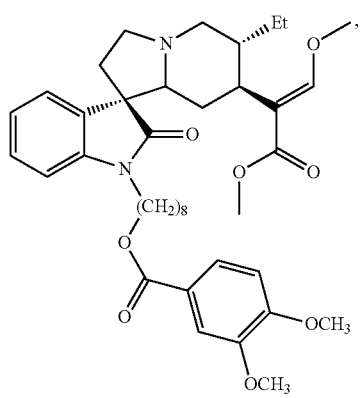
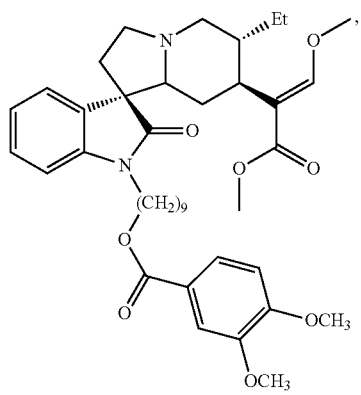
74
-continued
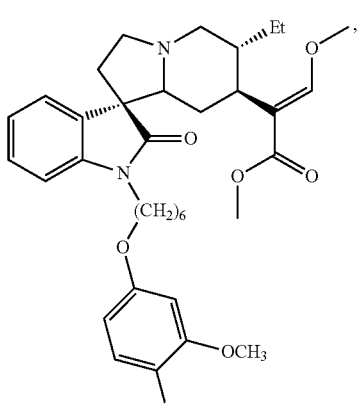
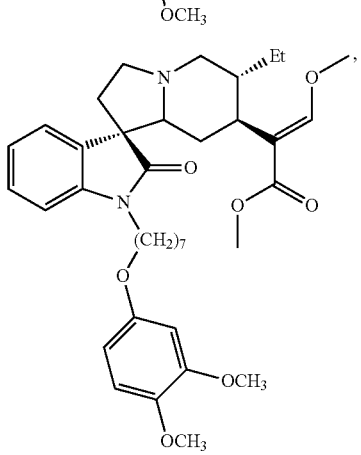
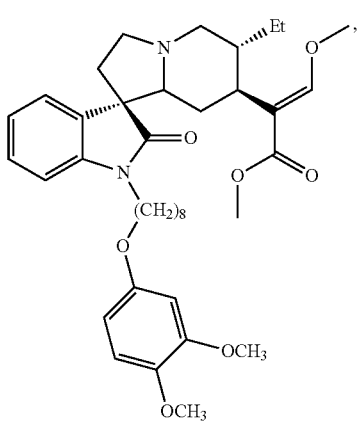
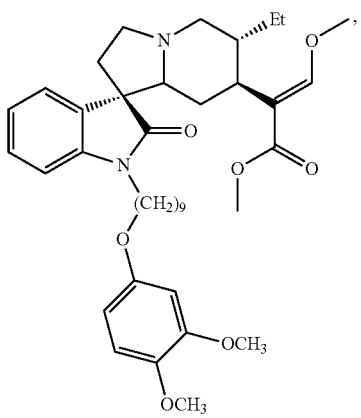

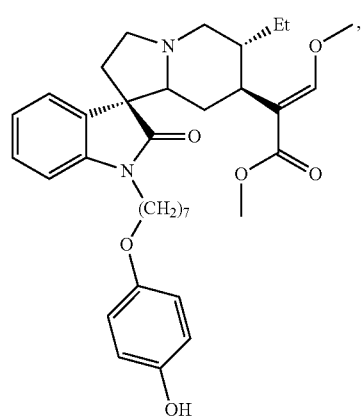
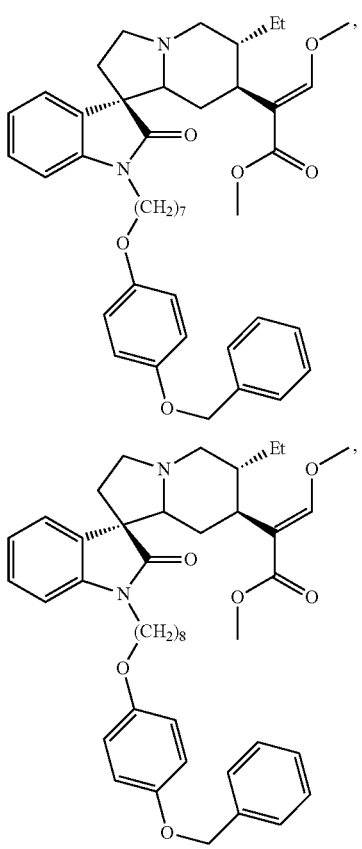
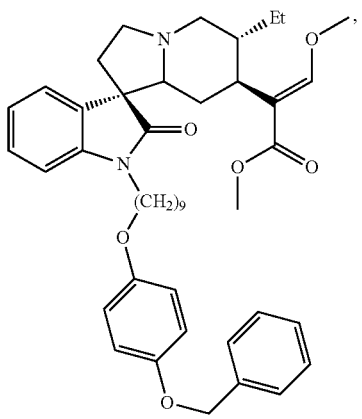
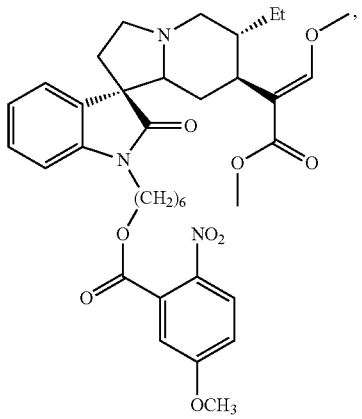

77
-continued
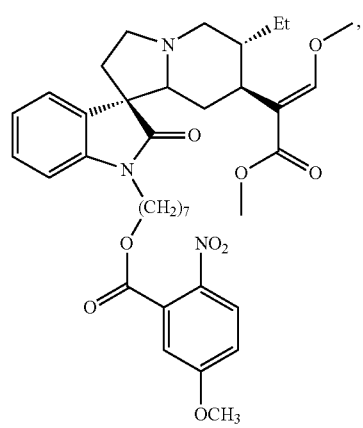
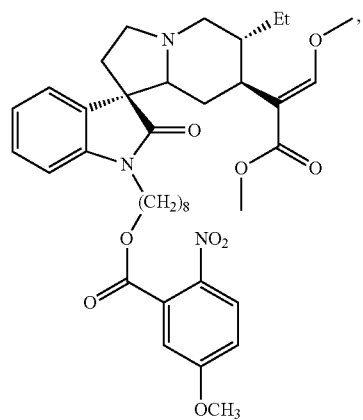
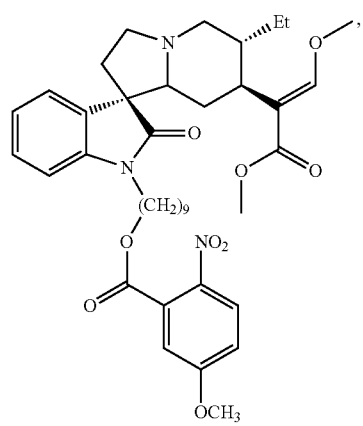
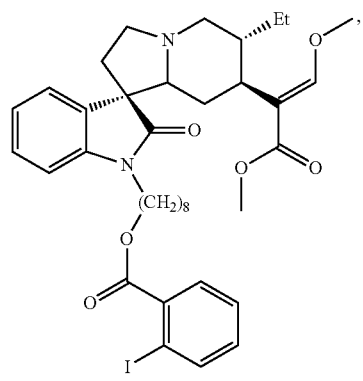
78
-continued
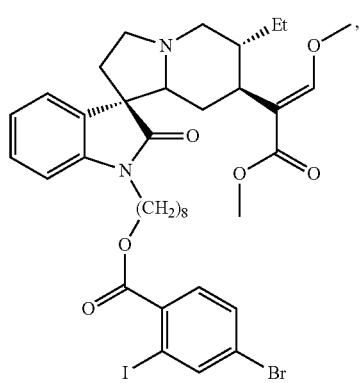
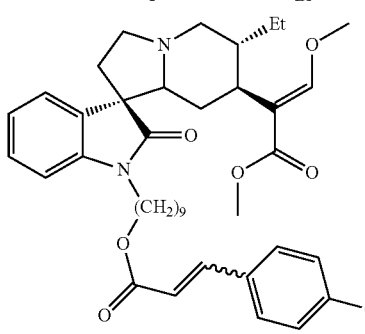
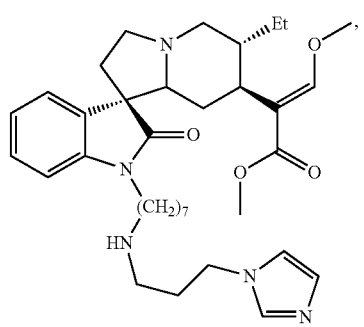
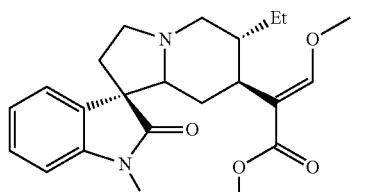
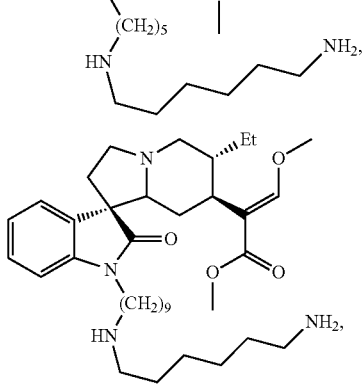

79
-continued
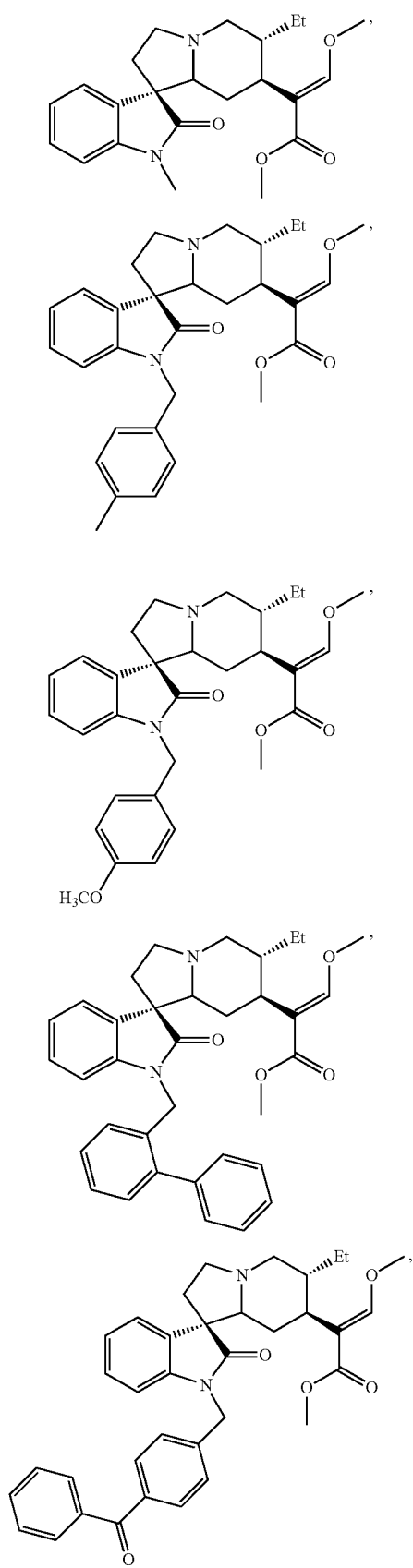
80
-continued
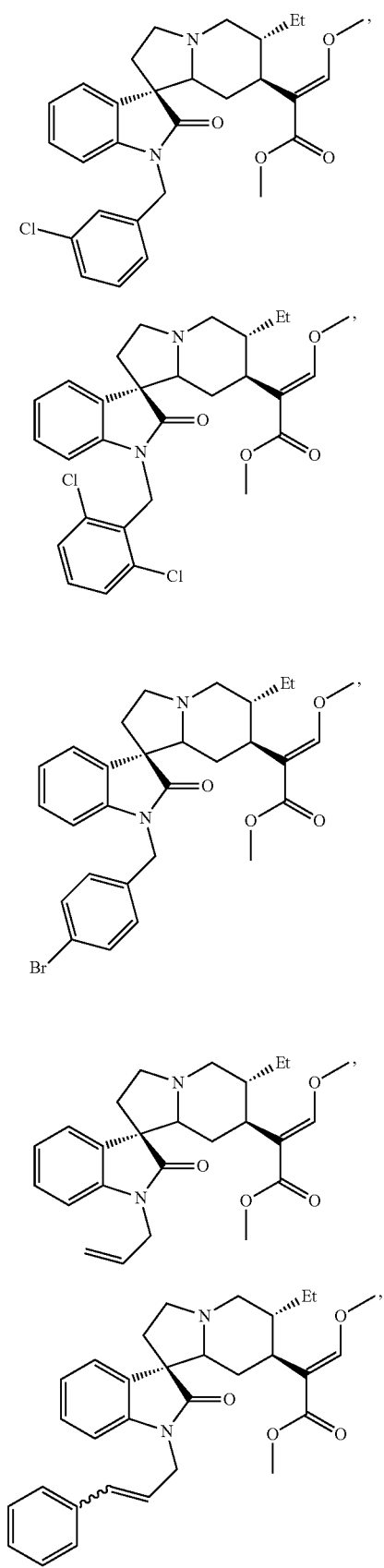

81
-continued
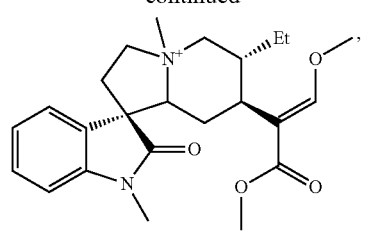
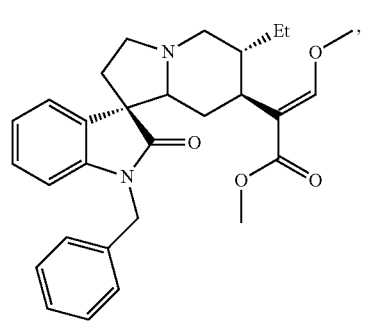
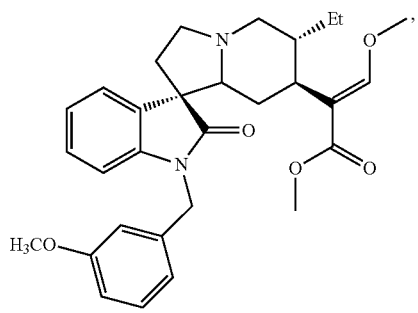
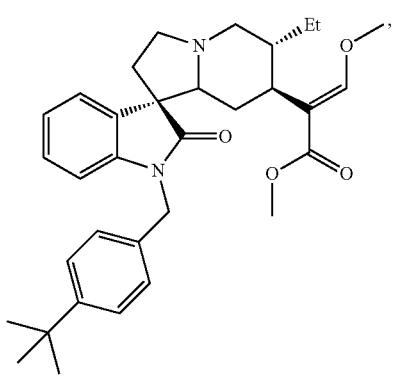
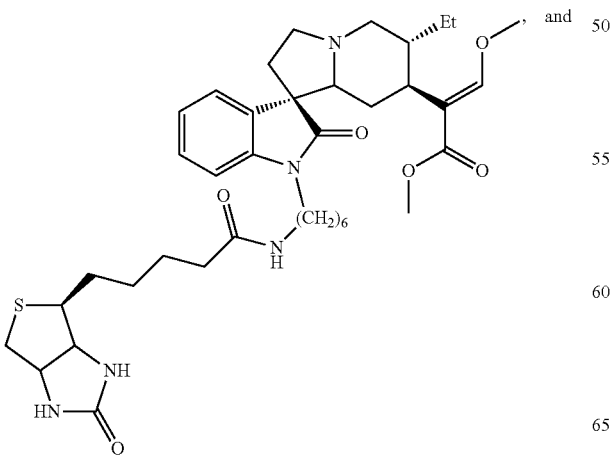
and
82
-continued
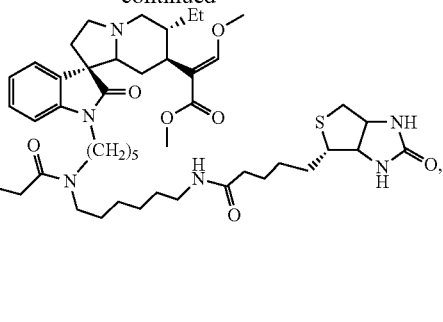
or a pharmaceutically acceptable salt thereof.
22. The method of claim 11, wherein the inhibitor is selected from the group consisting of:
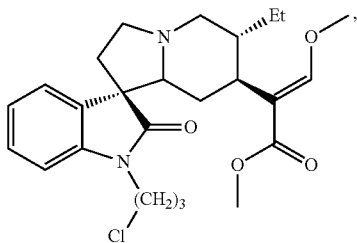
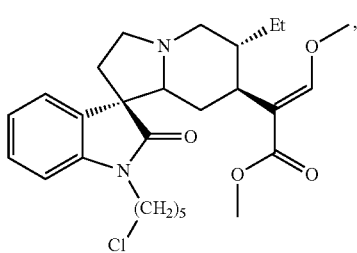
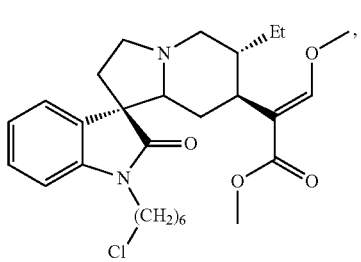
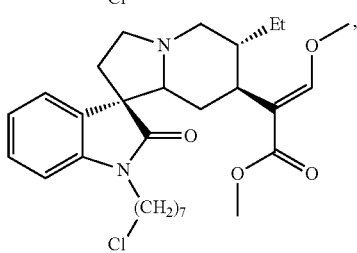

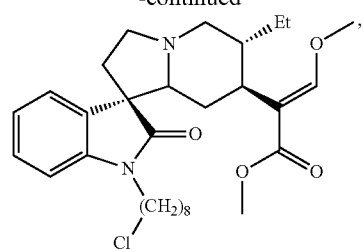
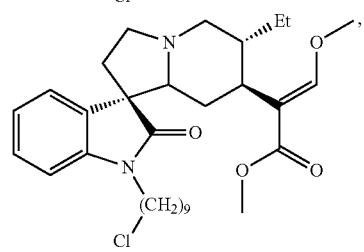
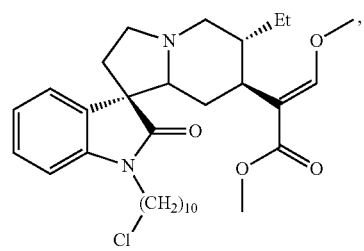
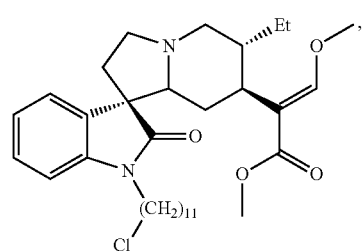
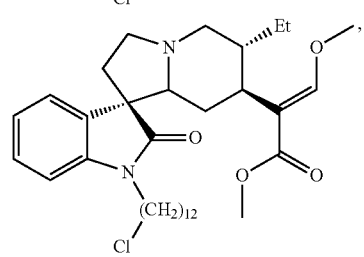
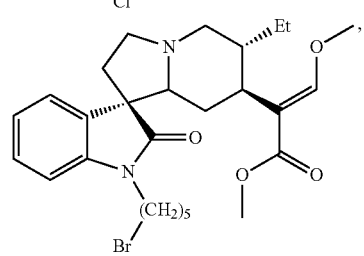
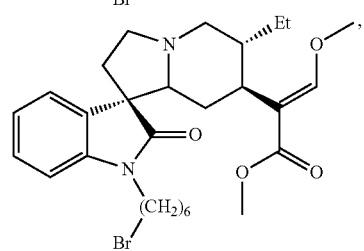
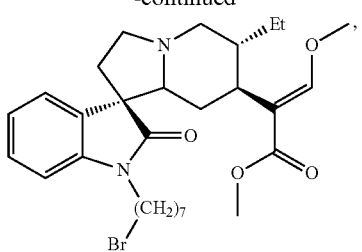
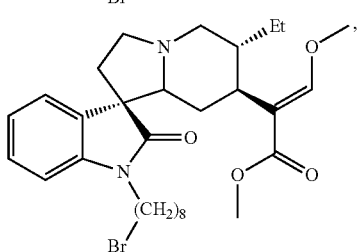
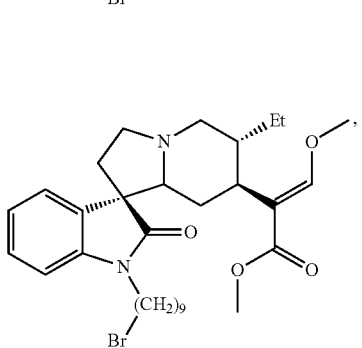
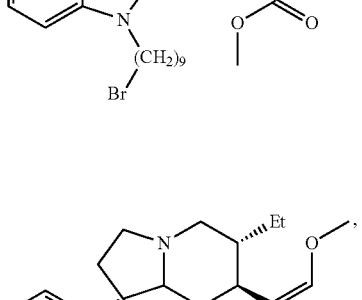
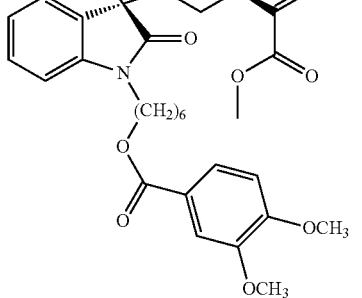
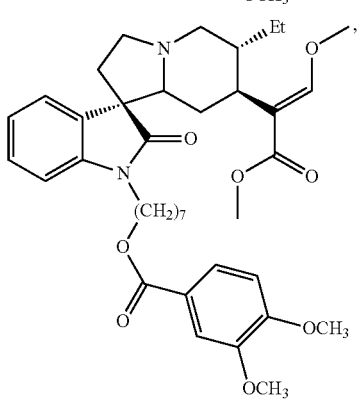

85
-continued
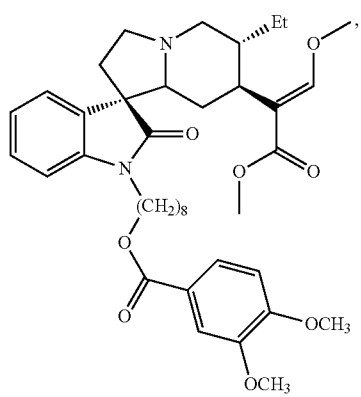
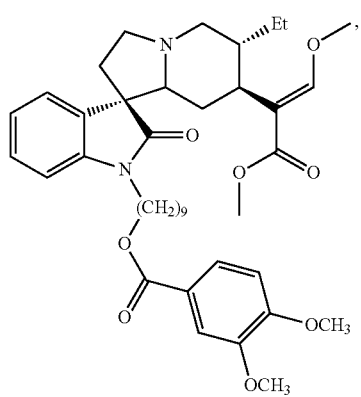
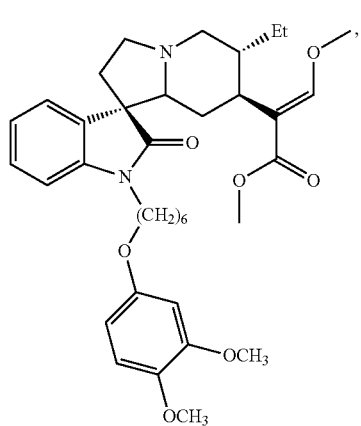
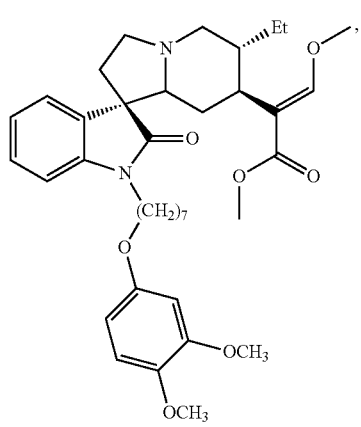
86
-continued
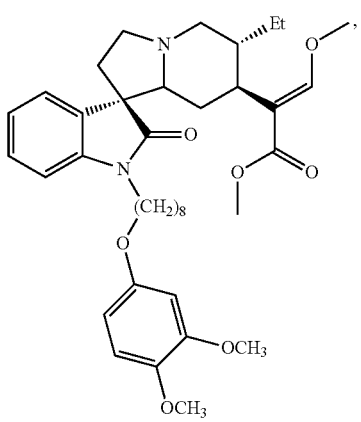
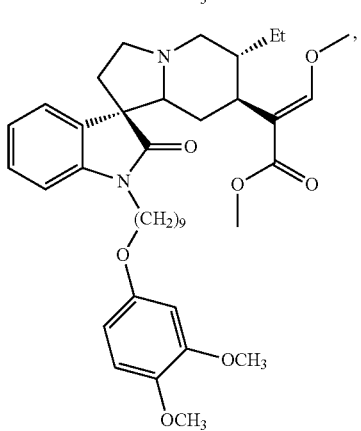
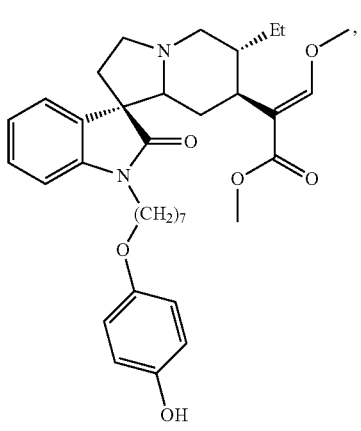
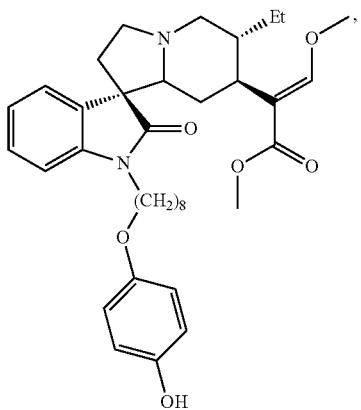

87
-continued
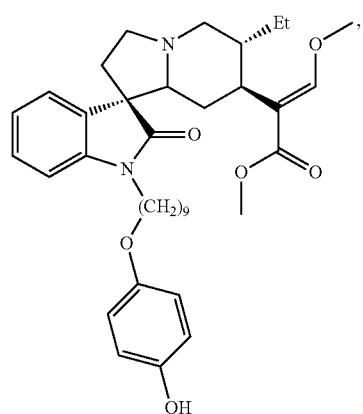
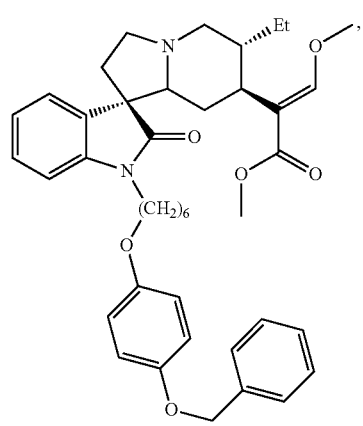
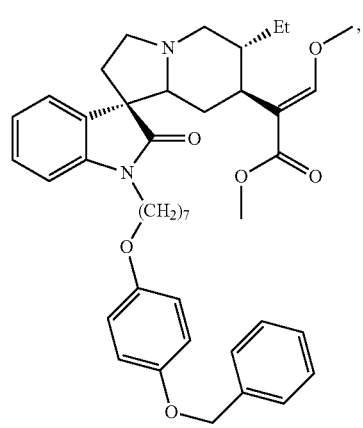
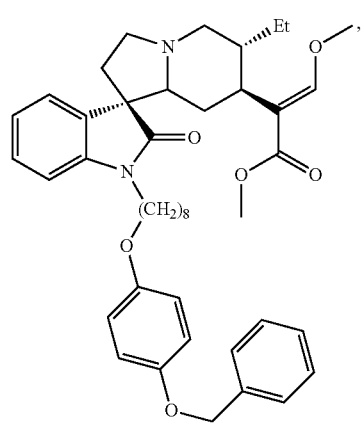
88
-continued
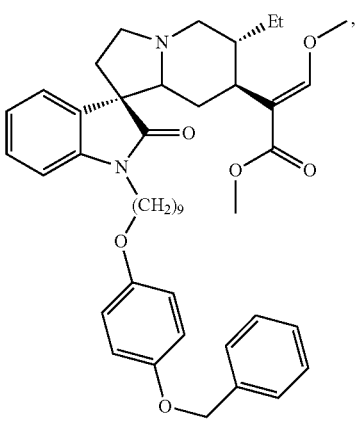
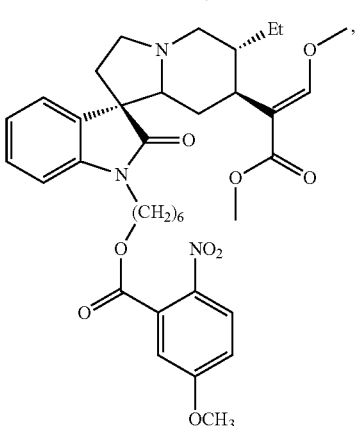
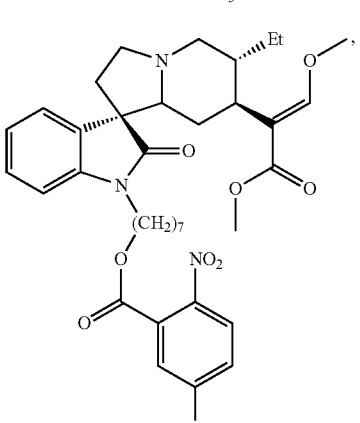
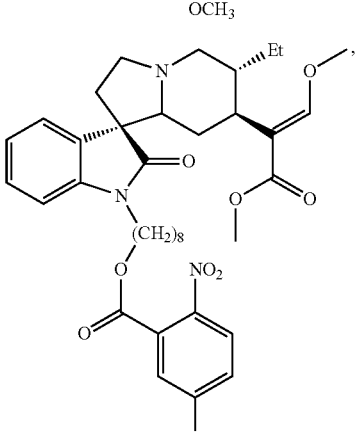

89
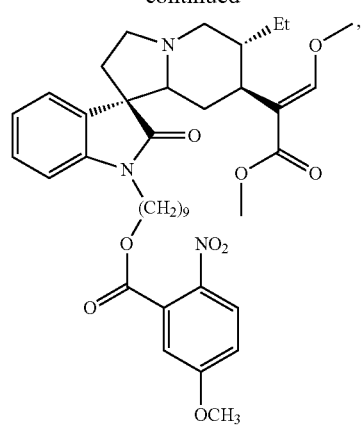
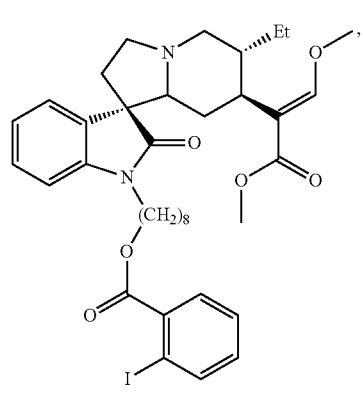
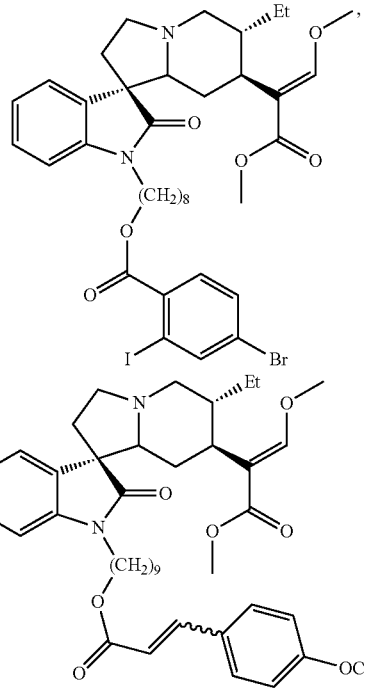
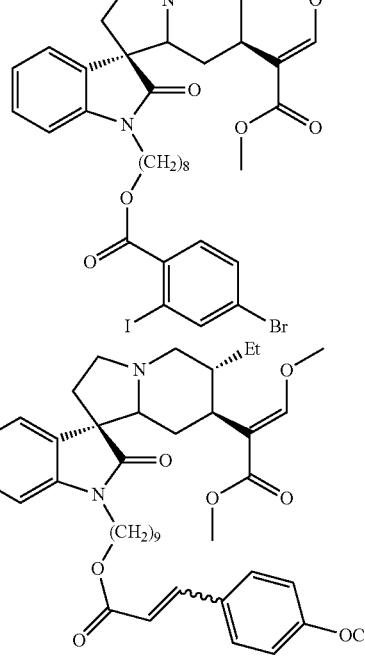
90
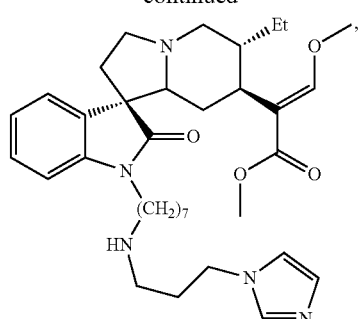
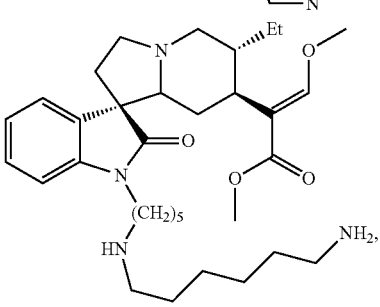
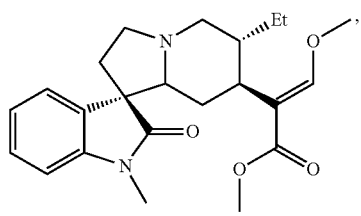
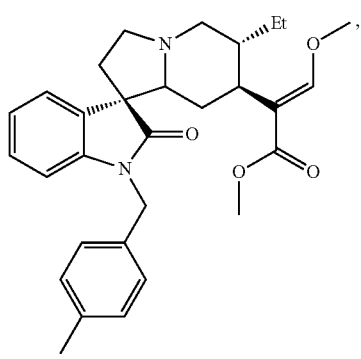
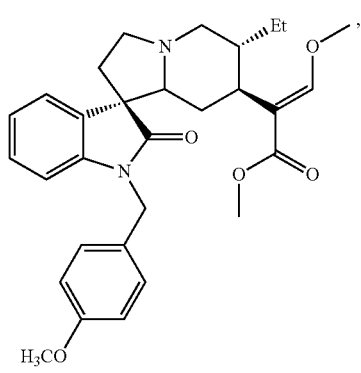

91
-continued
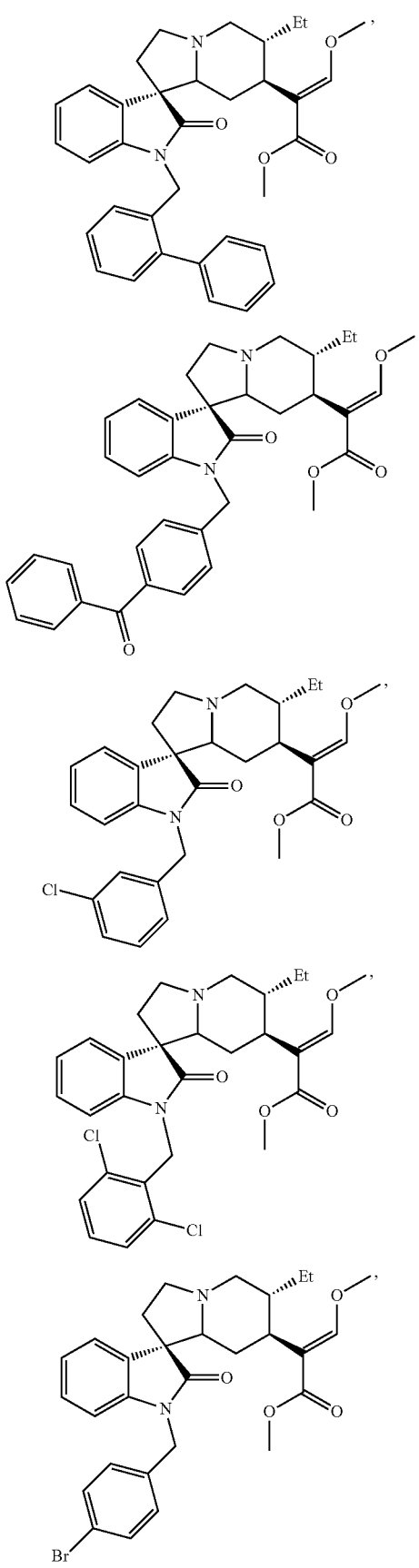
92
-continued
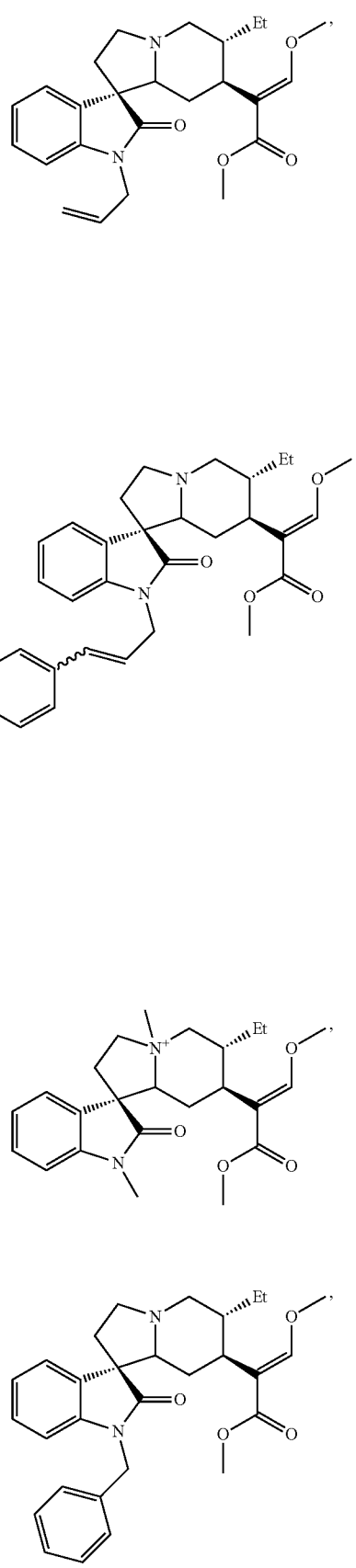

93
-continued
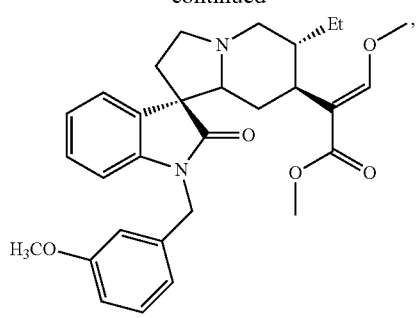
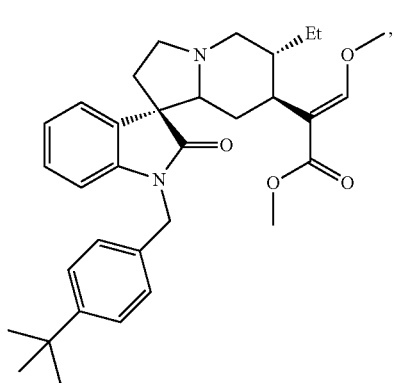
94
-continued
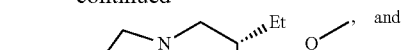
or a pharmaceutically acceptable salt thereof.
* * * * *

UNITED STATES PATENT AND TRADEMARK OFFICE
CERTIFICATE OF CORRECTION

PATENT NO. : 9,629,830 B2  
APPLICATION NO. : 14/905723  
DATED : April 25, 2017  
INVENTOR(S) : Nancy Yuk Yu Ip et al.

Page 1 of 1

It is certified that error appears in the above-identified patent and that said Letters Patent is hereby corrected as shown below:

In the Claims

In Claim 22, please insert the following structure at Column 90, Line 30:

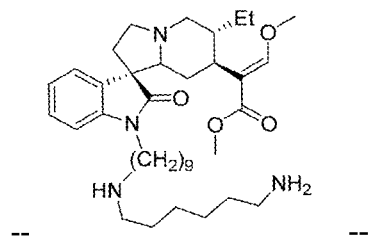

-- --

Signed and Sealed this  
Seventeenth Day of July, 2018

Andrei Iancu  
*Director of the United States Patent and Trademark Office*